United States Patent
Heintz et al.

(10) Patent No.: US 6,451,791 B1
(45) Date of Patent: Sep. 17, 2002

(54) AMIDOAROMATIC RING SULFONAMIDE HYDROXAMIC ACID COMPOUNDS

(75) Inventors: Robert M. Heintz, Ballwin; Daniel P. Getman, Chesterfield; Joseph J. McDonald, Ballwin; Gary A. DeCrescenzo, St. Charles; Susan C. Howard, Fenton; S. Zaheer Abbas, St. Louis, all of MO (US)

(73) Assignee: Monsanto Company, Skokie, IL (US)

( * ) Notice: Subject to any disclaimer, the term of this patent is extended or adjusted under 35 U.S.C. 154(b) by 0 days.

(21) Appl. No.: 09/230,205

(22) PCT Filed: Mar. 4, 1998

(86) PCT No.: PCT/US98/04299
§ 371 (c)(1),
(2), (4) Date: Jun. 4, 1999

(87) PCT Pub. No.: WO98/39329
PCT Pub. Date: Sep. 11, 1998

Related U.S. Application Data

(60) Provisional application No. 60/039,795, filed on Mar. 4, 1997.

(51) Int. Cl.[7] .................. A61K 31/18; A61K 31/24; A61K 31/34; A61K 31/535
(52) U.S. Cl. .................. 514/238.2; 514/231.5; 514/231.8; 514/235.5; 514/316; 514/318; 514/342; 514/343; 514/357; 514/365; 514/438; 514/471; 514/539; 514/603; 544/85; 544/124; 544/130; 544/131; 544/133; 544/137; 544/141; 544/146; 544/148; 544/160; 546/194; 546/233; 546/234; 546/236; 546/237; 546/247; 546/265; 546/337; 546/338; 548/204; 549/65; 549/426; 560/13; 564/86
(58) Field of Search .................. 514/238.2, 357, 514/539, 603, 231.5, 231.8, 237.2, 235.5, 316, 318, 342, 343, 365, 438, 471; 544/160, 85, 124, 130, 133, 131, 146, 137, 141, 148; 546/338, 194, 247, 233, 234, 236, 237, 265, 337; 560/13; 564/86; 548/204; 549/65, 426

(56) References Cited

U.S. PATENT DOCUMENTS

| | | | |
|---|---|---|---|
| 4,337,197 A | 6/1982 | Gordon et al. | 260/239 |
| 5,455,258 A | 10/1995 | MacPherson et al. | 514/357 |
| 5,506,242 A | 4/1996 | MacPherson et al. | 514/336 |
| 5,552,419 A | 9/1996 | MacPherson et al. | 514/357 |
| 5,646,167 A * | 7/1997 | MacPherson et al. | 514/357 |
| 6,150,394 A | 11/2000 | Watannabe et al. | |

FOREIGN PATENT DOCUMENTS

| | | |
|---|---|---|
| EP | 0 757 984  * | 2/1997 |
| WO | WO 95/35276 | 12/1995 |
| WO | WO 96/26223 | 8/1996 |
| WO | WO 97/27174 | 7/1997 |
| WO | WO 98/07742 | 2/1998 |

OTHER PUBLICATIONS

Schwartz et al., *Progr. Med. Chem.*, 29:271–334(1992).
Rasmussen et al., *Pharmacol. Ther.*, 75(1): 69–75 (1997).
Denis et al., *Invest. New Drugs*, 15(3): 175–185 (1997).
Gearing et al. *Nature* 376, 555–557 (1994).
McGeehan et al., *Nature* 376, 558–561 (1994).
Mitchell et al., *J. Clin. Invest.*, 97:761–768 (1996).
Reboul et al., *J. Clin. Invest.*, 97:2011–2019 (1996).
A Model of Angiogenesis in the Mouse Cornea; Kenyon, BM, et al., Investigative Ophthalmology & Visual Science, Jul. 1996, vol. 37, No. 8.
Knight et al., FEBS Lett. 296(3):263 (1992).

* cited by examiner

*Primary Examiner*—Peter O'Sullivan
(74) *Attorney, Agent, or Firm*—Harness, Dickey & Pierce, P.L.C.

(57) ABSTRACT

An amidoaromatic ring sulfonamide hydroxamic acid compound that inter alia inhibits matrix metalloprotease activity is disclosed, as are a treatment process that comprises administering a contemplated amidoaromatic ring sulfonamide hydroxamic acid compound in a MMP enzyme-inhibiting effective amount to a host having a condition associated with pathological matrix metalloprotease activity.

34 Claims, No Drawings

AMIDOAROMATIC RING SULFONAMIDE HYDROXAMIC ACID COMPOUNDS

PRIORITY CLAIM TO RELATED PATENT APPLICATIONS

This patent claims priority as a national-phase application of PCT Patent Application No. PCT/US98/04299 (Int'l Filing Date Mar. 4, 1998; WIPO Int'l Publ. No. WO 98/39329; Int'l Publ. Date Sep. 11, 1998 (in English)), which, in turn, claims priority to U.S. Provisional Patent Application Serial No. 60/039,795 (filed Mar. 4, 1997). The entire texts of both those patent applications are incorporated by reference into this patent.

DESCRIPTION

1. Technical Field

This invention is directed to proteinase (protease) inhibitors, and more particularly to amidoaromatic ring sulfonamide hydroxamic acid compounds that, inter alia, exhibit activity as inhibitors for matrix metalloproteinases, compositions of proteinase inhibitors, intermediates for the syntheses of proteinase inhibitors, processes for the preparation of proteinase inhibitors and processes for treating pathological conditions associated with pathological matrix metalloproteinase-activity.

2. Background of the Invention

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason leads to a number of disease states. Inhibition of the enzymes responsible loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; Alzheimer's Disease; coronary thrombosis and bone disease. Defective injury repair processes also occur. This can produce improper wound healing leading to weak repairs, adhesions and scarring. These latter defects can lead to disfigurement and/or permanent disabilities as with post-surgical adhesions.

Matrix metalloproteases are also involved in the biosynthesis of tumor necrosis factor (TNF) and inhibition of the production or action of TNF and related compounds is an important clinical disease treatment mechanism. TNF-$\alpha$, for example, is a cytokine that at present is thought to be produced initially as a 28 kD cell-associated molecule. It is released as an active, 17 kD form that can mediate a large integer of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal.

TNF-$\alpha$ convertase is a metalloproteinase involved in the formation of active TNF-$\alpha$. Inhibition of TNF-$\alpha$ convertase inhibits production of active TNF-$\alpha$. Compounds that inhibit both MMPs activity have been disclosed in WIPO International Publication Nos. WO 94/24140, WO 94/02466 and WO 97/20824. There remains a need for effective MMP and TNF-$\alpha$ convertase inhibiting agents. Compounds that inhibit MMPs such as collagenase, stromelysin and gelatinase have been shown to inhibit the release of TNF (Gearing et al. Nature 376, 555–557 (1994), McGeehan et al., Nature 376, 558–561 (1994)).

MMPs are involved in other biochemical processes in mammals as well. Included is the control of ovulation, post-partum uterine involution, possibly implantation, cleavage of APP ($\beta$-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin (MMP-3), gelatinase (MMP-2), or collagenase III (MMP-13) are the relatively most important enzyme or enzymes to inhibit especially when compared with collagenasd I (MMP-1). A drug that does not inhibit collagenase I can have a superior therapeutic profile. Osteoarthritis, another prevalent disease wherein it is believed that cartilage degradation in inflamed joints is at least partially caused by MMP-13 released from cells such as stimulated chrondrocytes, may be best treated by administration of drugs one of whose modes of action is inhibition of MMP-13. See, for example, Mitchell et al., *J. Clin. Invest.*, 97:761–768 (1996) and Reboul et al.,*J. Clin. Invest.*, 97:2011–2019 (1996).

Inhibitors of metalloproteases are known. Examples include natural biochemicals such as tissue inhibitor of metalloproteinase (TIMP), $\alpha_2$-macroglobulin and their analogs or derivatives. These are high molecular weight protein molecules that form inactive complexes with metalloproteases. An integer of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure.

Thiol group-containing amide or peptidyl amide-based metalloprotease (MMP) inhibitors are known as is shown in, for example, WO95/12389, WO96/11209 and U.S. Pat. No. 4,595,700. Hydroxamate group-containing MMP inhibitors are disclosed in a number of published patent applications such as WO 95/29892, WO 97/24117,and EP 0 780 386 that disclose carbon back-boned compounds, and WO 90/05719, WO 93/20047, WO 95/09841 and WO 96/06074 that disclose hydroxamates that have a peptidyl back-bones or peptidomimetic back-bones, as does the article by Schwartz et al., *Progr. Med. Chem.*, 29:271–334(1992) and those of Rasmussen et al., *Pharmacol. Ther.*, 75(1): 69–75 (1997) and Denis et al., *Invest. New Drugs*, 15(3): 175–185 (1997).

One possible problem associated with known MMP inhibitors is that such compounds often exhibit the same or similar inhibitory effects against each of the MMP enzymes. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate was reported to be another broad-spectrum MMP inhibitor with an enzyme inhibitory spectrum very similar to batimastat, except that marimastat exhibited an $IC_{50}$ value against MMP-3 of 230 nM. Rasmussen et al., *Pharmacol. Ther.*, 75(1): 69–75 (1997).

Meta analysis of data from Phase I/II studies using marimastat in patients with advanced, rapidly progressive, treatment-refractory solid tumor cancers (colorectal, pancreatic, ovarian, prostate). indicated a dose-related reduction in the rise of cancer-specific antigens used as surrogate markers for biological activity. The most common drug-related toxicity of marimastat in those clinical trials was musculoskeletal pain and stiffness, often commencing in the small joints in the hands, spreading to the arms and shoulder. A short dosing holiday of 1–3 weeks followed by dosage reduction permits treatment to continue. Rasmussen et al., *Pharmacol. Ther.*, 75(1): 69–75 (1997). It is thought that the lack of specificity of inhibitory effect among the MMPs may be the cause of that effect.

In view of the importance of hydroxamate MMP inhibitor compounds in the treatment of several diseases and the lack of enzyme specificity exhibited by two of the more potent drugs now in clinical trials, it would be a great benefit if hydroxamates of greater enzyme specificity could be found. This would be particularly the case if the hydroxamate inhibitors exhibited limited inhibition of MMP-1 that is relatively ubiquitous and as yet not associated with any pathological condition, while exhibiting quite high inhibitory activity against one or more of MMP-2, MMP-9 or MMP-13 that are associated with several pathological conditions. The disclosure that follows describes one family of hydroxamate MMP inhibitors that exhibit those desirable activities.

BRIEF SUMMARY OF THE INVENTION

The present invention provides compounds and their pharmaceutically acceptable salts effective as inhibitors of matrix metalloprotease enzyme activity; the provision of such compositions that are effective for the inhibition of metalloproteases (MMPs) believed to be implicated in diseases and disorders involving uncontrolled breakdown of connective tissue. Exemplary diseases and disorders (pathological conditions) include, for example, rheumatoid arthritis, osteoarthritis, septic arthritis, corneal, epidermal or gastric ulceration, snake bite, tumor metastasis, growth, invasion or angiogenesis, periodontal disease, proteinuria, Alzheimer's Disease, multiple sclerosis, coronary thrombosis and bone disease. Also contemplated are the provision of processes for preparing such compositions; the provision of processes for treating pathological conditions associated with abnormal matrix metalloprotease activity. A contemplated process effective for treating such pathological conditions acts by selective inhibition of metalloproteases associated with such conditions with minimal side effects resulting from inhibition of other proteases whose activity is necessary or desirable for normal body function.

Briefly, therefore, the present invention is directed to a compound of Formula I or a pharmaceutically acceptable acid or base addition salt of a compound of Formula I, as well as a pharmaceutical composition of a compound of Formula I or a pharmaceutically acceptable acid or base addition salt of a compound of Formula I, and also a process for treating conditions associated with pathological matrix metalloprotease activity comprising administering a matrix metalloprotease inhibitor in an effective dosage to a host suffering from such condition.

The present invention relates to a compound of Formula I:

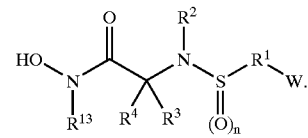

wherein:
n is an integer zero, 1 or 2;
W is independently selected from the group consisting of
—NR$^5$COR$^6$, —NR$^5$S(O)$_z$R$^7$ where z is zero, 1, or 2,
—NR$^5$COOR$^8$, —NR$^5$CONR$^8$R$^9$ and —NR$^{11}$R$^{12}$;
R$^1$ is cycloalkylene, arylene or heteroarylene;
R$^2$ is selected from the group consisting of a hydrogen (hydrido), alkyl, aralkyl, heteroaralkyl, cycloalkylalkyl, heterocycloalkylalkyl, alkoxyalkyl, alkylthioalkyl, hydroxycarbonylalkyl, aroylalkyl, and heteroaroylalkyl group, —(CH$_2$)x—NR$^{11}$R$^{12}$, or —(CH$_2$)x—C(O)NR$^{11}$R$^{12}$, wherein x is an integer from zero to 6;
R$^3$ is selected from the group consisting of a hydrogen (hydrido), alkyl, aryl, aralkyl, thioalkyl, heteroaralkyl, heteroaryl, alkoxyalkoxyalkyl, trifluoromethylalkyl, alkoxycarbonylalkyl, aralkoxycarbonylalkyl, hydroxycarbonylalkyl, alkoxyalkyl, heterocycloalkylalkyl, aryloxyalkyl, alkylthioalkyl, arylthioalkyl, heteroarylthioalkyl group, or a sulfoxide or sulfone of any of said thio-containing groups, a —(CH$_2$)x—C(O)NR$^{11}$R$^{12}$ group, wherein x is an integer from zero to 6, and a —(CH$_2$)y—W group, wherein y is an integer from 1 to 6 and W is defined above;

or $R^2$ and $R^3$ together with the atom chain to which they are attached form a 3–8 membered ring;

$R^4$ is a hydrogen (hydrido) or $C_1$–$C_4$ alkyl group;

$R^5$ is a hydrogen (hydrido) or $C_1$–$C_4$ alkyl group;

$R^6$ is selected from the group consisting of a hydrogen (hydrido), cycloalkyl, heterocycloalkyl, aryl, heteroaryl, aralkyl, heteroaralkyl, cycloalkylalkyl, heterocycloalkylalkyl, alkoxyalkyl, alkylthioalkyl group, and a —$(CH_2)x$—$NR^{11}R^{12}$ group wherein x is an integer from zero to 6. The aryl or heteroaryl groups of $R^6$ are optionally substituted (unsubstituted or substituted) with one or more substituents independently selected from the group consisting of a halo, $C_1$–$C_4$ alkyl, $C_1$–$C_4$ alkoxy, nitro, cyano, hydroxy, carboxy, hydroxycarbonylalkyl, —$(CH_2)x$—$NR^{11}R^{12}$, wherein x is an integer from zero to 6, trifluoromethyl, alkoxycarbonyl, aminocarbonyl, thio, alkylsulfonyl, carbonylamino, aminosulfonyl, alkylsulfonamino, alkoxyalkyl, cycolalkyloxy, alkylthioalkyl or alkylthio;

a) or $R^5$ and $R^6$ together with the atom chain to which they are bonded form a 5- to 7-membered a cyclic amide or imide that is substituted or unsubstituted;

b) or $R^5$ and $R^7$ together with the atom chain to which they are bonded form a 5- to 7-membered a cyclic sulfonamide that is substituted or unsubstituted;

$R^7$ is selected from the group consisting of $R^6$ and alkyl;

$R^8$ and $R^9$ are independently selected from the group consisting of $R^6$ and alkyl, or $R^8$ and $R^9$ together with the depicted nitrogen atom form a 5- to 7-membered ring containing zero or one heteroatom that is oxygen, nitrogen or sulfur;

$R^{11}$ and $R^{12}$ are independently selected from the group consisting of a hydrogen (hydrido), alkyl, aryl, aralkyl, heteroaryl, heteroaralkyl, cycloalkyl, alkanoyl, aralkanoyl, and heteroaralkanoyl group, or $R^{11}$ and $R^{12}$ taken together form a 5 to 8-membered heterocyclo or heteroaryl ring; and $R^{13}$ is a hydrogen (hydrido) or $C_1$–$C_6$ alkyl group.

The present invention also relates to a compound of Formula II:

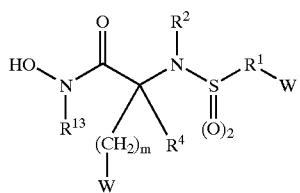

wherein:

m is an integer from 1 to 6;

W, $R^1$, $R^2$ and $R^{13}$ have the meanings described above;

$R^4$ is a hydrogen (hydrido) or $C_1$–$C_4$ alkyl group, as before;

or $R^4$ and W of —$(CH_2)x$—W together with the atom chain to which they are attached form a 4–8-membered ring.

Another particular embodiment of the invention relates to a compound of Formula III:

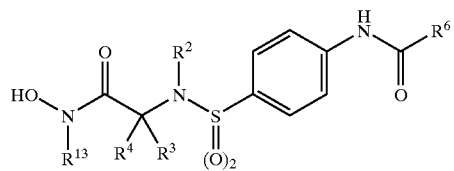

wherein $R^2$, $R^3$, $R^4$, $R^6$ and $R^{13}$ are as described above.

One particular embodiment of the invention relates to a compound of Formula IV:

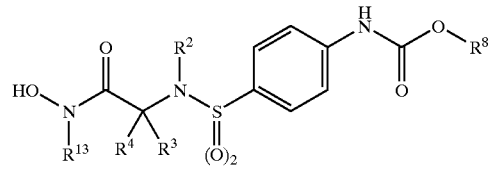

wherein $R^2$, $R^3$, $R^4$, $R^8$ and $R^{13}$ are as defined previously.

A further particular embodiment of the invention relates to a compound of Formula V:

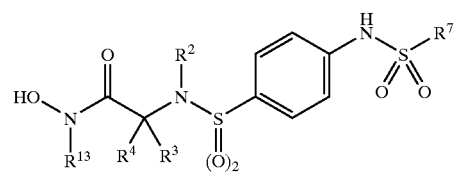

wherein $R^2$, $R^3$, $R^4$, $R^7$ and $R^{13}$ are as defined previously.

Yet another particular embodiment of the invention relates to a compound of Formula VI:

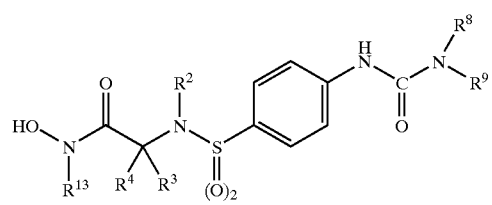

wherein $R^2$, $R^3$, $R^4$, $R^8$, $R^9$ and $R^{13}$ are as defined previously.

A still further particular embodiment of the invention relates to a compound of Formula VII:

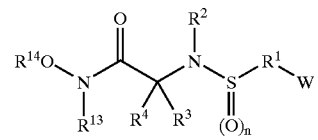

wherein:

n, W, $R^1$, $R^2$, $R^3$, $R^4$ and $R^{13}$ are as defined previously, and $R^{14}$ is selected from the group consisting of a hydrido, $C_1$–$C_6$ alkyl, aryl, substituted aryl, arylalkyl, substituted arylalkyl, alkanoyl, cycloalkylcarbonyl, aralkanoyl, aroyl, and heterocyclylcarbonyl group. $R^{14}$ is preferably a hydrido group, in which case a compound of formula VII becomes a compound of formula I, or an acyl group such as an alkanoyl, cycloalkylcarbonyl, aralkanoyl, aroyl, and heterocyclylcarbonyl group.

A contemplated compound contains an asymmetric carbon atom at the alpha-position so that enantiomeric, d and l or R and S, forms of each compound exist. A particularly preferred stereoconfiguration for a contemplated enantiomeric compound is shown generically below in Formulas IA and VIIA, wherein $R^3$ is hydrido and not depicted, and W, n, the depicted R groups are as defined before.

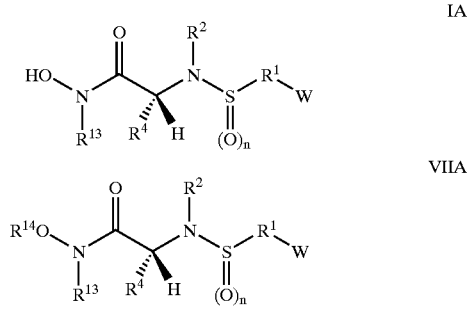

In the above formulas, the dashed line represents a bond that extends beneath the plane of the page, whereas the solid wedge-shaped line represents a bond that extends above the plane of the page, as is usual in stereochemical depictions.

As utilized herein, the term "alkyl", alone or in combination, means a straight-chain or branched-chain alkyl radical containing from 1 to about 12, preferably from 1 to about 10, carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radical having one or more double bonds and containing from 2 to about 12 carbon atoms preferably from 2 to about 10 carbon atoms. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. The term "alkynyl", alone or in combination, means a straight-chain hydrocarbon radical having one or more triple bonds and containing from 2 to about 12 carbon atoms preferably from 2 to about 10 carbon atoms. Examples of alkynyl radicals include ethynyl, 2-propynyl, 3-propynyl, decynyl, 1-butynyl, 2-butynyl, 3-butynyl, and the like.

The term "carbonyl", alone or in combination, means a —C(=O)— group wherein the remaining two bonds (valences) can be independently substituted. The term "thiol" or "sulfhydryl", alone or in combination, means a —SH group. The term "thio" or "thial", alone or in combination, means a thiaether group; i.e., an ether group wherein the ether oxygen is replaced by a sulfur atom.

The term "amino", alone or in combination, means an amine or —NH$_2$ group whereas the term mono-substituted amino, alone or in combination, means a substituted amine —N(H)(substituent) group wherein one hydrogen atom is replaced with a substituent, and disubstituted amine means a —N(substituent)$_2$ wherein two hydrogen atoms of the amino group are replaced with independently selected substituent groups. Amines, amino groups and amides are classes that can be designated as primary (I°), secondary (II°) or tertiary (III°) or unsubstituted, mono-substituted or di-substituted depending on the degree of substitution of the amino nitrogen. Quaternary amine (IV°) means a nitrogen with four substituents (—N+(substituent)$_4$) that is positively charged and accompanied by a counter ion or N-oxide means one substituent is oxygen and the group is represented as (—N$^+$(substituent)$_3$—O$^-$), i.e., the charges are internally compensated.

The term "cyano", alone or in combination, means a —C-triple bond—N (—CN) group. The term "azido", alone or in combination, means a —N-double bond-N-double bond-N (—N=N=N) group.

The term "hydroxyl", alone or in combination, means a —OH group. The term "nitro", alone or in combination, means a —NO$_2$ group.

The term "azo", alone or in combination, means a —N=N— group wherein the bonds at the terminal positions are independently substituted. The term "hydrazino", alone or in combination, means a —NH—NH— group wherein the remaining two bonds (valences) are independently substituted. The hydrogen atoms of the hydrazino group can be replaced, independently, with substituents and the nitrogen atoms can form acid addition salts or be quaternized.

The term "sulfonyl", alone or in combination, means a —S(=O)$_2$— group wherein the remaining two bonds (valences) can be independently substituted. The term "sulfoxido", alone or in combination, means a —S(=O)$_1$— group wherein the remaining two bonds (valences) can be independently substituted. The term "sulfonylamide", alone or in combination, means a —S(=O)$_2$—N= group wherein the remaining three bonds (valences) can be independently substituted. The term "sulfinamido", alone or in combination, means a —S(=O)$_1$N= group wherein the remaining three bonds (valences) can be independently substituted. The term "sulfenamide", alone or in combination, means a —S—N= group wherein the remaining three bonds (valences) can be independently substituted.

The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means an alkyl radical which contains from about 3 to about 8 carbon atoms and in cyclic. The term "cycloalkylalkyl", means an alkyl radical as defined above which is substituted by a cycloalkyl radical containing from about 3 to about 8, preferably from about 3 to about 6, carbon atoms. Examples of such cycloalkyl radicals include cyclopropyl, cyclobutyl, cyclopentyl, cyclohexyl and the like.

The term "aryl", alone or in combination, means a phenyl, indenyl or naphthyl radical that optionally carries one or more substituents selected from alkyl, alkoxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aralkoxycarbonyl", alone or in combination, means a radical of the formula —C(O)—O-aralkyl in which the term "aralkyl" has the significance given above. An example of an aralkoxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

The terms "alkanoyl" or "alkylcarbonyl", alone or in combination, means an acyl radical derived from an alkylcarboxylic acid, examples of which include acetyl, propionyl, butyryl, valeryl, 4-methylvaleryl, and the like. The term "cycloalkylcarbonyl" means an acyl group derived from a monocyclic or bridged cycloalkylcarboxylic acid such as cyclopropanecarbonyl, cyclohexanecarbonyl, adamantanecarbonyl, and the like, or from a benz-fused monocyclic cycloalkylcarboxylic acid which is optionally substituted by, for example, alkanoylamino, such as 1,2,3,4-tetrahydro-2-naphthoyl, 2-acetamido-1,2,3,4-tetrahydro-2-naphthoyl. The terms "aralkanoyl" or "aralkylcarbonyl" mean an acyl radical derived from an aryl-substituted alkylcarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl) benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The heterocyclyl (heterocyclo) or heterocycloalkyl portion of a heterocyclylcarbonyl, heterocyclyloxycarbonyl, heterocyclylalkoxycarbonyl, or heterocyclyalkyl group or the like is a saturated or partially unsaturated monocyclic, bicyclic or tricyclic heterocycle that contains one or more hetero atoms selected from nitrogen, oxygen and sulphur, which is optionally substituted on one or more carbon atoms by a halogen, alkyl, alkoxy, oxo group , and the like, and/or on a secondary nitrogen atom (i.e., —NH—) by an alkyl, aralkoxycarbonyl, alkanoyl, aryl or arylalkyl or on a tertiary nitrogen atom (i.e. =N—) by oxido and which is attached via a carbon atom. The tertiary nitrogen atom with three substituents can also form a N-oxide (=N(O)—) group. The heteroaryl portion of a heteroaroyl, heteroaryloxycarbonyl, or a heteroaralkoxy carbonyl group or the like is an aromatic monocyclic, bicyclic, or tricyclic heterocycle that contains the hetero atoms and is optionally substituted as defined above with respect to the definition of heterocyclyl. Examples of such heterocyclyl and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonyl-imidazol-4-yl, pyrazolyl, pyridyl, pyrazinyl, pyrimidinyl, furyl, tetrahydrofuryl, thienyl, triazolyl, oxazolyl, oxadiazoyl, thiazolyl, thiadiazoyl, indolyl (e.g., 2-indolyl, quinolinyl, (e.g., 2-quinolinyl, 3-quinolinyl, 1-oxido-2-quinolinyl), isoquinolinyl (e.g., 1-isoquinolinyl, 3-isoquinolinyl), tetrahydroquinolinyl (e.g., 1,2,3,4-tetrahydro-2-quinolyl), 1,2,3,4-tetrahydroisoquinolinyl (e.g., 1,2,3,4-tetrahydro-1-oxoisoquinolinyl), quinoxalinyl, 9-carbolinyl, 2-benzofurancarbonyl, benzothiophenyl, 1-,2-,4-or 5-benzimidazolyl, and the like.

The term "cycloalkylalkoxycarbonyl" means an acyl group derived from a cycloalkylalkoxycarboxylic acid of the formula cycloalkylalkyl-O—COOH wherein cycloalkylalkyl has the significance given above. The term "aryloxyalkanoyl" means an acyl radical of the formula aryl-O-alkanoyl wherein aryl and alkanoyl have the significance given above. The term "heterocyclyloxycarbonyl" means an acyl group derived from heterocyclyl-O—COOH wherein heterocyclyl is as defined above. The term "heterocyclylalkanoyl" is an acyl radical derived from a heterocyclyl-substituted alkane carboxylic acid wherein heterocyclyl has the significance given above. The term "heterocyclylalkoxycarbonyl" means an acyl radical derived from a heterocyclyl-substituted alkane-O—COOH wherein heterocyclyl has the significance given above. The term "heteroaryloxycarbonyl" means an acyl radical derived from a carboxylic acid represented by heteroaryl-O—COOH wherein heteroaryl has the significance given above.

The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, and alkyl, aryl, aralkyl, cycloalkyl, cycloalkylalkyl radicals and the like. The term "aminoalkanoyl", means an acyl group derived from an amino-substituted alkanecarboxylic acid wherein the amino group can be a primary, secondary or tertiary amino group containing substituents independently selected from hydrogen, alkyl, aryl, aralkyl, cycloalkyl, cycloalkylalkyl radicals and the like.

The term "halogen" means fluorine, chlorine, bromine or iodine. The term "haloalkyll" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like. The term perfluoroalkyl means an alkyl group wherein each hydrogen has been replaced by a fluorine atom. Examples of such perfluoroalkyl groups, in addition to trifluoromethyl above, are perfluorobutyl, perfluoroisopropyl, perfluorododecyl and perfluorodecyl.

DESCRIPTION OF THE PREFERRED EMBODIMENTS

In accordance with the present invention, it has been discovered that certain novel substituted-aromatic sulfonamide hydroxamic acid compounds are effective for inhibition of matrix metalloproteases ("MMPs") believed to be associated with uncontrolled or otherwise pathological breakdown of connective tissue. In particular, it has been found that these substituted-aromatic ring sulfonamide hydroxamic acid, substituted-aromatic ring sulfinamide hydroxamic acid or substituted-aromatic ring sulfenamide hydroxamic acid compounds are effective for inhibition of collagenase Type III (MMP-13), which is believed to be particularly destructive to tissue if present or generated in abnormal quantities or concentrations. Moreover, it has been discovered that many of these novel sulfur-nitrogen bonded compounds are selective in the inhibition of MMP-13 and/or other MMPs associated with diseased conditions without excessive inhibition of those collagenases essential to normal bodily function such as tissue turnover and repair or other zinc proteases. More particularly, it has been found that many of the substituted-aryl- or substituted-heteroaryl-sulfonamide hydroxamic acids of the invention are selective for MMP-13 with limited or minimal effect on MMP-1.

Set forth in Table 1 to Table 8 inclusive and in Example 1 to Example 15 inclusive are several series of preferred classes of compounds.

TABLE 1

| Example | R₂ | R₃ | R₄ |
|---|---|---|---|
| 4 | propyl-morpholine | isopropyl | 4-bromophenyl |
| 5 | propyl-morpholine | isopropyl | 4-isobutylphenyl |
| 6 | propyl-morpholine | sec-butyl | 4-hydroxyphenyl |
| 7 | propyl-morpholine | sec-butyl | 4-methylthiazol-2-yl |
| 8 | propyl-morpholine | sec-butyl | pyridin-3-yl |
| 9 | 3-ethylpyridine | —CH₃ | 4-isobutylphenyl |
| 10 | 3-ethylpyridine | —CH₃ | 4-acetamidophenyl |
| 11 | 3-ethylpyridine | —CH₃ | 4-sulfamoylphenyl |
| 12 | 3-ethylpyridine | N-propyl-2-(dimethylamino)acetamide | 4-methylphenyl |
| 13 | 3-ethylpyridine | 2-(ethylsulfonyl)thiophene | 4-hydroxyphenyl |
| 14 | propanoyl | isopropyl | thiophen-2-yl |

TABLE 1-continued

Structure: HO-NH-C(=O)-CH(R3)-N(R2)-SO2-C6H4-NH-C(=O)-R4

| Example | R2 | R3 | R4 |
|---|---|---|---|
| 15 | -CH2CH2C(=O)O- (propanoyloxy) | —CH3 | 4-isobutylphenyl |
| 16 | -CH2CH2C(=O)O- | -CH(CH3)CH2CH3 (sec-butyl) | 4-hydroxyphenyl |
| 17 | -CH2CH2C(=O)O- | -CH(CH3)CH2CH3 | 4-methylthiazol-? (thiazolyl) |

TABLE 2

Structure: HO-NH-C(=O)-CH(R3)-N(R2)-SO2-C6H4-NH-C(=O)-O-R4

| Example | R2 | R3 | R4 |
|---|---|---|---|
| 18 | -CH2CH2CH2-morpholino | -CH(CH3)2 (isopropyl) | -CH2-phenyl |
| 19 | -CH2CH2CH2-morpholino | -CH(CH3)2 | -CH2-(4-carboxyphenyl) |
| 20 | -CH2CH2CH2-morpholino | -CH(CH3)CH2CH3 | -CH2CH2CH2-morpholino |
| 21 | -CH2CH2CH2-morpholino | -CH(CH3)CH2CH3 | -CH2-(4-methoxyphenyl) |
| 22 | -CH2CH2CH2-morpholino | -CH(CH3)CH2CH3 | -CH2-(4-methylthiazolyl) |

TABLE 2-continued

| Example | R₂ | R₃ | R₄ |
| --- | --- | --- | --- |
| 23 | 3-pyridyl-CH₂– | –CH₃ | benzyl |
| 24 | 3-pyridyl-CH₂– | –CH₃ | 4-(CO₂H)benzyl |
| 25 | 3-pyridyl-CH₂– | –CH₃ | 3-morpholinopropyl |
| 26 | 3-pyridyl-CH₂– | –CH₂C(O)NH-propyl-N(CH₃)₂ (see structure) | 4-methoxybenzyl |
| 27 | 3-pyridyl-CH₂– | 2-thienyl-SO₂-CH₂– | 4-methoxybenzyl |
| 28 | –CH₂CH₂C(O)O– (propanoyloxy) | –CH₂CH(CH₃)₂ | benzyl |
| 29 | –CH₂CH₂C(O)O– | –CH₃ | 3-morpholinopropyl |
| 30 | –CH₂CH₂C(O)O– | –CH(CH₃)CH₂CH₃ | 4-methoxybenzyl |
| 31 | –CH₂CH₂C(O)O– | –CH(CH₃)CH₂CH₃ | 4-thiazolylmethyl |

TABLE 3

| Example | R₂ | R₃ | R₄ |
|---|---|---|---|
| 32 | 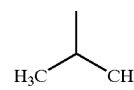 propylmorpholine | 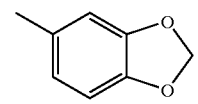 isobutyl | 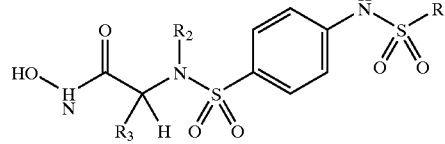 methylenedioxyphenyl |
| 33 | 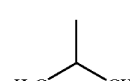 propylmorpholine |  isobutyl | —CH₃ |
| 34 | 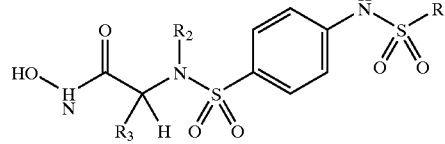 propylmorpholine | 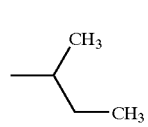 sec-butyl | 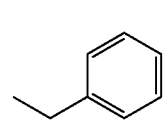 phenyl |
| 35 | 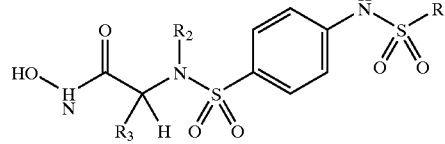 propylmorpholine | 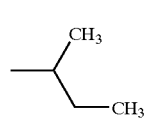 sec-butyl | 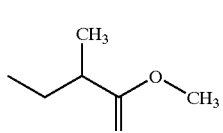 methyl 2-methylbutanoate |
| 36 | 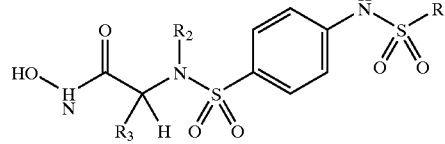 propylmorpholine | 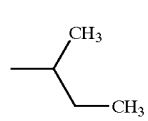 sec-butyl | 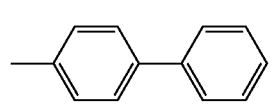 biphenyl |
| 37 | 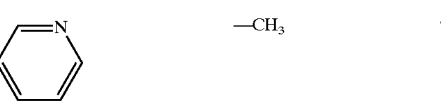 ethylpyridine | —CH₃ |  methylenedioxyphenyl |
| 38 | 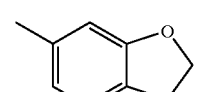 ethylpyridine | —CH₃ | 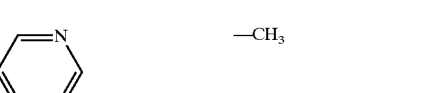 phenyl |
| 39 |  ethylpyridine | —CH₃ | 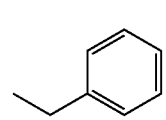 chlorothiophene |
| 40 | 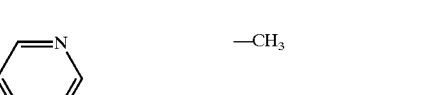 ethylpyridine |  | 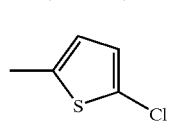 methoxyphenyl |
| 41 | 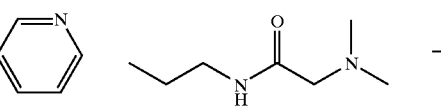 ethylpyridine | 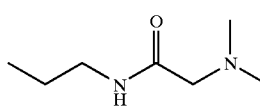 | —CH₃ |
| 42 | 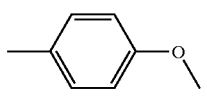 | 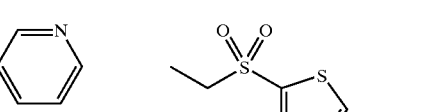 isobutyl | 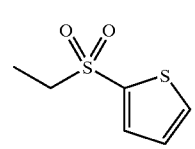 methylenedioxyphenyl |

TABLE 3-continued

[Structure: HO-NH-C(=O)-CH(R3)-N(R2)-S(=O)2-C6H4-NH-S(=O)2-R4]

| Example | R2 | R3 | R4 |
|---|---|---|---|
| 43 | -CH2CH2CH2-C(=O)-O- (butyrate) | -CH3 | -CH2CH2CH2CH2-CH |
| 44 | -CH2CH2CH2-C(=O)-O- | -CH(CH3)2 | -CH2-C6H5 |
| 45 | -CH2CH2CH2-C(=O)-O- | -CH(CH3)CH2CH3 (sec-butyl) | -CH3 |

TABLE 4

[Structure: HO-NH-C(=O)-CH(R3)-N(R2)-S(=O)2-C6H4-NH-C(=O)-R4]

| Example | R2 | R3 | R4 |
|---|---|---|---|
| 46 | -CH2CH2CH2-N(morpholine) | -CH(CH3)2 isobutyl | -NH-C(CH3)3 |
| 47 | -CH2CH2CH2-N(morpholine) | -CH(CH3)2 isobutyl | -N(pyrrolidine) |
| 48 | -CH2CH2CH2-N(morpholine) | -CH(CH3)CH2CH3 | -NH-C6H4-OCH3 |
| 49 | -CH2CH2CH2-N(morpholine) | -CH(CH3)CH2CH3 | -N(morpholine) |
| 50 | -CH2CH2CH2-N(morpholine) | -CH(CH3)CH2CH3 | -NH2 |
| 51 | -CH2CH2-(3-pyridyl) | -CH3 | -NH-C(CH3)3 |

TABLE 4-continued

| Example | R₂ | R₃ | R₄ |
|---|---|---|---|
| 52 | 3-ethylpyridine | —CH₃ | morpholine |
| 53 | 3-ethylpyridine | —CH₃ | 4-methoxyphenylamino |
| 54 | 3-ethylpyridine | propyl-NH-C(O)-CH₂-N(CH₃)₂ | piperidine |
| 55 | 3-ethylpyridine | ethylsulfonyl-thiophene | dimethylamino |
| 56 | butyrate ester | isobutyl | tert-butylamino (N-methyl) |
| 57 | butyrate ester | —CH₃ | dimethylamino |
| 58 | butyrate ester | sec-butyl | morpholine |
| 59 | butyrate ester | sec-butyl | pyrrolidine |

TABLE 5

| Example | R₂ | R₃ | R₄ |
|---|---|---|---|
| 4 | propyl-morpholine | —CH₃ | 4-bromophenyl |

TABLE 5-continued

| Example | R₂ | R₃ | R₄ |
|---|---|---|---|
| 5 | propyl-morpholine | isobutyl (H₃C-CH(CH₃)-) | 4-Br-phenyl |
| 6 | propyl-morpholine | sec-butyl (CH(CH₃)CH₂CH₃) | 4-Br-phenyl |
| 7 | propyl-morpholine | -CH₂CH₂CH₂-NH-C(O)-CH₂-N(CH₃)₂ | 4-Br-phenyl |
| 8 | 3-pyridyl-ethyl | —CH₃ | 4-Br-phenyl |
| 9 | 3-pyridyl-ethyl | isobutyl | 4-Br-phenyl |
| 10 | 3-pyridyl-ethyl | sec-butyl | 4-Br-phenyl |
| 11 | 3-pyridyl-ethyl | -CH₂CH₂CH₂-NH-C(O)-CH₂-N(CH₃)₂ | 4-Br-phenyl |
| 12 | —CH₃ | —CH₃ | 4-Br-phenyl |
| 13 | —CH₃ | isobutyl | 4-Br-phenyl |
| 14 | —CH₃ | sec-butyl | 4-Br-phenyl |
| 15 | —CH₃ | -CH₂CH₂CH₂-NH-C(O)-CH₂-N(CH₃)₂ | 4-Br-phenyl |
| 16 | sec-butyl | —CH₃ | 4-Br-phenyl |

TABLE 5-continued
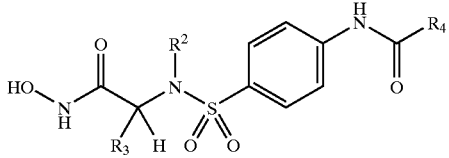
| Example | R₂ | R₃ | R₄ |
|---------|----|----|----|
| 17 | 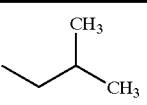 | 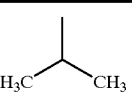 | 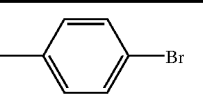 |
| 18 | 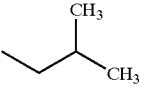 | 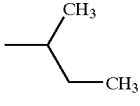 | 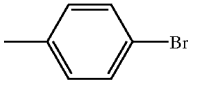 |
| 19 | 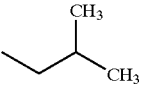 | 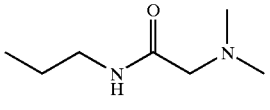 | 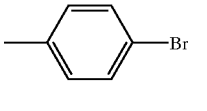 |
| 20 | 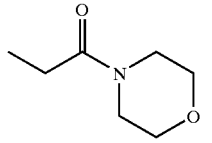 | —CH₃ |  |
| 21 | 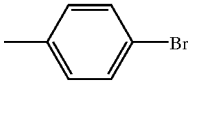 | 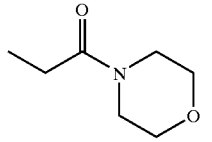 | 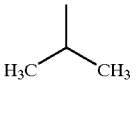 |
| 22 | 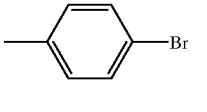 | 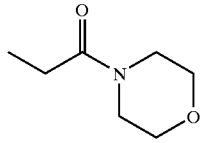 | 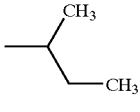 |
| 23 | 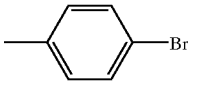 | 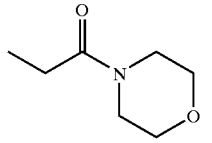 | 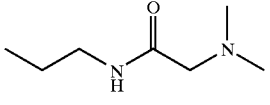 |
| 24 | 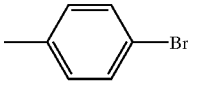 | —CH₃ | 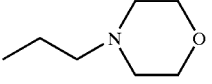 |
| 25 |  | 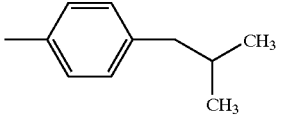 | 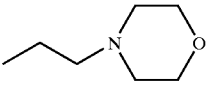 |
| 26 | 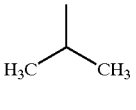 | 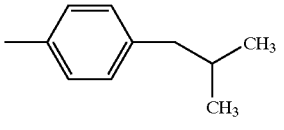 | 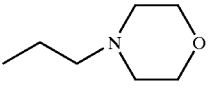 |

TABLE 5-continued
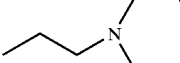
| Example | R₂ | R₃ | R₄ |
|---|---|---|---|
| 27 | 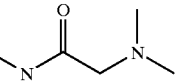 | 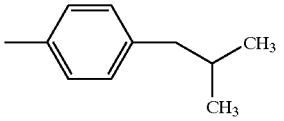 | 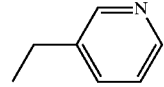 |
| 28 | 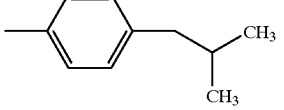 | —CH₃ | 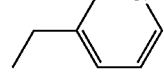 |
| 29 | 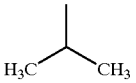 | 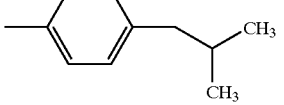 | 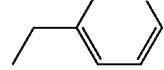 |
| 30 | 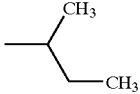 | 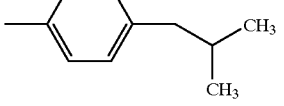 | 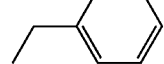 |
| 31 | 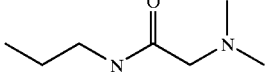 | 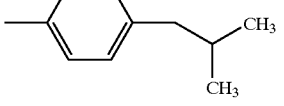 | 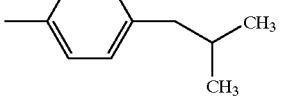 |
| 32 | —CH₃ | —CH₃ | 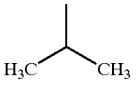 |
| 33 | —CH₃ | 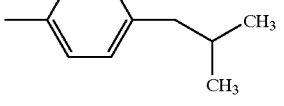 | 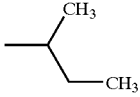 |
| 34 | —CH₃ | 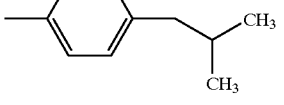 | 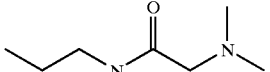 |
| 35 | —CH₃ | 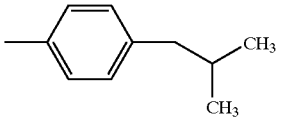 | 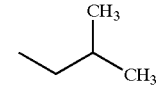 |
| 36 | 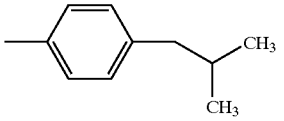 | —CH₃ |  |

TABLE 5-continued
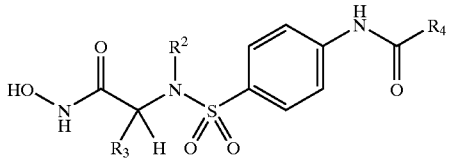
| Example | R₂ | R₃ | R₄ |
|---|---|---|---|
| 37 | 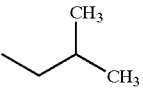 | 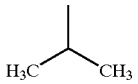 | 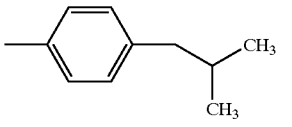 |
| 38 | 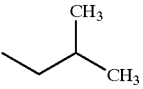 | 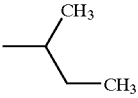 | 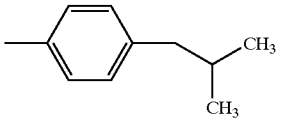 |
| 39 | 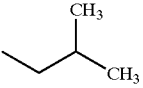 | 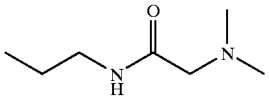 | 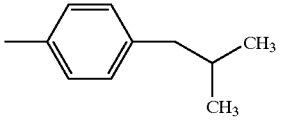 |
| 40 | 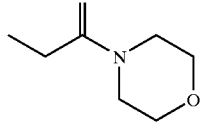 | —CH₃ |  |
| 41 | 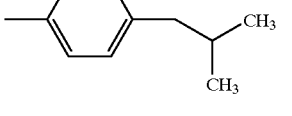 | 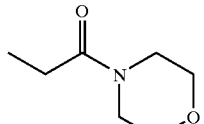 | 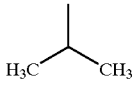 |
| 42 | 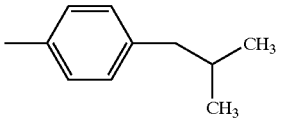 | 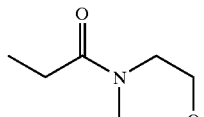 | 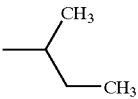 |
| 43 | 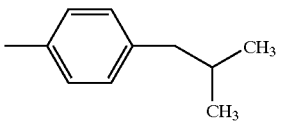 | 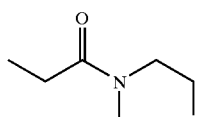 | 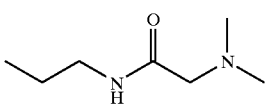 |
| 44 | 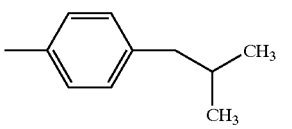 | —CH₃ | 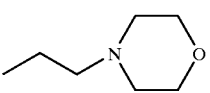 |
| 45 |  | 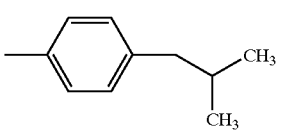 | 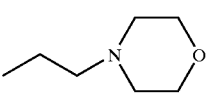 |

TABLE 5-continued

| Example | R₂ | R₃ | R₄ |
|---|---|---|---|
| 46 | propyl-morpholine | sec-butyl (CH(CH₃)CH₂CH₃) | 4-isobutylphenyl |
| 47 | propyl-morpholine | -CH₂CH₂CH₂NHC(O)CH₂N(CH₃)₂ | 4-isobutylphenyl |
| 48 | 3-(2-ethyl)pyridyl | —CH₃ | 4-isobutylphenyl |
| 49 | 3-(2-ethyl)pyridyl | isobutyl (CH₂CH(CH₃)₂) | 4-isobutylphenyl |
| 50 | 3-(2-ethyl)pyridyl | sec-butyl | 4-isobutylphenyl |
| 51 | 3-(2-ethyl)pyridyl | -CH₂CH₂CH₂NHC(O)CH₂N(CH₃)₂ | 4-isobutylphenyl |
| 52 | —CH₃ | —CH₃ | 4-isobutylphenyl |
| 53 | —CH₃ | isobutyl | 4-isobutylphenyl |
| 54 | —CH₃ | sec-butyl | 4-isobutylphenyl |
| 55 | —CH₃ | -CH₂CH₂CH₂NHC(O)CH₂N(CH₃)₂ | 4-isobutylphenyl |

TABLE 5-continued

| Example | R₂ | R₃ | R₄ |
|---------|----|----|----|
| 56 | sec-butyl | —CH₃ | 4-isobutylphenyl |
| 57 | sec-butyl | isopropyl | 4-isobutylphenyl |
| 58 | sec-butyl | isobutyl | 4-isobutylphenyl |
| 59 | sec-butyl | -CH₂C(O)NH-propyl-N(CH₃)₂ (N,N-dimethylglycinamide-N'-propyl) | 4-isobutylphenyl |
| 60 | -CH₂CH₂C(O)-morpholine | —CH₃ | 4-isobutylphenyl |
| 61 | -CH₂CH₂C(O)-morpholine | isopropyl | 4-isobutylphenyl |
| 62 | -CH₂CH₂C(O)-morpholine | isobutyl | 4-isobutylphenyl |
| 63 | -CH₂CH₂C(O)-morpholine | -CH₂C(O)NH-propyl-N(CH₃)₂ | 4-isobutylphenyl |
| 64 | -CH₂CH₂CH₂-morpholine | —CH₃ | 4-hydroxyphenyl |
| 65 | -CH₂CH₂CH₂-morpholine | isopropyl | 4-hydroxyphenyl |

TABLE 5-continued

| Example | R₂ | R₃ | R₄ |
|---|---|---|---|
| 66 | propyl-morpholine | sec-butyl (CH(CH₃)CH₂CH₃) | 4-hydroxyphenyl |
| 67 | propyl-morpholine | -CH₂CH₂CH₂NHC(O)CH₂N(CH₃)₂ | 4-hydroxyphenyl |
| 68 | ethyl-(3-pyridyl) | -CH₃ | 4-hydroxyphenyl |
| 69 | ethyl-(3-pyridyl) | isobutyl (CH₂CH(CH₃)₂) | 4-hydroxyphenyl |
| 70 | ethyl-(3-pyridyl) | sec-butyl (CH(CH₃)CH₂CH₃) | 4-hydroxyphenyl |
| 71 | ethyl-(3-pyridyl) | -CH₂CH₂CH₂NHC(O)CH₂N(CH₃)₂ | 4-hydroxyphenyl |
| 72 | -CH₃ | -CH₃ | 4-hydroxyphenyl |
| 73 | -CH₃ | isobutyl (CH₂CH(CH₃)₂) | 4-hydroxyphenyl |
| 74 | -CH₃ | sec-butyl (CH(CH₃)CH₂CH₃) | 4-hydroxyphenyl |
| 75 | -CH₃ | -CH₂CH₂CH₂NHC(O)CH₂N(CH₃)₂ | 4-hydroxyphenyl |
| 76 | sec-butyl (CH(CH₃)CH₂CH₃) | -CH₃ | 4-hydroxyphenyl |
| 77 | sec-butyl (CH(CH₃)CH₂CH₃) | isobutyl (CH₂CH(CH₃)₂) | 4-hydroxyphenyl |

TABLE 5-continued

| Example | R₂ | R₃ | R₄ |
|---------|----|----|----|
| 78 | sec-butyl (CH(CH₃)CH₂CH₃) | isobutyl (CH₂CH(CH₃)₂) | 4-hydroxyphenyl |
| 79 | sec-butyl | -CH₂C(O)NH-propyl-N(CH₃)₂ | 4-hydroxyphenyl |
| 80 | -CH₂CH₂C(O)-morpholine | -CH₃ | 4-hydroxyphenyl |
| 81 | -CH₂CH₂C(O)-morpholine | isobutyl | 4-hydroxyphenyl |
| 82 | -CH₂CH₂C(O)-morpholine | sec-butyl | 4-hydroxyphenyl |
| 83 | -CH₂CH₂C(O)-morpholine | -CH₂C(O)NH-propyl-N(CH₃)₂ | 4-hydroxyphenyl |
| 84 | -CH₂CH₂CH₂-morpholine | -CH₃ | 4-methylthiazolyl |
| 85 | -CH₂CH₂CH₂-morpholine | isobutyl | 4-methylthiazolyl |
| 86 | -CH₂CH₂CH₂-morpholine | sec-butyl | 4-methylthiazolyl |
| 87 | -CH₂CH₂CH₂-morpholine | -CH₂C(O)NH-propyl-N(CH₃)₂ | 4-methylthiazolyl |

TABLE 5-continued

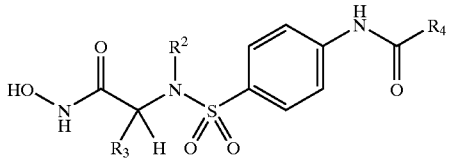

| Example | R₂ | R₃ | R₄ |
|---|---|---|---|
| 88 | 3-ethylpyridine | —CH₃ | 4-methylthiazole |
| 89 | 3-ethylpyridine | isobutyl (CH(CH₃)₂ via CH₂) | 4-methylthiazole |
| 90 | 3-ethylpyridine | sec-butyl | 4-methylthiazole |
| 91 | 3-ethylpyridine | —CH₂CH₂CH₂NHC(O)CH₂N(CH₃)₂ | 4-methylthiazole |
| 92 | —CH₃ | —CH₃ | 4-methylthiazole |
| 93 | —CH₃ | isobutyl | 4-methylthiazole |
| 94 | —CH₃ | sec-butyl | 4-methylthiazole |
| 95 | —CH₃ | —CH₂CH₂CH₂NHC(O)CH₂N(CH₃)₂ | 4-methylthiazole |
| 96 | sec-butyl | —CH₃ | 4-methylthiazole |
| 97 | sec-butyl | isobutyl | 4-methylthiazole |
| 98 | sec-butyl | sec-butyl | 4-methylthiazole |
| 99 | sec-butyl | —CH₂CH₂CH₂NHC(O)CH₂N(CH₃)₂ | 4-methylthiazole |

TABLE 5-continued

| Example | R₂ | R₃ | R₄ |
|---|---|---|---|
| 100 | propionyl-morpholine | —CH₃ | 4-methylthiazole |
| 101 | propionyl-morpholine | isobutyl (H₃C-CH-CH₃) | 4-methylthiazole |
| 102 | propionyl-morpholine | sec-butyl (CH₃-CH-CH₂-CH₃) | 4-methylthiazole |
| 103 | propionyl-morpholine | -CH₂-CH₂-CH₂-NH-C(O)-CH₂-N(CH₃)₂ | 4-methylthiazole |
| 104 | propyl-morpholine | —CH₃ | 3-pyridyl |
| 105 | propyl-morpholine | isobutyl (H₃C-CH-CH₃) | 3-pyridyl |
| 106 | propyl-morpholine | sec-butyl (CH₃-CH-CH₂-CH₃) | 3-pyridyl |
| 107 | propyl-morpholine | -CH₂-CH₂-CH₂-NH-C(O)-CH₂-N(CH₃)₂ | 3-pyridyl |
| 108 | 3-ethylpyridyl | —CH₃ | 3-pyridyl |
| 109 | 3-ethylpyridyl | isobutyl (H₃C-CH-CH₃) | 3-pyridyl |

TABLE 5-continued
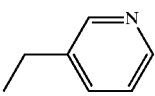
| Example | R₂ | R₃ | R₄ |
|---|---|---|---|
| 110 | 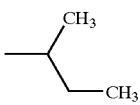 | 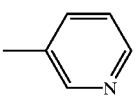 | 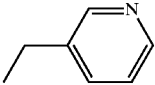 |
| 111 | 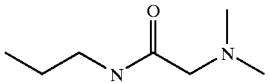 | 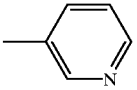 | 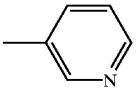 |
| 112 | —CH₃ | —CH₃ | 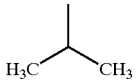 |
| 113 | —CH₃ | 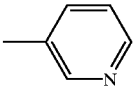 | 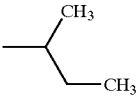 |
| 114 | —CH₃ | 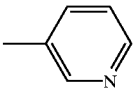 | 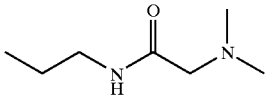 |
| 115 | —CH₃ | 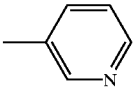 | 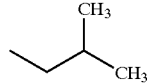 |
| 116 | 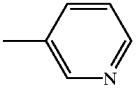 | —CH₃ | 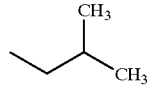 |
| 117 | 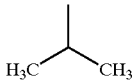 | 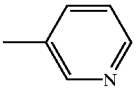 | 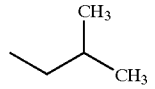 |
| 118 | 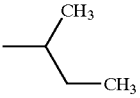 | 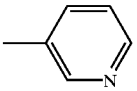 | 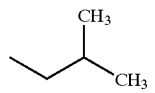 |
| 119 | 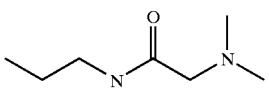 | 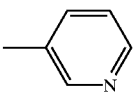 | 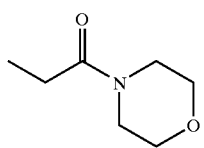 |
| 120 | 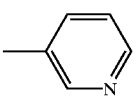 | —CH₃ |  |

TABLE 5-continued
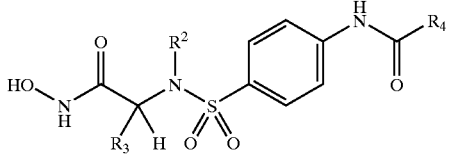
| Example | R₂ | R₃ | R₄ |
|---|---|---|---|
| 121 | 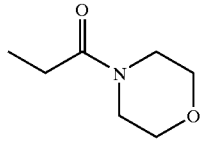 | 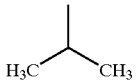 | 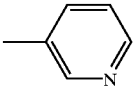 |
| 122 | 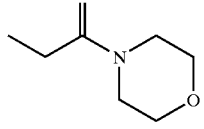 | 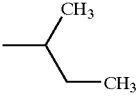 | 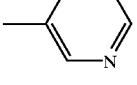 |
| 123 | 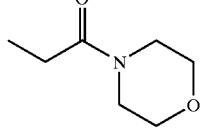 | 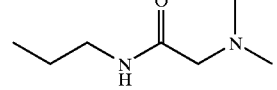 | 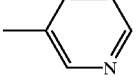 |
| 124 | 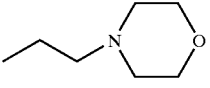 | —CH₃ | 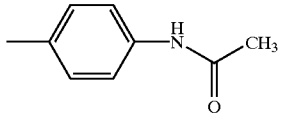 |
| 125 | 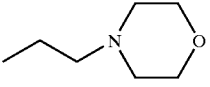 |  | 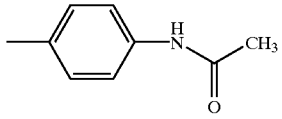 |
| 126 | 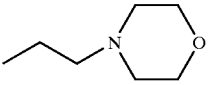 | 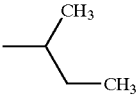 | 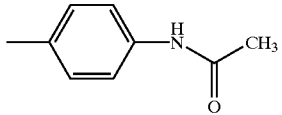 |
| 127 | 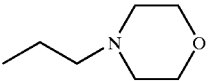 | 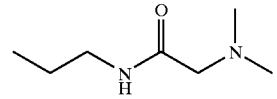 | 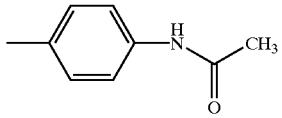 |
| 128 | 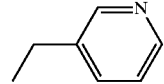 | —CH₃ | 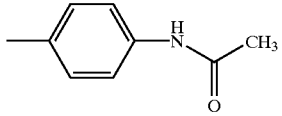 |
| 129 | 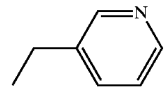 | 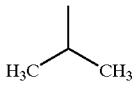 | 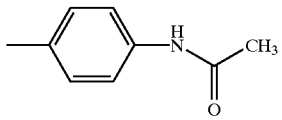 |

TABLE 5-continued

| Example | R₂ | R₃ | R₄ |
| --- | --- | --- | --- |
| 130 | 3-pyridyl-ethyl | isobutyl | 4-(acetylamino)phenyl |
| 131 | 3-pyridyl-ethyl | -CH₂C(O)NH-propyl-N(CH₃)₂ side chain | 4-(acetylamino)phenyl |
| 132 | —CH₃ | —CH₃ | 4-(acetylamino)phenyl |
| 133 | —CH₃ | isobutyl | 4-(acetylamino)phenyl |
| 134 | —CH₃ | sec-butyl | 4-(acetylamino)phenyl |
| 135 | —CH₃ | -CH₂C(O)NH-propyl-N(CH₃)₂ | 4-(acetylamino)phenyl |
| 136 | sec-butyl | —CH₃ | 4-(acetylamino)phenyl |
| 137 | sec-butyl | isobutyl | 4-(acetylamino)phenyl |
| 138 | sec-butyl | sec-butyl | 4-(acetylamino)phenyl |
| 139 | sec-butyl | -CH₂C(O)NH-propyl-N(CH₃)₂ | 4-(acetylamino)phenyl |

TABLE 5-continued
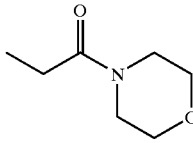
| Example | R₂ | R₃ | R₄ |
|---|---|---|---|
| 140 | 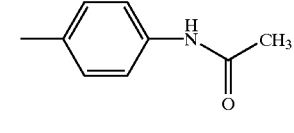 | —CH₃ | 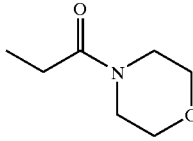 |
| 141 | 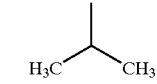 | 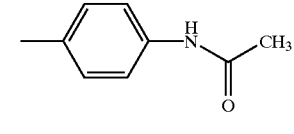 | 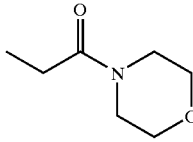 |
| 142 | 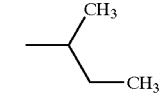 | 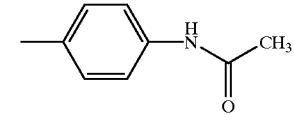 | 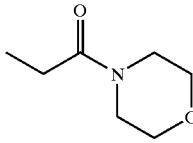 |
| 143 | 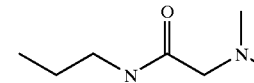 | 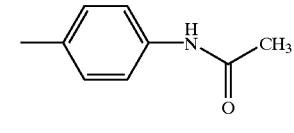 | 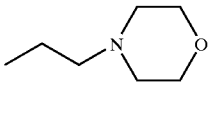 |
| 144 | 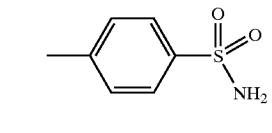 | —CH₃ | 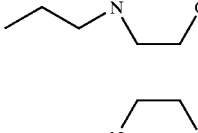 |
| 145 | 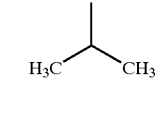 | 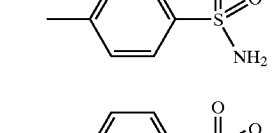 | 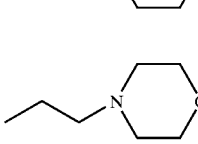 |
| 146 | 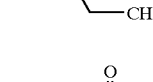 | 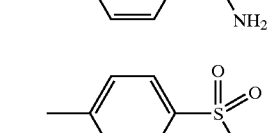 | 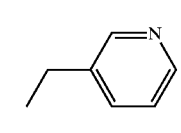 |
| 147 | 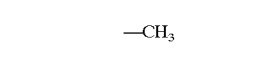 | 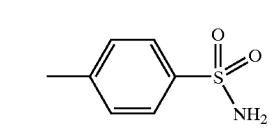 | 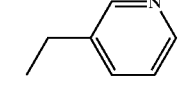 |
| 148 |  | —CH₃ |  |
| 149 |  |  | |

TABLE 5-continued
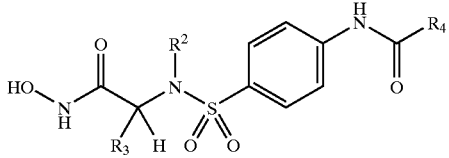
| Example | R₂ | R₃ | R₄ |
|---|---|---|---|
| 150 | 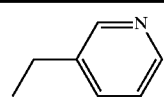 | 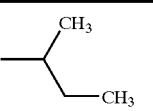 | 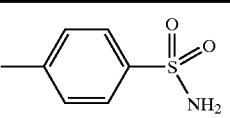 |
| 151 | 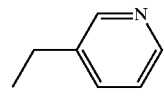 | 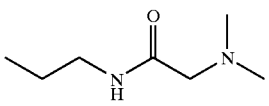 | 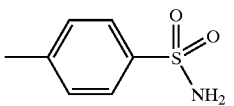 |
| 152 | —CH₃ | —CH₃ | 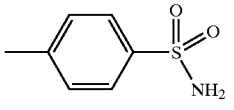 |
| 153 | —CH₃ | 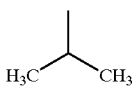 | 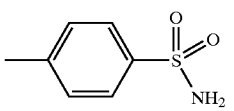 |
| 154 | —CH₃ | 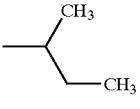 | 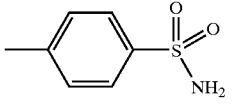 |
| 155 | —CH₃ | 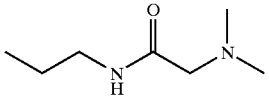 | 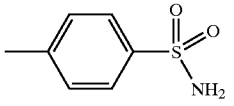 |
| 156 | 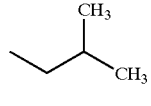 | —CH₃ | 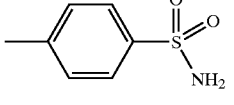 |
| 157 | 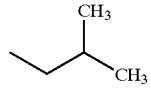 | 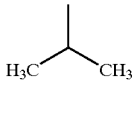 | 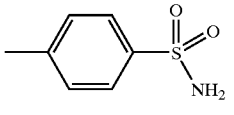 |
| 158 | 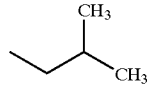 | 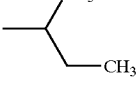 | 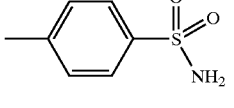 |
| 159 | 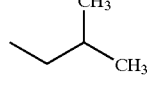 | 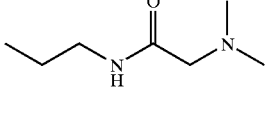 | 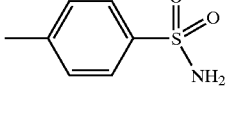 |
| 160 | 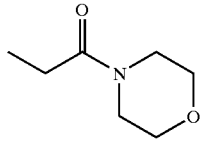 | —CH₃ | 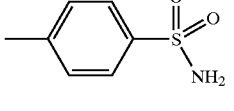 |

TABLE 5-continued

| Example | R₂ | R₃ | R₄ |
|---|---|---|---|
| 161 | propionyl-morpholine | isobutyl | 4-sulfamoylphenyl |
| 162 | propionyl-morpholine | sec-butyl | 4-sulfamoylphenyl |
| 163 | propionyl-morpholine | -CH₂CH₂CH₂NHC(O)CH₂N(CH₃)₂ | 4-sulfamoylphenyl |
| 164 | 2-morpholinoethyl | -CH₃ | 4-methylphenyl |
| 165 | 2-morpholinoethyl | isobutyl | 4-methylphenyl |
| 166 | 2-morpholinoethyl | sec-butyl | 4-methylphenyl |
| 167 | 2-morpholinoethyl | -CH₂CH₂CH₂NHC(O)CH₂N(CH₃)₂ | 4-methylphenyl |
| 168 | 2-(pyridin-3-yl)ethyl | -CH₃ | 4-methylphenyl |
| 169 | 2-(pyridin-3-yl)ethyl | isobutyl | 4-methylphenyl |
| 170 | 2-(pyridin-3-yl)ethyl | sec-butyl | 4-methylphenyl |
| 171 | 2-(pyridin-3-yl)ethyl | -CH₂CH₂CH₂NHC(O)CH₂N(CH₃)₂ | 4-methylphenyl |

TABLE 5-continued

| Example | R₂ | R₃ | R₄ |
| --- | --- | --- | --- |
| 172 | —CH₃ | —CH₃ | -C₆H₄-CH₃ (para) |
| 173 | —CH₃ | —CH₂CH(CH₃)₂ (isobutyl) | -C₆H₄-CH₃ (para) |
| 174 | —CH₃ | —CH(CH₃)CH₂CH₃ (sec-butyl) | -C₆H₄-CH₃ (para) |
| 175 | —CH₃ | —C(=O)NH-propyl-CH₂-N(CH₃)₂ | -C₆H₄-CH₃ (para) |
| 176 | —CH(CH₃)CH₂CH₃ (sec-butyl) | —CH₃ | -C₆H₄-CH₃ (para) |
| 177 | —CH(CH₃)CH₂CH₃ (sec-butyl) | —CH₂CH(CH₃)₂ (isobutyl) | -C₆H₄-CH₃ (para) |
| 178 | —CH(CH₃)CH₂CH₃ (sec-butyl) | —CH(CH₃)CH₂CH₃ (sec-butyl) | -C₆H₄-CH₃ (para) |
| 179 | —CH(CH₃)CH₂CH₃ (sec-butyl) | —C(=O)NH-propyl-CH₂-N(CH₃)₂ | -C₆H₄-CH₃ (para) |
| 180 | —CH₂C(=O)-morpholinyl | —CH₃ | -C₆H₄-CH₃ (para) |
| 181 | —CH₂C(=O)-morpholinyl | —CH₂CH(CH₃)₂ (isobutyl) | -C₆H₄-CH₃ (para) |
| 182 | —CH₂C(=O)-morpholinyl | —CH(CH₃)CH₂CH₃ (sec-butyl) | -C₆H₄-CH₃ (para) |

TABLE 5-continued

| Example | R₂ | R₃ | R₄ |
| --- | --- | --- | --- |
| 183 | propionyl-morpholine | -CH₂CH₂CH₂-NH-C(O)-CH₂-N(CH₃)₂ | 4-methylphenyl |
| 184 | propyl-morpholine | —CH₃ | 2-thienyl |
| 185 | propyl-morpholine | isobutyl (CH₂CH(CH₃)₂) | 2-thienyl |
| 186 | propyl-morpholine | sec-butyl (CH(CH₃)CH₂CH₃) | 2-thienyl |
| 187 | propyl-morpholine | -CH₂CH₂CH₂-NH-C(O)-CH₂-N(CH₃)₂ | 2-thienyl |
| 188 | ethyl-3-pyridyl | —CH₃ | 2-thienyl |
| 189 | ethyl-3-pyridyl | isobutyl | 2-thienyl |
| 190 | ethyl-3-pyridyl | sec-butyl | 2-thienyl |
| 191 | ethyl-3-pyridyl | -CH₂CH₂CH₂-NH-C(O)-CH₂-N(CH₃)₂ | 2-thienyl |
| 192 | —CH₃ | —CH₃ | 2-thienyl |
| 193 | —CH₃ | isobutyl | 2-thienyl |
| 194 | —CH₃ | sec-butyl | 2-thienyl |

TABLE 5-continued
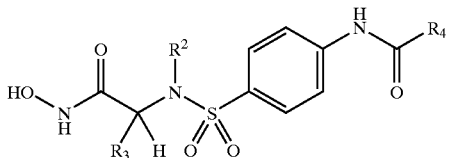
| Example | R₂ | R₃ | R₄ |
|---|---|---|---|
| 195 | —CH₃ | 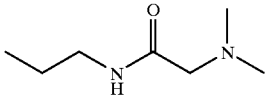 | 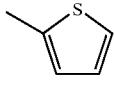 |
| 196 | 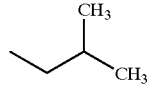 | —CH₃ | 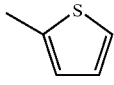 |
| 197 | 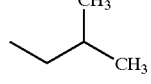 | 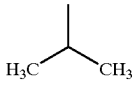 | 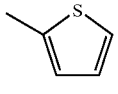 |
| 198 | 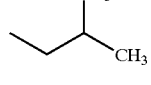 | 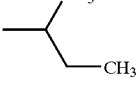 | 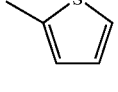 |
| 199 | 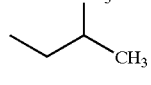 | 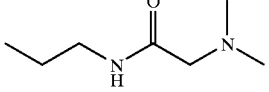 | 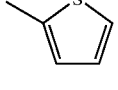 |
| 200 | 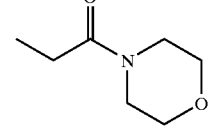 | —CH₃ | 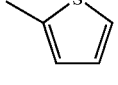 |
| 201 | 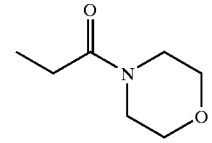 | 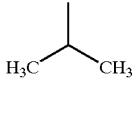 | 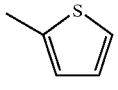 |
| 202 | 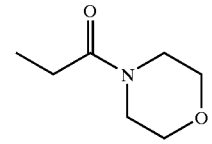 | 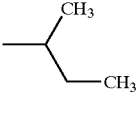 | 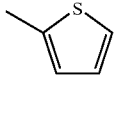 |
| 203 | 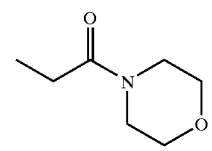 | 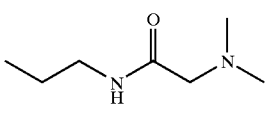 | 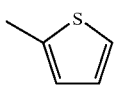 |
| 204 | 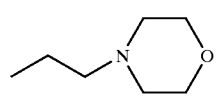 | —CH₃ | 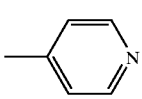 |

TABLE 5-continued

| Example | R₂ | R₃ | R₄ |
| --- | --- | --- | --- |
| 205 | propyl-morpholine | isobutyl (CH(CH₃)₂CH-) H₃C-CH-CH₃ | 4-pyridyl |
| 206 | propyl-morpholine | sec-butyl (CH₃CH(CH₃)CH₂-) | 4-pyridyl |
| 207 | propyl-morpholine | -CH₂CH₂CH₂-NH-C(O)-CH₂-N(CH₃)₂ | 4-pyridyl |
| 208 | 3-pyridyl-ethyl | -CH₃ | 4-pyridyl |
| 209 | 3-pyridyl-ethyl | isobutyl | 4-pyridyl |
| 210 | 3-pyridyl-ethyl | sec-butyl | 4-pyridyl |
| 211 | 3-pyridyl-ethyl | -CH₂CH₂CH₂-NH-C(O)-CH₂-N(CH₃)₂ | 4-pyridyl |
| 212 | —CH₃ | —CH₃ | 4-pyridyl |
| 213 | —CH₃ | isobutyl | 4-pyridyl |
| 214 | —CH₃ | sec-butyl | 4-pyridyl |
| 215 | —CH₃ | -CH₂CH₂CH₂-NH-C(O)-CH₂-N(CH₃)₂ | 4-pyridyl |
| 216 | sec-butyl | —CH₃ | 4-pyridyl |

TABLE 5-continued

| Example | R₂ | R₃ | R₄ |
|---------|----|----|----|
| 217 | sec-butyl (CH(CH₃)CH₂CH₃) | isobutyl (CH₂CH(CH₃)₂) | 4-pyridyl |
| 218 | sec-butyl | isobutyl (CH(CH₃)CH₂CH₃) | 4-pyridyl |
| 219 | isobutyl | —CH₂C(O)NH-propyl-N(CH₃)₂ (propyl amide with dimethylaminomethyl) | 4-pyridyl |
| 220 | —CH₂C(O)-morpholine | —CH₃ | 4-pyridyl |
| 221 | —CH₂C(O)-morpholine | isobutyl (CH₂CH(CH₃)₂) | 4-pyridyl |
| 222 | —CH₂C(O)-morpholine | sec-butyl | 4-pyridyl |
| 223 | —CH₂C(O)-morpholine | —CH₂C(O)NH-propyl-N(CH₃)₂ | 4-pyridyl |
| 224 | —(CH₂)₃-morpholine | —CH₃ | 4-isopropylphenyl |
| 225 | —(CH₂)₃-morpholine | isobutyl (CH₂CH(CH₃)₂) | 4-isopropylphenyl |
| 226 | —(CH₂)₃-morpholine | sec-butyl | 4-isopropylphenyl |

TABLE 5-continued
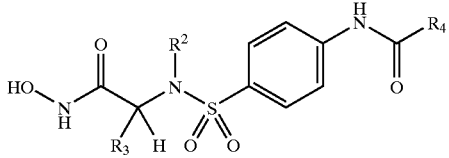
| Example | R₂ | R₃ | R₄ |
|---|---|---|---|
| 227 | 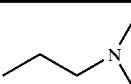 | 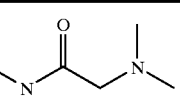 | 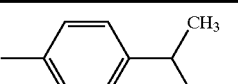 |
| 228 | 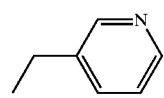 | —CH₃ | 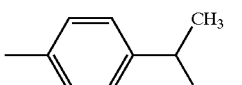 |
| 229 | 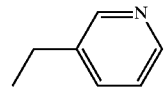 | 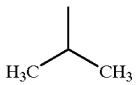 | 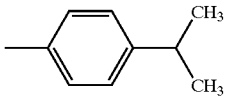 |
| 230 | 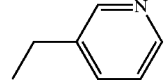 | 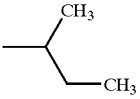 | 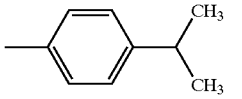 |
| 231 | 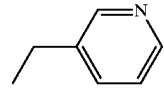 | 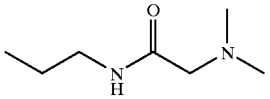 | 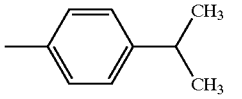 |
| 232 | —CH₃ | —CH₃ | 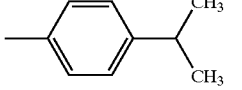 |
| 233 | —CH₃ | 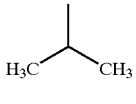 | 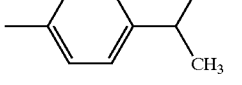 |
| 234 | —CH₃ | 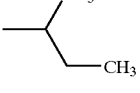 | 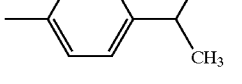 |
| 235 | —CH₃ | 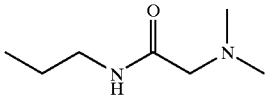 | 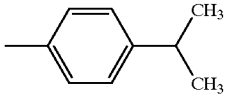 |
| 236 | 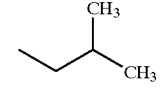 | —CH₃ | 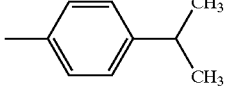 |
| 237 | 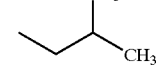 | 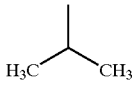 | 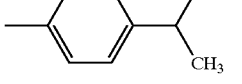 |
| 238 | 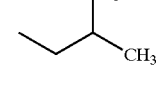 | 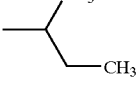 | 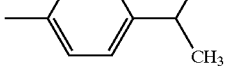 |

TABLE 5-continued
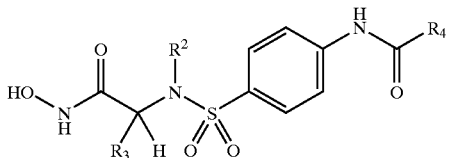
| Example | R₂ | R₃ | R₄ |
|---|---|---|---|
| 239 | 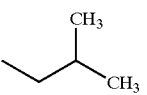 | 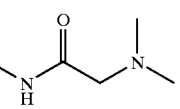 | 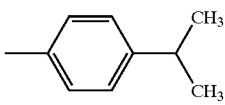 |
| 240 | 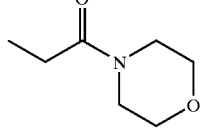 | —CH₃ | 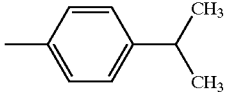 |
| 241 | 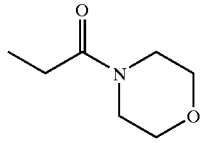 | 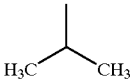 | 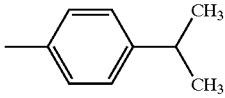 |
| 242 | 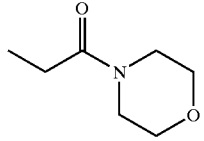 | 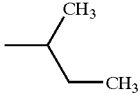 | 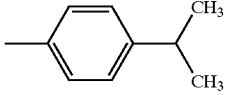 |
| 243 | 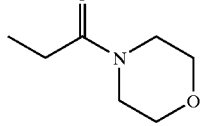 | 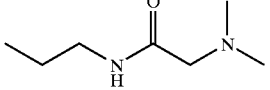 | 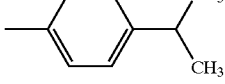 |
| 244 | 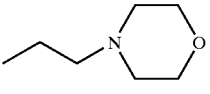 | —CH₃ | 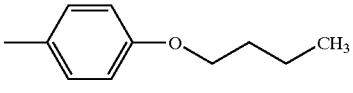 |
| 245 | 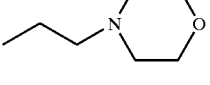 | 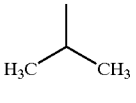 | 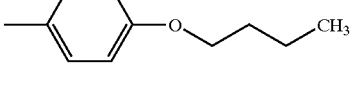 |
| 246 | 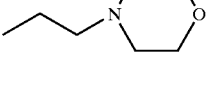 | 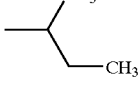 | 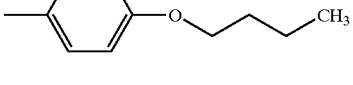 |
| 247 | 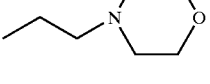 | 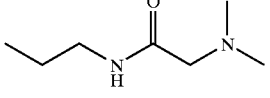 | 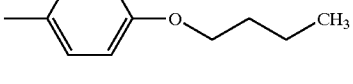 |
| 248 | 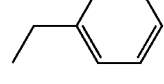 | —CH₃ | 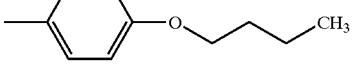 |

TABLE 5-continued

| Example | R₂ | R₃ | R₄ |
|---------|----|----|----|
| 249 | 3-ethylpyridine | isobutyl (H₃C-CH-CH₃, CH₂) | 4-(butoxy)phenyl |
| 250 | 3-ethylpyridine | sec-butyl (CH₃, CH-CH₂-CH₃) | 4-(butoxy)phenyl |
| 251 | 3-ethylpyridine | -CH₂CH₂CH₂-NH-C(=O)-CH₂-N(CH₃)₂ | 4-(butoxy)phenyl |
| 252 | —CH₃ | —CH₃ | 4-(butoxy)phenyl |
| 253 | —CH₃ | isobutyl (H₃C-CH-CH₃, CH₂) | 4-(butoxy)phenyl |
| 254 | —CH₃ | sec-butyl (CH₃, CH-CH₂-CH₃) | 4-(butoxy)phenyl |
| 255 | —CH₃ | -CH₂CH₂CH₂-NH-C(=O)-CH₂-N(CH₃)₂ | 4-(butoxy)phenyl |
| 256 | sec-butyl (CH₃, CH-CH₂-CH₃) | —CH₃ | 4-(butoxy)phenyl |
| 257 | sec-butyl (CH₃, CH-CH₂-CH₃) | isobutyl (H₃C-CH-CH₃, CH₂) | 4-(butoxy)phenyl |
| 258 | sec-butyl (CH₃, CH-CH₂-CH₃) | sec-butyl (CH₃, CH-CH₂-CH₃) | 4-(butoxy)phenyl |
| 259 | sec-butyl (CH₃, CH-CH₂-CH₃) | -CH₂CH₂CH₂-NH-C(=O)-CH₂-N(CH₃)₂ | 4-(butoxy)phenyl |
| 260 | -CH₂CH₂-C(=O)-morpholinyl | —CH₃ | 4-(butoxy)phenyl |

TABLE 5-continued

| Example | R₂ | R₃ | R₄ |
|---|---|---|---|
| 261 | propionyl-morpholine | isobutyl (H₃C-CH(CH₃)-) | 4-(butoxy)phenyl |
| 262 | propionyl-morpholine | sec-butyl | 4-(butoxy)phenyl |
| 263 | propionyl-morpholine | -CH₂CH₂CH₂-NH-C(O)-CH₂-N(CH₃)₂ | 4-(butoxy)phenyl |
| 264 | propyl-morpholine | —CH₃ | 4-(methoxycarbonyl)phenyl |
| 265 | propyl-morpholine | isobutyl | 4-(methoxycarbonyl)phenyl |
| 266 | propyl-morpholine | sec-butyl | 4-(methoxycarbonyl)phenyl |
| 267 | propyl-morpholine | -CH₂CH₂CH₂-NH-C(O)-CH₂-N(CH₃)₂ | 4-(methoxycarbonyl)phenyl |
| 268 | 3-(ethyl)pyridine | —CH₃ | 4-(methoxycarbonyl)phenyl |
| 269 | 3-(ethyl)pyridine | isobutyl | 4-(methoxycarbonyl)phenyl |
| 270 | 3-(ethyl)pyridine | sec-butyl | 4-(methoxycarbonyl)phenyl |

TABLE 5-continued

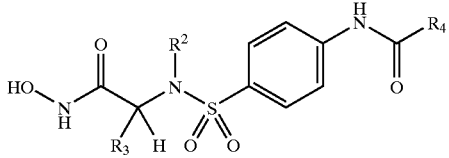

| Example | R₂ | R₃ | R₄ |
|---|---|---|---|
| 271 | 3-ethylpyridine | —CH₂CH₂CH₂NHC(O)CH₂N(CH₃)₂ | 4-(methoxycarbonyl)phenyl |
| 272 | —CH₃ | —CH₃ | 4-(methoxycarbonyl)phenyl |
| 273 | —CH₃ | —CH₂CH(CH₃)₂ | 4-(methoxycarbonyl)phenyl |
| 274 | —CH₃ | —CH(CH₃)CH₂CH₃ | 4-(methoxycarbonyl)phenyl |
| 275 | —CH₃ | —CH₂CH₂CH₂NHC(O)CH₂N(CH₃)₂ | 4-(methoxycarbonyl)phenyl |
| 276 | —CH(CH₃)CH₂CH₃ | —CH₃ | 4-(methoxycarbonyl)phenyl |
| 277 | —CH(CH₃)CH₂CH₃ | —CH₂CH(CH₃)₂ | 4-(methoxycarbonyl)phenyl |
| 278 | —CH(CH₃)CH₂CH₃ | —CH(CH₃)CH₂CH₃ | 4-(methoxycarbonyl)phenyl |
| 279 | —CH(CH₃)CH₂CH₃ | —CH₂CH₂CH₂NHC(O)CH₂N(CH₃)₂ | 4-(methoxycarbonyl)phenyl |
| 280 | —CH₂C(O)-morpholinyl | —CH₃ | 4-(methoxycarbonyl)phenyl |
| 281 | —CH₂C(O)-morpholinyl | —CH₂CH(CH₃)₂ | 4-(methoxycarbonyl)phenyl |

TABLE 5-continued

| Example | R₂ | R₃ | R₄ |
|---------|-----|-----|-----|
| 282 | propionyl-morpholine | isobutyl (sec-butyl, -CH(CH₃)CH₂CH₃) | 4-(methoxycarbonyl)phenyl |
| 283 | propionyl-morpholine | -CH₂CH₂CH₂NHC(O)CH₂N(CH₃)₂ | 4-isopropylphenyl |
| 284 | propyl-morpholine | —CH₃ | 4-isopropoxyphenyl |
| 285 | propyl-morpholine | isobutyl (-CH₂CH(CH₃)₂) | 4-isopropoxyphenyl |
| 286 | propyl-morpholine | sec-butyl (-CH(CH₃)CH₂CH₃) | 4-isopropoxyphenyl |
| 287 | propyl-morpholine | -CH₂CH₂CH₂NHC(O)CH₂N(CH₃)₂ | 4-isopropoxyphenyl |
| 288 | 2-(pyridin-3-yl)ethyl | —CH₃ | 4-isopropoxyphenyl |
| 289 | 2-(pyridin-3-yl)ethyl | isobutyl (-CH₂CH(CH₃)₂) | 4-isopropoxyphenyl |
| 290 | 2-(pyridin-3-yl)ethyl | sec-butyl (-CH(CH₃)CH₂CH₃) | 4-isopropoxyphenyl |

TABLE 5-continued

| Example | R₂ | R₃ | R₄ |
|---|---|---|---|
| 291 | 3-ethylpyridine | propyl-NH-C(O)-CH₂-N(CH₃)₂ | 4-isopropoxyphenyl |
| 292 | —CH₃ | —CH₃ | 4-isopropoxyphenyl |
| 293 | —CH₃ | isobutyl (CH₂CH(CH₃)₂) | 4-isopropoxyphenyl |
| 294 | —CH₃ | sec-butyl (CH(CH₃)CH₂CH₃) | 4-isopropoxyphenyl |
| 295 | —CH₃ | propyl-NH-C(O)-CH₂-N(CH₃)₂ | 4-isopropoxyphenyl |
| 296 | sec-butyl | —CH₃ | 4-isopropoxyphenyl |
| 297 | sec-butyl | isobutyl | 4-isopropoxyphenyl |
| 298 | sec-butyl | sec-butyl | 4-isopropoxyphenyl |
| 299 | sec-butyl | propyl-NH-C(O)-CH₂-N(CH₃)₂ | 4-isopropoxyphenyl |
| 300 | -CH₂CH₂-C(O)-morpholine | —CH₃ | 4-isopropoxyphenyl |

TABLE 5-continued

| Example | R₂ | R₃ | R₄ |
|---|---|---|---|
| 301 | propionyl-morpholine | isobutyl | 4-isopropoxyphenyl |
| 302 | propionyl-morpholine | sec-butyl | 4-isopropoxyphenyl |
| 303 | propionyl-morpholine | -CH₂C(O)NHCH₂CH₂CH₂-N(CH₃)₂ | 4-isopropoxyphenyl |

TABLE 6

| Example | R² | R³ | R⁴ |
|---|---|---|---|
| 304 | propyl-morpholine | —CH₃ | benzyl |
| 305 | propyl-morpholine | isobutyl | benzyl |
| 306 | propyl-morpholine | sec-butyl | benzyl |
| 307 | propyl-morpholine | -CH₂C(O)NHCH₂CH₂CH₂-N(CH₃)₂ | benzyl |
| 308 | ethyl-pyridin-3-yl | —CH₃ | benzyl |

TABLE 6-continued
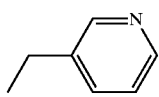
| Example | R² | R³ | R⁴ |
|---|---|---|---|
| 309 | 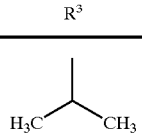 | 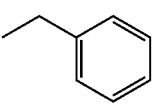 | 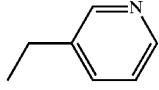 |
| 310 | 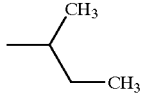 | 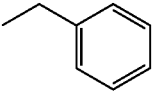 | 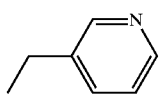 |
| 311 | 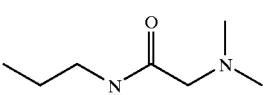 | 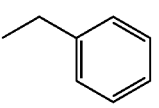 | 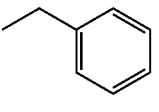 |
| 312 | —CH₃ | —CH₃ | 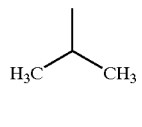 |
| 313 | —CH₃ | 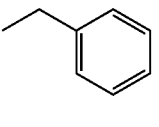 | 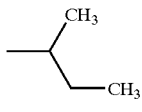 |
| 314 | —CH₃ | 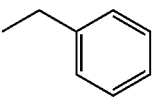 | 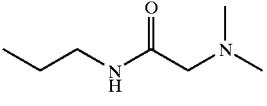 |
| 315 | —CH₃ | 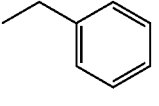 | 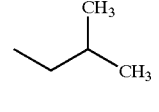 |
| 316 | 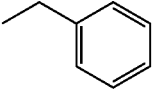 | —CH₃ | 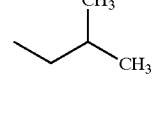 |
| 317 | 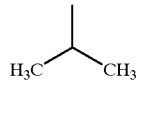 | 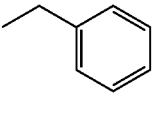 | 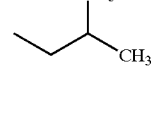 |
| 318 | 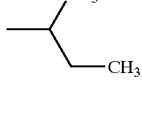 | 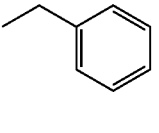 | 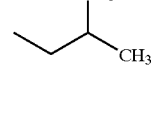 |
| 319 | 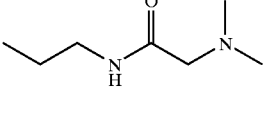 | 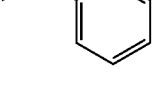 |  |

TABLE 6-continued
| Example | R² | R³ | R⁴ |
|---|---|---|---|
| 320 | 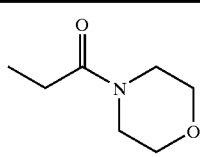 | —CH₃ |  |
| 321 | 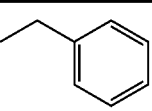 | 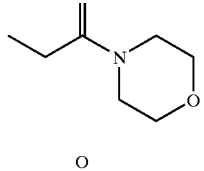 | 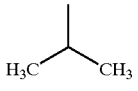 |
| 322 | 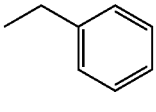 | 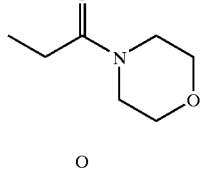 | 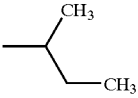 |
| 323 | 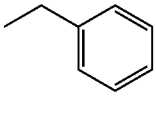 | 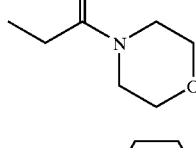 | 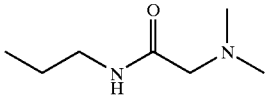 |
| 324 | 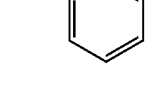 | —CH₃ | 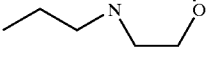 |
| 325 |  | 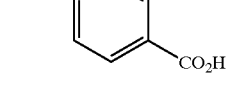 | 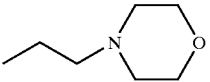 |
| 326 | 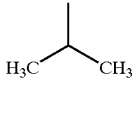 | 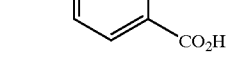 | 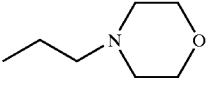 |
| 327 | 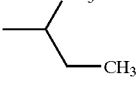 | 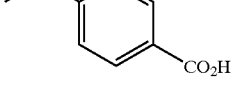 | 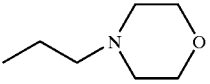 |
| 328 | 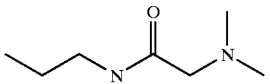 | —CH₃ | 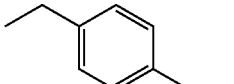 |
| 329 | 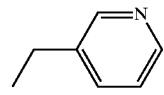 |  | 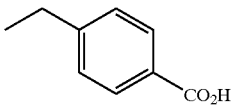 |

TABLE 6-continued

| Example | R² | R³ | R⁴ |
|---|---|---|---|
| 330 | 3-pyridyl-ethyl | sec-butyl (CH(CH₃)CH₂CH₃) | 4-(CO₂H)-phenyl-ethyl |
| 331 | 3-pyridyl-ethyl | -CH₂C(O)NH-propyl-N(CH₃)₂ variant (propyl-NH-C(O)-CH₂-N(CH₃)₂) | 4-(CO₂H)-phenyl-ethyl |
| 332 | —CH₃ | —CH₃ | 4-(CO₂H)-phenyl-ethyl |
| 333 | —CH₃ | isobutyl (CH₂CH(CH₃)₂) | 4-(CO₂H)-phenyl-ethyl |
| 334 | —CH₃ | sec-butyl | 4-(CO₂H)-phenyl-ethyl |
| 335 | —CH₃ | propyl-NH-C(O)-CH₂-N(CH₃)₂ | 4-(CO₂H)-phenyl-ethyl |
| 336 | sec-butyl | —CH₃ | 4-(CO₂H)-phenyl-ethyl |
| 337 | sec-butyl | isobutyl | 4-(CO₂H)-phenyl-ethyl |
| 338 | sec-butyl | sec-butyl | 4-(CO₂H)-phenyl-ethyl |
| 339 | sec-butyl | propyl-NH-C(O)-CH₂-N(CH₃)₂ | 4-(CO₂H)-phenyl-ethyl |
| 340 | -CH₂C(O)-morpholinyl | —CH₃ | 4-(CO₂H)-phenyl-ethyl |

TABLE 6-continued

| Example | R² | R³ | R⁴ |
|---|---|---|---|
| 341 | 1-(propanoyl)morpholine | isobutyl | 4-ethylbenzoic acid |
| 342 | 1-(propanoyl)morpholine | sec-butyl | 4-ethylbenzoic acid |
| 343 | 1-(propanoyl)morpholine | N-propyl-2-(dimethylamino)acetamide | 4-ethylbenzoic acid |
| 344 | 4-propylmorpholine | —CH₃ | 4-propylmorpholine |
| 345 | 4-propylmorpholine | isobutyl | 4-propylmorpholine |
| 346 | 4-propylmorpholine | sec-butyl | 4-propylmorpholine |
| 347 | 4-propylmorpholine | N-propyl-2-(dimethylamino)acetamide | 4-propylmorpholine |
| 348 | 3-ethylpyridine | —CH₃ | 4-propylmorpholine |
| 349 | 3-ethylpyridine | isobutyl | 4-propylmorpholine |
| 350 | 3-ethylpyridine | sec-butyl | 4-propylmorpholine |
| 351 | 3-ethylpyridine | N-propyl-2-(dimethylamino)acetamide | 4-propylmorpholine |

TABLE 6-continued
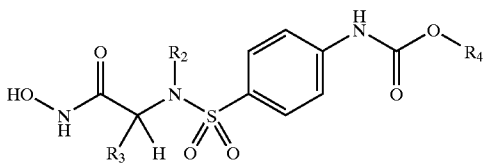
| Example | R² | R³ | R⁴ |
|---|---|---|---|
| 352 | —CH₃ | —CH₃ | 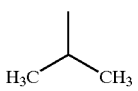 |
| 353 | —CH₃ | 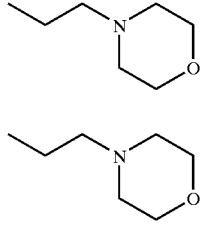 | 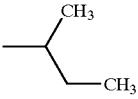 |
| 354 | —CH₃ | 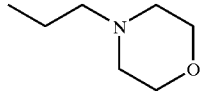 | 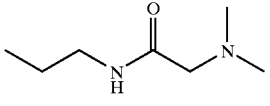 |
| 355 | —CH₃ | 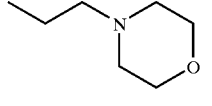 | 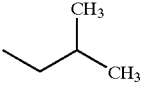 |
| 356 | 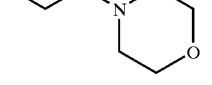 | —CH₃ | 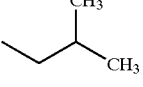 |
| 357 | 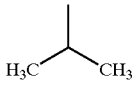 | 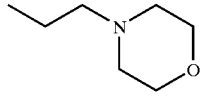 | 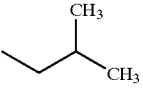 |
| 358 | 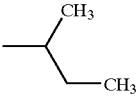 | 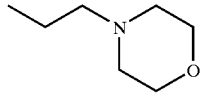 | 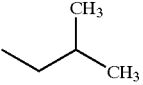 |
| 359 | 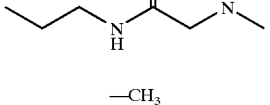 | 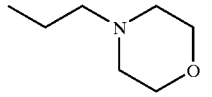 |  |
| 360 | 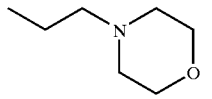 | —CH₃ | 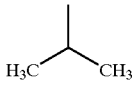 |
| 361 | 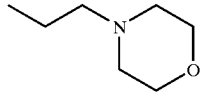 | H₃C CH₃ | |

TABLE 6-continued

| Example | R² | R³ | R⁴ |
|---|---|---|---|
| 362 | propionyl-morpholine | sec-butyl (CH(CH₃)CH₂CH₃) | propyl-morpholine |
| 363 | propionyl-morpholine | -CH₂CH₂CH₂NHC(O)CH₂N(CH₃)₂ | propyl-morpholine |
| 364 | propyl-morpholine | -CH₃ | 4-methoxybenzyl (-CH₂-C₆H₄-OCH₃) |
| 365 | propyl-morpholine | isobutyl (CH₂CH(CH₃)₂) | 4-methoxybenzyl |
| 366 | propyl-morpholine | sec-butyl | 4-methoxybenzyl |
| 367 | propyl-morpholine | -CH₂CH₂CH₂NHC(O)CH₂N(CH₃)₂ | 4-methoxybenzyl |
| 368 | 3-(pyridin-3-yl)ethyl | -CH₃ | 4-methoxybenzyl |
| 369 | 3-(pyridin-3-yl)ethyl | isobutyl | 4-methoxybenzyl |

TABLE 6-continued

| Example | R² | R³ | R⁴ |
|---------|-----|-----|-----|
| 370 | 3-ethylpyridine | isobutyl (CH(CH₃)CH₂CH₃) | 4-ethyl-methoxybenzene |
| 371 | 3-ethylpyridine | -CH₂C(O)NHCH₂CH₂CH₃ with N(CH₃)₂ | 4-ethyl-methoxybenzene |
| 372 | —CH₃ | —CH₃ | 4-ethyl-methoxybenzene |
| 373 | —CH₃ | isobutyl ((CH₃)₂CHCH₂—) | 4-ethyl-methoxybenzene |
| 374 | —CH₃ | isobutyl (—CH(CH₃)CH₂CH₃) | 4-ethyl-methoxybenzene |
| 375 | —CH₃ | -CH₂C(O)NHCH₂CH₂CH₃ with N(CH₃)₂ | 4-ethyl-methoxybenzene |
| 376 | sec-butyl | —CH₃ | 4-ethyl-methoxybenzene |
| 377 | sec-butyl | isobutyl | 4-ethyl-methoxybenzene |

TABLE 6-continued
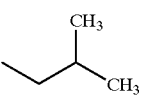
| Example | R² | R³ | R⁴ |
|---|---|---|---|
| 378 | 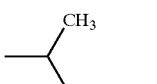 | 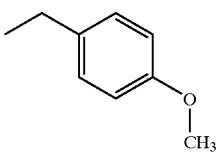 | 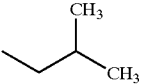 |
| 379 | 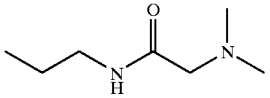 | 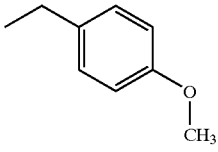 | 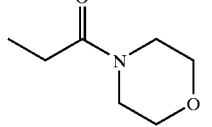 |
| 380 | 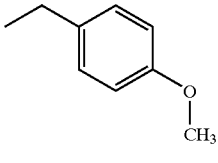 | —CH₃ | 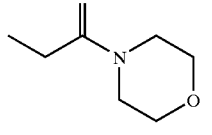 |
| 381 | 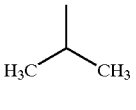 | 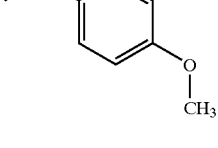 | 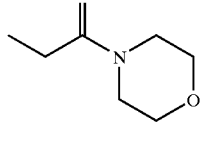 |
| 382 | 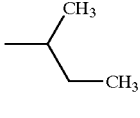 | 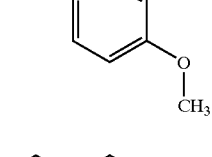 | 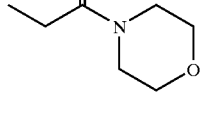 |
| 383 | 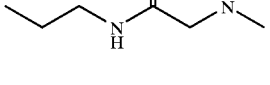 | 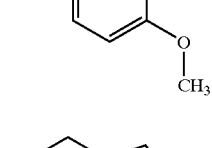 | 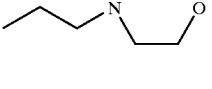 |
| 384 | 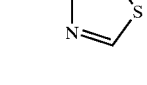 | —CH₃ | 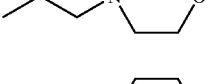 |
| 385 | 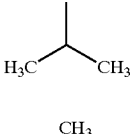 | 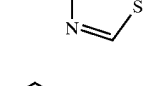 | 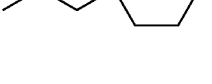 |
| 386 | 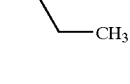 | 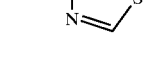 | |

TABLE 6-continued
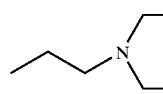
| Example | R² | R³ | R⁴ |
|---|---|---|---|
| 387 | 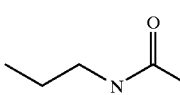 | 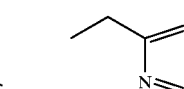 | 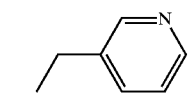 |
| 388 | 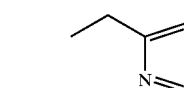 | —CH₃ | 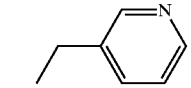 |
| 389 | 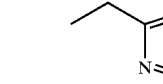 | 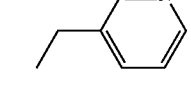 | 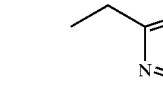 |
| 390 | 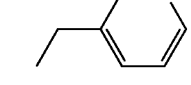 | 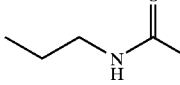 | 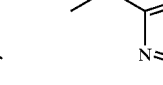 |
| 391 |  |  |  |
| 392 | —CH₃ | —CH₃ | 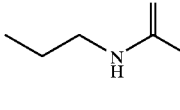 |
| 393 | —CH₃ |  | 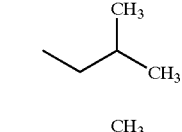 |
| 394 | —CH₃ |  | 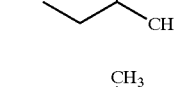 |
| 395 | —CH₃ | 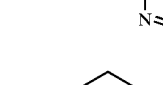 | 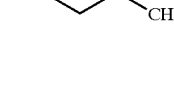 |
| 396 |  | —CH₃ |  |
| 397 |  |  |  |
| 398 |  |  |  |

TABLE 6-continued

| Example | R² | R³ | R⁴ |
|---------|----|----|----|
| 399 | sec-butyl | propyl-NH-C(O)-CH₂-N(CH₃)₂ | 4-ethylthiazole |
| 400 | propanoyl-morpholine | —CH₃ | 4-ethylthiazole |
| 401 | propanoyl-morpholine | isobutyl | 4-ethylthiazole |
| 402 | propanoyl-morpholine | isobutyl | 4-ethylthiazole |
| 403 | propanoyl-morpholine | propyl-NH-C(O)-CH₂-N(CH₃)₂ | 4-ethylthiazole |
| 404 | propyl-morpholine | —CH₃ | 4-ethylpyridine |
| 405 | propyl-morpholine | isobutyl | 4-ethylpyridine |
| 406 | propyl-morpholine | isobutyl | 4-ethylpyridine |
| 407 | propyl-morpholine | propyl-NH-C(O)-CH₂-N(CH₃)₂ | 4-ethylpyridine |
| 408 | 3-ethylpyridine | —CH₃ | 4-ethylpyridine |

TABLE 6-continued

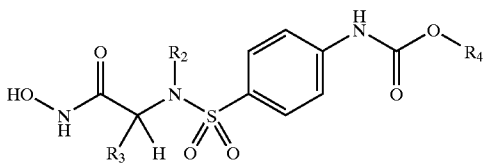

| Example | R² | R³ | R⁴ |
|---|---|---|---|
| 409 | 3-ethylpyridine | H₃C-CH(CH₃)- (isobutyl) | 4-ethylpyridine |
| 410 | 3-ethylpyridine | sec-butyl (CH(CH₃)CH₂CH₃) | 4-ethylpyridine |
| 411 | 3-ethylpyridine | -CH₂CH₂CH₂NHC(O)CH₂N(CH₃)₂ | 4-ethylpyridine |
| 412 | —CH₃ | —CH₃ | 4-ethylpyridine |
| 413 | —CH₃ | H₃C-CH(CH₃)- (isobutyl) | 4-ethylpyridine |
| 414 | —CH₃ | sec-butyl | 4-ethylpyridine |
| 415 | —CH₃ | -CH₂CH₂CH₂NHC(O)CH₂N(CH₃)₂ | 4-ethylpyridine |
| 416 | sec-butyl | —CH₃ | 4-ethylpyridine |
| 417 | sec-butyl | isobutyl | 4-ethylpyridine |
| 418 | sec-butyl | isobutyl | 4-ethylpyridine |
| 419 | sec-butyl | -CH₂CH₂CH₂NHC(O)CH₂N(CH₃)₂ | 4-ethylpyridine |

TABLE 6-continued
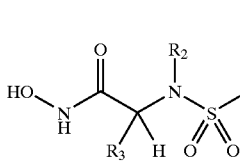
| Example | R² | R³ | R⁴ |
|---|---|---|---|
| 420 | 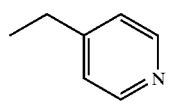 | —CH₃ | 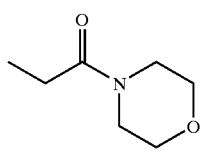 |
| 421 | 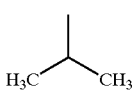 | 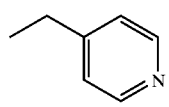 | 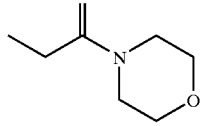 |
| 422 | 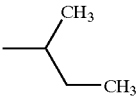 | 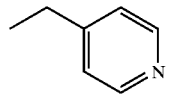 | 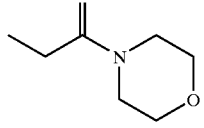 |
| 423 | 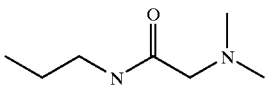 | 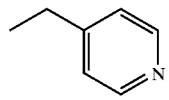 | 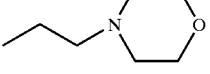 |
| 424 | 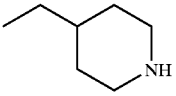 | —CH₃ | 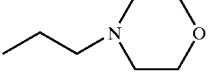 |
| 425 | 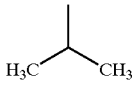 | 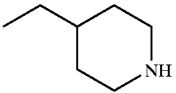 | 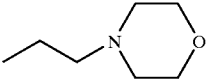 |
| 426 | 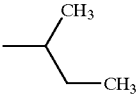 | 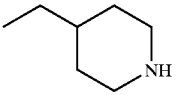 | 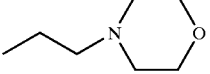 |
| 427 | 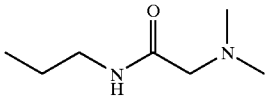 | 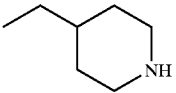 | 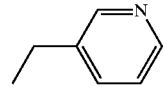 |
| 428 | 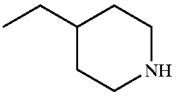 | —CH₃ | 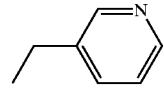 |
| 429 | 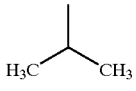 | 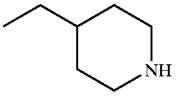 | |

TABLE 6-continued
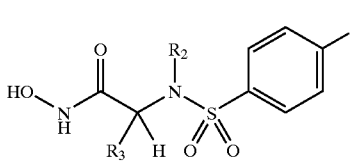
| Example | R² | R³ | R⁴ |
|---|---|---|---|
| 430 | 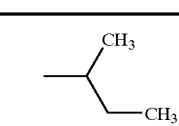 | 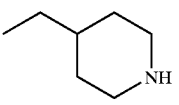 | 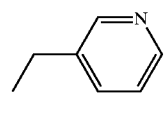 |
| 431 | 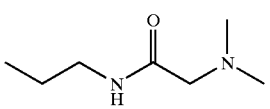 | 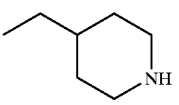 | 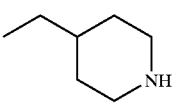 |
| 432 | —CH₃ | —CH₃ | 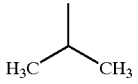 |
| 433 | —CH₃ | 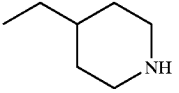 | 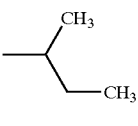 |
| 434 | —CH₃ | 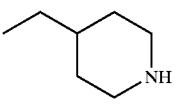 | 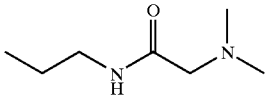 |
| 435 | —CH₃ | 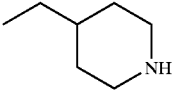 | 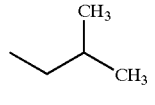 |
| 436 | 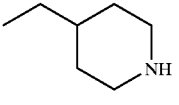 | —CH₃ | 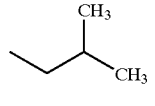 |
| 437 | 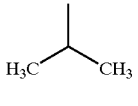 | 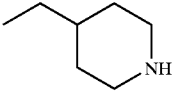 | 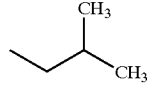 |
| 438 | 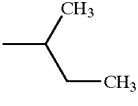 | 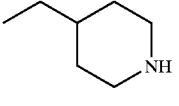 | 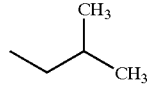 |
| 439 | 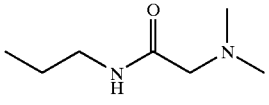 | 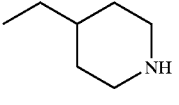 | 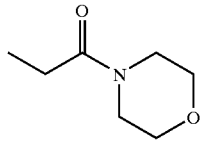 |
| 440 | 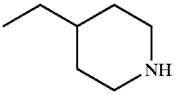 | —CH₃ |  |

TABLE 6-continued

| Example | R² | R³ | R⁴ |
|---|---|---|---|
| 441 | 1-propanoyl-morpholine | isobutyl | 4-ethylpiperidine |
| 442 | 1-propanoyl-morpholine | sec-butyl | 4-ethylpiperidine |
| 443 | 1-propanoyl-morpholine | -CH₂CH₂NHC(O)CH₂N(CH₃)₂ | 4-ethylpiperidine |
| 444 | 4-propylmorpholine | -CH₃ | 4-ethyl-1-methylpiperidine |
| 445 | 4-propylmorpholine | isobutyl | 4-ethyl-1-methylpiperidine |
| 446 | 4-propylmorpholine | sec-butyl | 4-ethyl-1-methylpiperidine |
| 447 | 4-propylmorpholine | -CH₂CH₂NHC(O)CH₂N(CH₃)₂ | 4-ethyl-1-methylpiperidine |
| 448 | 3-ethylpyridine | -CH₃ | 4-ethyl-1-methylpiperidine |
| 449 | 3-ethylpyridine | isobutyl | 4-ethyl-1-methylpiperidine |
| 450 | 3-ethylpyridine | sec-butyl | 4-ethyl-1-methylpiperidine |

TABLE 6-continued

| Example | R² | R³ | R⁴ |
|---------|----|----|----|
| 451 | 3-ethylpyridine | propyl-NH-C(O)-CH₂-N(CH₃)₂ | 1-methyl-4-ethylpiperidine |
| 452 | —CH₃ | —CH₃ | 1-methyl-4-ethylpiperidine |
| 453 | —CH₃ | isobutyl | 1-methyl-4-ethylpiperidine |
| 454 | —CH₃ | sec-butyl | 1-methyl-4-ethylpiperidine |
| 455 | —CH₃ | propyl-NH-C(O)-CH₂-N(CH₃)₂ | 1-methyl-4-ethylpiperidine |
| 456 | sec-butyl | —CH₃ | 1-methyl-4-ethylpiperidine |
| 457 | sec-butyl | isobutyl | 1-methyl-4-ethylpiperidine |
| 458 | sec-butyl | sec-butyl | 1-methyl-4-ethylpiperidine |
| 459 | sec-butyl | propyl-NH-C(O)-CH₂-N(CH₃)₂ | 1-methyl-4-ethylpiperidine |
| 460 | 1-propanoylmorpholine | —CH₃ | 1-methyl-4-ethylpiperidine |

TABLE 6-continued
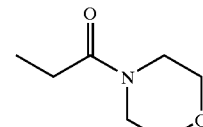
| Example | R² | R³ | R⁴ |
|---|---|---|---|
| 461 | 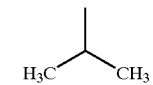 | 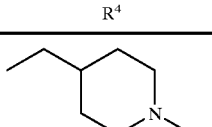 | 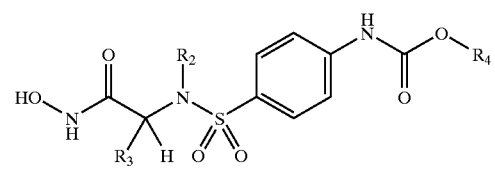 |
| 462 | 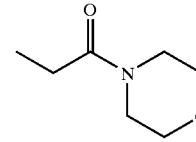 | 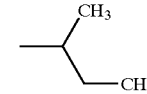 | 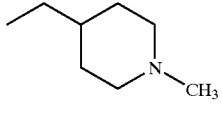 |
| 463 | 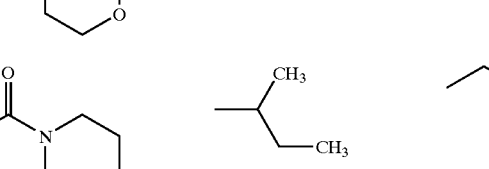 | 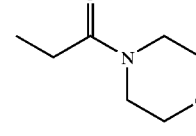 | 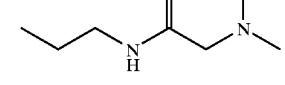 |
| 464 | 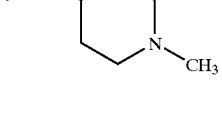 | —CH₃ | 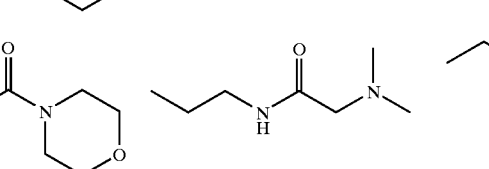 |
| 465 | 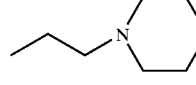 |  | 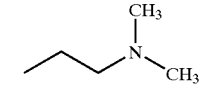 |
| 466 | 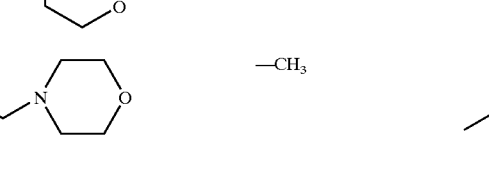 | 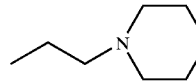 | 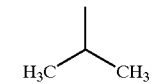 |
| 467 | 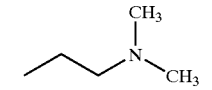 | 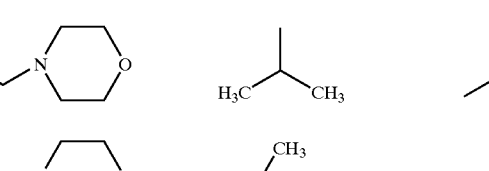 | 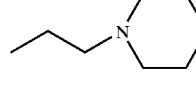 |
| 468 | 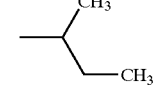 | —CH₃ | 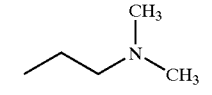 |
| 469 | 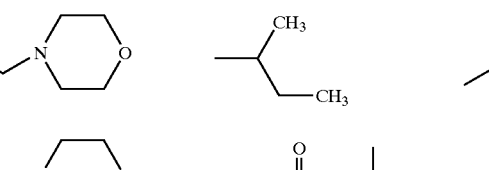 | 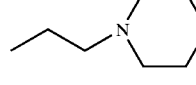 | 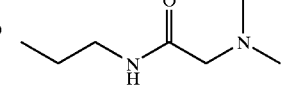 |
| 470 | 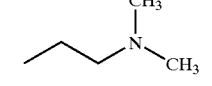 | 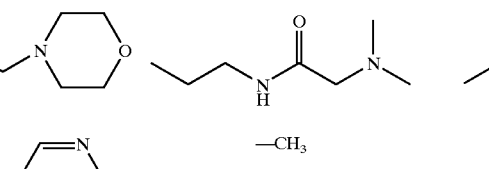 | 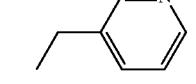 |
| 471 |  | 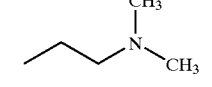 | 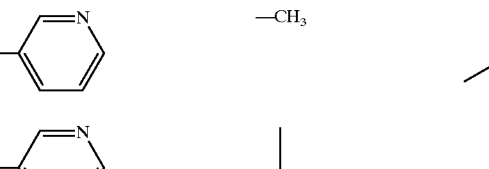 |

TABLE 6-continued
| Example | R² | R³ | R⁴ |
|---|---|---|---|
| 472 | —CH₃ | —CH₃ | 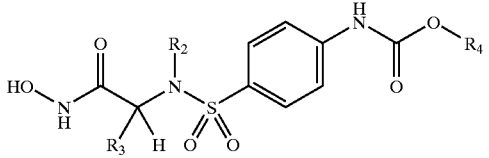 |
| 473 | —CH₃ |  |  |
| 474 | —CH₃ | 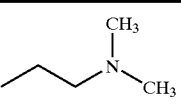 | 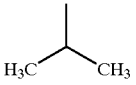 |
| 475 | —CH₃ | 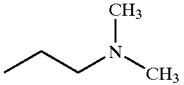 | 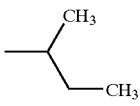 |
| 476 | 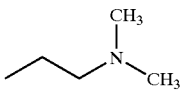 | —CH₃ | 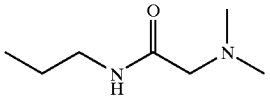 |
| 477 | 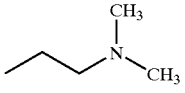 | 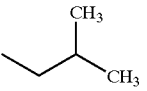 | 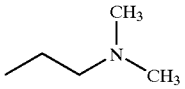 |
| 478 | 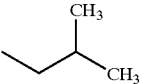 | 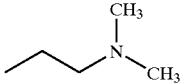 | 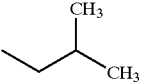 |
| 479 | 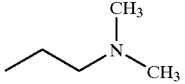 | 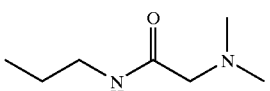 | 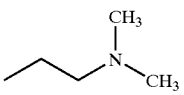 |
| 480 | 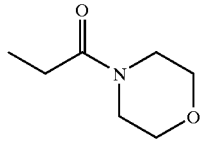 | —CH₃ | 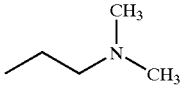 |
| 481 | 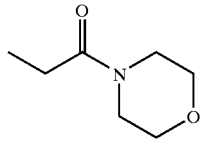 | 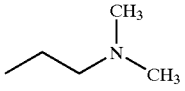 | 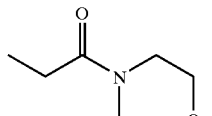 |
| 482 | 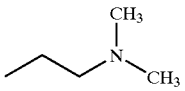 | | |

TABLE 6-continued

| Example | R² | R³ | R⁴ |
|---|---|---|---|
| 483 | propionyl-morpholine (ethyl linker) | -CH₂-C(=O)-NH-propyl-N(CH₃)₂ | -CH₂CH₂-N(CH₃)₂ |
| 484 | propyl-morpholine | —CH₃ | 4-hydroxyphenethyl |
| 485 | propyl-morpholine | isobutyl (CH(CH₃)₂-CH₂-) | 4-hydroxyphenethyl |
| 486 | propyl-morpholine | sec-butyl | 4-hydroxyphenethyl |
| 487 | propyl-morpholine | -CH₂-C(=O)-NH-propyl-N(CH₃)₂ | 4-hydroxyphenethyl |
| 488 | 3-ethylpyridine | —CH₃ | 4-hydroxyphenethyl |
| 489 | 3-ethylpyridine | isobutyl | 4-hydroxyphenethyl |
| 490 | 3-ethylpyridine | sec-butyl | 4-hydroxyphenethyl |
| 491 | 3-ethylpyridine | -CH₂-C(=O)-NH-propyl-N(CH₃)₂ | 4-hydroxyphenethyl |
| 492 | —CH₃ | —CH₃ | 4-hydroxyphenethyl |
| 493 | —CH₃ | isobutyl | 4-hydroxyphenethyl |

TABLE 6-continued
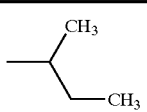
| Example | R² | R³ | R⁴ |
|---|---|---|---|
| 494 | —CH₃ | 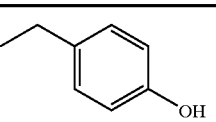 | 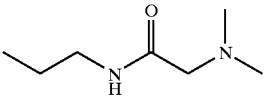 |
| 495 | —CH₃ | 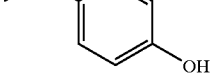 | 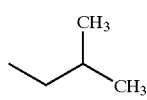 |
| 496 | 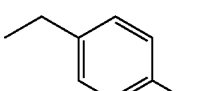 | —CH₃ | 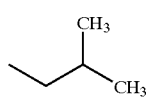 |
| 497 | 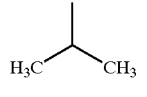 | 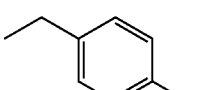 | 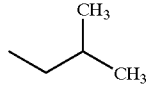 |
| 498 | 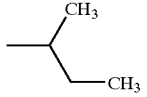 | 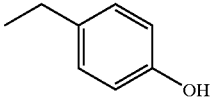 | 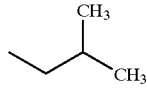 |
| 499 | 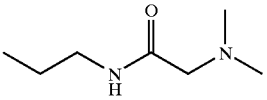 | 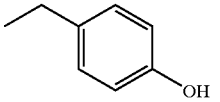 | 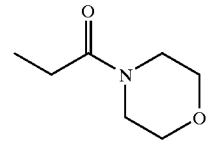 |
| 500 | 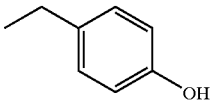 | —CH₃ | 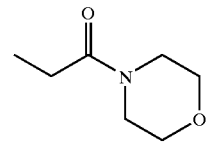 |
| 501 | 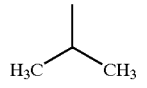 | 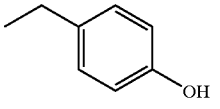 | 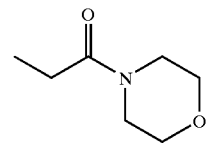 |
| 502 | 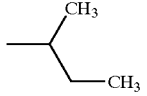 | 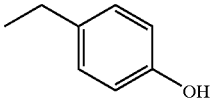 | 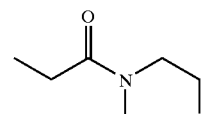 |
| 503 | 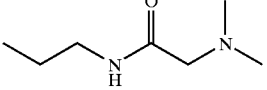 | 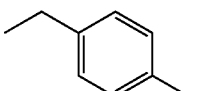 | |

TABLE 6-continued
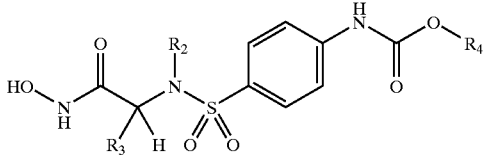
| Example | R² | R³ | R⁴ |
|---|---|---|---|
| 504 | 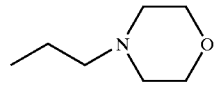 | —CH₃ |  |
| 505 | 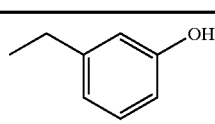 | 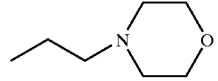 | 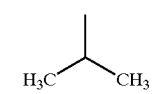 |
| 506 | 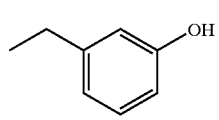 | 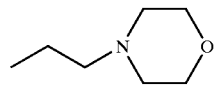 | 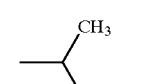 |
| 507 | 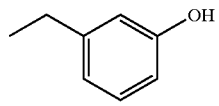 | 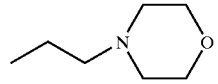 | 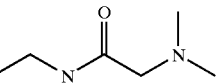 |
| 508 | 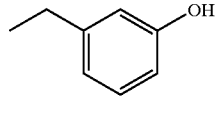 | —CH₃ | 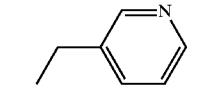 |
| 509 |  | 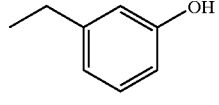 | 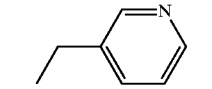 |
| 510 | 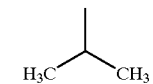 | 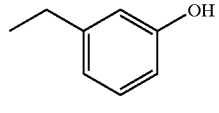 | 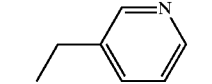 |
| 511 | 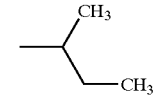 | 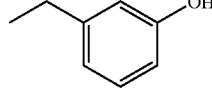 | 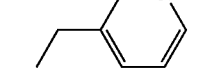 |
| 512 | —CH₃ | —CH₃ | 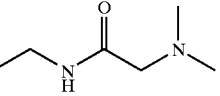 |
| 513 | —CH₃ | 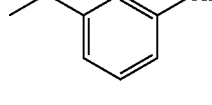 |  |
| 514 | —CH₃ |  | 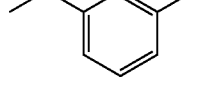 |
| 515 | —CH₃ |  | 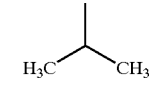 |

TABLE 6-continued
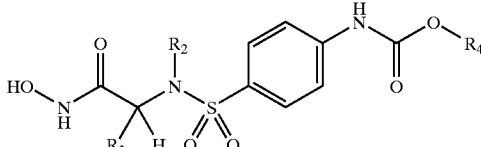

TABLE 6-continued

| Example | R² | R³ | R⁴ |
|---|---|---|---|
| 526 | propyl-morpholine | isobutyl (CH(CH₃)CH₂CH₃) | 3-methoxybenzyl |
| 527 | propyl-morpholine | -CH₂C(O)NH-CH₂CH₂-N(CH₃)₂ | 3-methoxybenzyl |
| 528 | 3-pyridylethyl | —CH₃ | 3-methoxybenzyl |
| 529 | 3-pyridylethyl | isobutyl (CH₂CH(CH₃)₂) | 3-methoxybenzyl |
| 530 | 3-pyridylethyl | sec-butyl (CH(CH₃)CH₂CH₃) | 3-methoxybenzyl |
| 531 | 3-pyridylethyl | -CH₂C(O)NH-CH₂CH₂-N(CH₃)₂ | 3-methoxybenzyl |
| 532 | —CH₃ | —CH₃ | 3-methoxybenzyl |
| 533 | —CH₃ | isobutyl (CH₂CH(CH₃)₂) | 3-methoxybenzyl |
| 534 | —CH₃ | sec-butyl (CH(CH₃)CH₂CH₃) | 3-methoxybenzyl |
| 535 | —CH₃ | -CH₂C(O)NH-CH₂CH₂-N(CH₃)₂ | 3-methoxybenzyl |
| 536 | sec-butyl (CH(CH₃)CH₂CH₃) | —CH₃ | 3-methoxybenzyl |

TABLE 6-continued

| Example | R² | R³ | R⁴ |
|---------|----|----|----|
| 537 | sec-butyl (CH(CH₃)CH₂CH₃) | isobutyl (CH₂CH(CH₃)₂) | 3-methoxy-5-ethylphenyl |
| 538 | isobutyl (CH₂CH(CH₃)₂) | sec-butyl (CH(CH₃)CH₂CH₃) | 3-methoxy-5-ethylphenyl |
| 539 | isobutyl (CH₂CH(CH₃)₂) | —CH₂C(O)NHCH₂CH₂CH₂N(CH₃)₂ | 3-methoxy-5-ethylphenyl |
| 540 | —CH₂C(O)-morpholinyl | —CH₃ | 3-methoxy-5-ethylphenyl |
| 541 | —CH₂C(O)-morpholinyl | isobutyl (CH₂CH(CH₃)₂) | 3-methoxy-5-ethylphenyl |
| 542 | —CH₂C(O)-morpholinyl | sec-butyl | 3-methoxy-5-ethylphenyl |
| 543 | —CH₂C(O)-morpholinyl | —CH₂C(O)NHCH₂CH₂CH₂N(CH₃)₂ | 3-methoxy-5-ethylphenyl |
| 544 | —CH₂CH₂-morpholinyl | —CH₃ | 2-pyrrolidinyl-ethyl |
| 545 | —CH₂CH₂-morpholinyl | isobutyl (CH₂CH(CH₃)₂) | 2-pyrrolidinyl-ethyl |
| 546 | —CH₂CH₂-morpholinyl | sec-butyl | 2-pyrrolidinyl-ethyl |

TABLE 6-continued
| Example | R² | R³ | R⁴ |
|---|---|---|---|
| 547 | 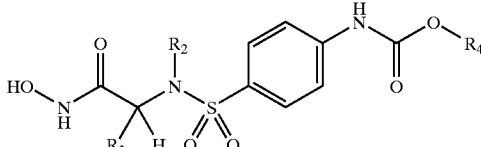 | 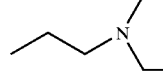 | 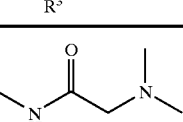 |
| 548 | 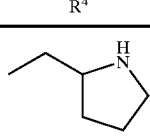 | —CH₃ | 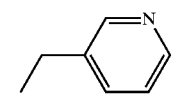 |
| 549 |  | 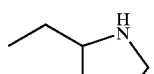 | 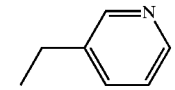 |
| 550 | 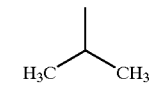 | 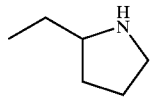 | 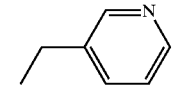 |
| 551 | 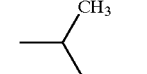 | 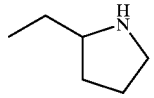 | 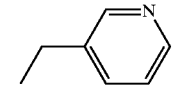 |
| 552 | —CH₃ | —CH₃ | 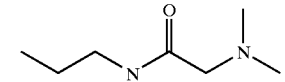 |
| 553 | —CH₃ | 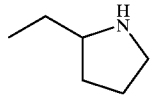 |  |
| 554 | —CH₃ |  | 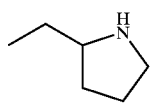 |
| 555 | —CH₃ |  | 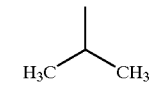 |
| 556 | 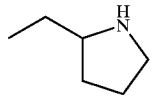 | —CH₃ |  |
| 557 | 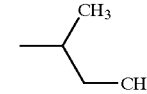 | 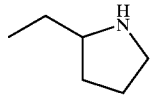 |  |
| 558 | 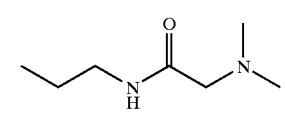 | 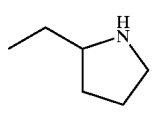 | 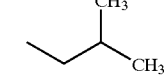 |

TABLE 6-continued
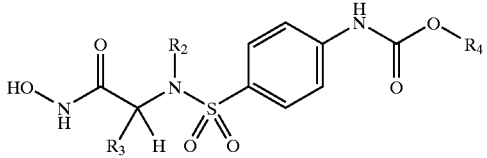
| Example | R² | R³ | R⁴ |
|---|---|---|---|
| 559 | 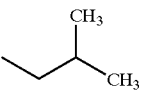 | 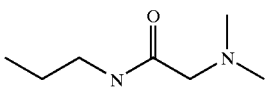 | 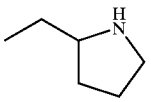 |
| 560 |  | —CH₃ | 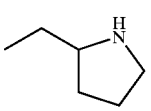 |
| 561 | 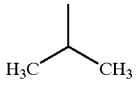 | 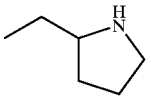 | 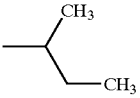 |
| 562 | 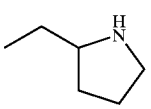 | 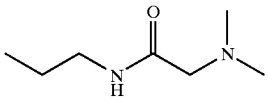 | 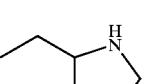 |
| 563 | 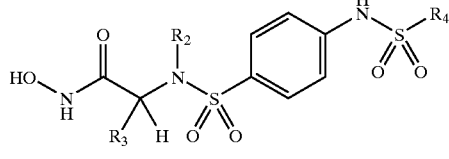 |  | 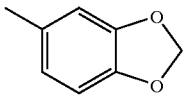 |
TABLE 7
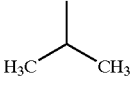
| Example | R₂ | R³ | R⁴ |
|---|---|---|---|
| 564 | 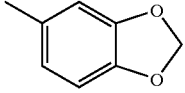 | —CH₃ | |
| 565 | | | |

TABLE 7-continued

[Structure: HO-NH-C(=O)-CH(R3)-N(R2)-SO2-C6H4-NH-SO2-R4]

| Example | R2 | R3 | R4 |
|---|---|---|---|
| 566 | propyl-morpholine | sec-butyl (CH(CH3)CH2CH3) | 1,3-benzodioxol-5-yl |
| 567 | propyl-morpholine | -CH2CH2-NH-C(=O)-CH2-N(CH3)2 | 1,3-benzodioxol-5-yl |
| 568 | ethyl-(3-pyridyl) | -CH3 | 1,3-benzodioxol-5-yl |
| 569 | ethyl-(3-pyridyl) | isobutyl (CH2CH(CH3)2) | 1,3-benzodioxol-5-yl |
| 570 | ethyl-(3-pyridyl) | sec-butyl (CH(CH3)CH2CH3) | 1,3-benzodioxol-5-yl |
| 571 | ethyl-(3-pyridyl) | -CH2CH2-NH-C(=O)-CH2-N(CH3)2 | 1,3-benzodioxol-5-yl |
| 572 | -CH3 | -CH3 | 1,3-benzodioxol-5-yl |
| 573 | -CH3 | isobutyl (CH2CH(CH3)2) | 1,3-benzodioxol-5-yl |
| 574 | -CH3 | sec-butyl (CH(CH3)CH2CH3) | 1,3-benzodioxol-5-yl |
| 575 | -CH3 | -CH2CH2-NH-C(=O)-CH2-N(CH3)2 | 1,3-benzodioxol-5-yl |
| 576 | sec-butyl (CH(CH3)CH2CH3) | -CH3 | 1,3-benzodioxol-5-yl |
| 577 | sec-butyl (CH(CH3)CH2CH3) | isobutyl (CH2CH(CH3)2) | 1,3-benzodioxol-5-yl |

TABLE 7-continued

| Example | R₂ | R³ | R⁴ |
|---|---|---|---|
| 578 | sec-butyl (CH(CH₃)CH₂CH₃) | isobutyl (CH₂CH(CH₃)₂) | benzo[1,3]dioxol-5-yl |
| 579 | —CH, sec-butyl | —CH₂C(O)NHCH₂CH₂CH₂N(CH₃)₂ | benzo[1,3]dioxol-5-yl |
| 580 | —C(O)CH₂CH₂-morpholinyl | —CH₃ | benzo[1,3]dioxol-5-yl |
| 581 | —C(O)CH₂CH₂-morpholinyl | isobutyl | benzo[1,3]dioxol-5-yl |
| 582 | —C(O)CH₂CH₂-morpholinyl | sec-butyl | benzo[1,3]dioxol-5-yl |
| 583 | —C(O)CH₂CH₂-morpholinyl | —CH₂C(O)NHCH₂CH₂CH₂N(CH₃)₂ | benzo[1,3]dioxol-5-yl |
| 584 | —CH₂CH₂-morpholinyl | —CH₃ | —CH₃ |
| 585 | —CH₂CH₂-morpholinyl | isobutyl | —CH₃ |
| 586 | —CH₂CH₂-morpholinyl | sec-butyl | —CH₃ |
| 587 | —CH₂CH₂-morpholinyl | —CH₂C(O)NHCH₂CH₂CH₂N(CH₃)₂ | —CH₃ |
| 588 | —CH₂CH₂-(pyridin-3-yl) | —CH₃ | —CH₃ |

TABLE 7-continued
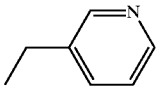
| Example | R₂ | R³ | R⁴ |
|---|---|---|---|
| 589 | 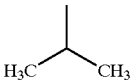 | 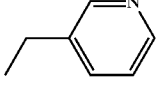 | —CH₃ |
| 590 | 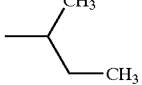 | 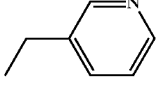 | —CH₃ |
| 591 | 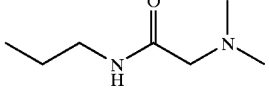 | 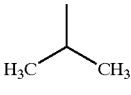 | —CH₃ |
| 592 | —CH₃ | —CH₃ | —CH₃ |
| 593 | —CH₃ | 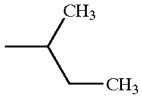 | —CH₃ |
| 594 | —CH₃ | 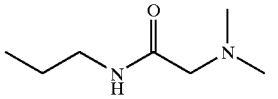 | —CH₃ |
| 595 | —CH₃ | 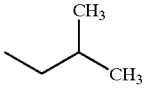 | —CH₃ |
| 596 | 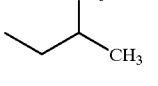 | —CH₃ | —CH₃ |
| 597 | 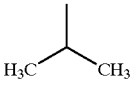 | 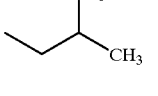 | —CH₃ |
| 598 | 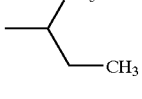 | 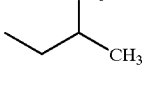 | —CH₃ |
| 599 | 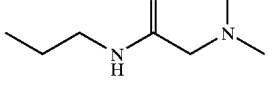 | 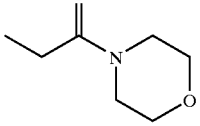 | —CH₃ |
| 600 |  | —CH₃ | —CH₃ |

TABLE 7-continued

| Example | R₂ | R³ | R⁴ |
|---|---|---|---|
| 601 | propionyl-morpholine | isobutyl | —CH₃ |
| 602 | propionyl-morpholine | sec-butyl | —CH₃ |
| 603 | propionyl-morpholine | -CH₂CH₂NHC(O)CH₂N(CH₃)₂ | —CH₃ |
| 604 | propyl-morpholine | —CH₃ | benzyl |
| 605 | propyl-morpholine | isobutyl | benzyl |
| 606 | propyl-morpholine | sec-butyl | benzyl |
| 607 | propyl-morpholine | -CH₂CH₂NHC(O)CH₂N(CH₃)₂ | benzyl |
| 608 | ethyl-pyridin-3-yl | —CH₃ | benzyl |
| 609 | ethyl-pyridin-3-yl | isobutyl | benzyl |
| 610 | ethyl-pyridin-3-yl | sec-butyl | benzyl |
| 611 | ethyl-pyridin-3-yl | -CH₂CH₂NHC(O)CH₂N(CH₃)₂ | benzyl |

TABLE 7-continued

| Example | R² | R³ | R⁴ |
|---|---|---|---|
| 612 | —CH₃ | —CH₃ | phenyl-CH₂CH₂— |
| 613 | —CH₃ | isobutyl (H₃C-CH(CH₃)-CH₂-) | phenyl-CH₂CH₂— |
| 614 | —CH₃ | sec-butyl (CH₃-CH(CH₃)-CH₂- with CH₃) | phenyl-CH₂CH₂— |
| 615 | —CH₃ | -CH₂CH₂CH₂-NH-C(O)-CH₂-N(CH₃)₂ | phenyl-CH₂— |
| 616 | sec-butyl | —CH₃ | phenyl-CH₂CH₂— |
| 617 | sec-butyl | isobutyl | phenyl-CH₂CH₂— |
| 618 | sec-butyl | sec-butyl | phenyl-CH₂CH₂— |
| 619 | sec-butyl | -CH₂CH₂CH₂-NH-C(O)-CH₂-N(CH₃)₂ | phenyl-CH₂— |
| 620 | -CH₂CH₂-C(O)-morpholinyl | —CH₃ | phenyl-CH₂CH₂— |
| 621 | -CH₂CH₂-C(O)-morpholinyl | isobutyl | phenyl-CH₂CH₂— |

TABLE 7-continued
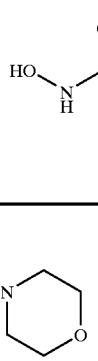
| Example | R₂ | R³ | R⁴ |
|---|---|---|---|
| 622 | 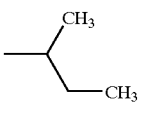 |  | 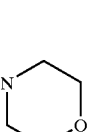 |
| 623 | 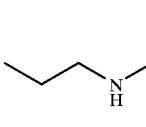 | 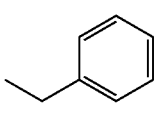 | 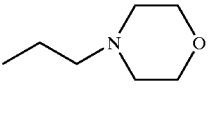 |
| 624 |  | —CH₃ | 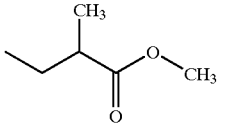 |
| 625 | 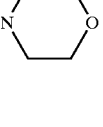 | 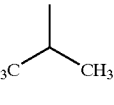 | 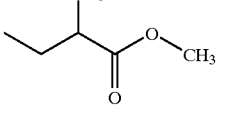 |
| 626 | 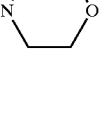 | 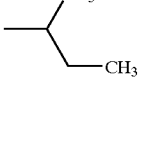 | 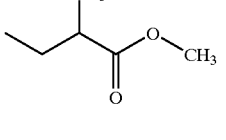 |
| 627 | 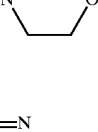 | 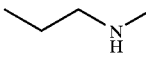 | 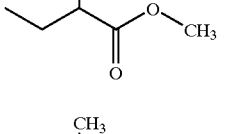 |
| 628 | 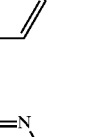 | —CH₃ |  |
| 629 | 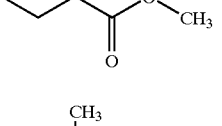 | 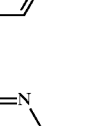 | 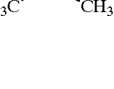 |
| 630 | 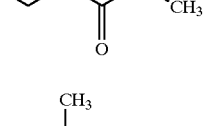 |  | 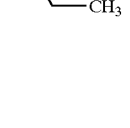 |

TABLE 7-continued

| Example | R₂ | R³ | R⁴ |
|---------|----|----|----|
| 631 | 3-pyridyl-ethyl | propyl-NH-C(O)-CH₂-N(CH₃)₂ | methyl 2-methylbutanoate |
| 632 | —CH₃ | —CH₃ | methyl 2-methylbutanoate |
| 633 | —CH₃ | isobutyl (CH(CH₃)CH₂) | methyl 2-methylbutanoate |
| 634 | —CH₃ | sec-butyl | methyl 2-methylbutanoate |
| 635 | —CH₃ | propyl-NH-C(O)-CH₂-N(CH₃)₂ | methyl 2-methylbutanoate |
| 636 | sec-butyl | —CH₃ | methyl 2-methylbutanoate |
| 637 | sec-butyl | isobutyl | methyl 2-methylbutanoate |
| 638 | sec-butyl | sec-butyl | methyl 2-methylbutanoate |
| 639 | sec-butyl | propyl-NH-C(O)-CH₂-N(CH₃)₂ | methyl 2-methylbutanoate |

TABLE 7-continued

| Example | R₂ | R³ | R⁴ |
|---|---|---|---|
| 640 | 1-(morpholin-4-yl)propan-1-one | —CH₃ | methyl 2-methylbutanoate |
| 641 | 1-(morpholin-4-yl)propan-1-one | isobutyl | methyl 2-methylbutanoate |
| 642 | 1-(morpholin-4-yl)propan-1-one | sec-butyl | methyl 2-methylbutanoate |
| 643 | 1-(morpholin-4-yl)propan-1-one | N-(2-(dimethylamino)acetyl)aminoethyl | methyl 2-methylbutanoate |
| 644 | 3-(morpholin-4-yl)propyl | —CH₃ | biphenyl-4-yl |
| 645 | 3-(morpholin-4-yl)propyl | isobutyl | biphenyl-4-yl |
| 646 | 3-(morpholin-4-yl)propyl | sec-butyl | biphenyl-4-yl |
| 647 | 3-(morpholin-4-yl)propyl | N-(2-(dimethylamino)acetyl)aminoethyl | biphenyl-4-yl |
| 648 | 2-(pyridin-3-yl)ethyl | —CH₃ | biphenyl-4-yl |
| 649 | 2-(pyridin-3-yl)ethyl | isobutyl | biphenyl-4-yl |
| 650 | 2-(pyridin-3-yl)ethyl | sec-butyl | biphenyl-4-yl |

TABLE 7-continued

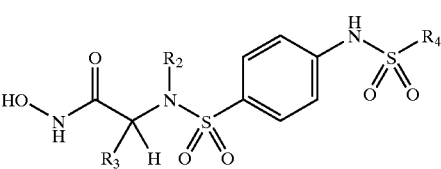

| Example | R₂ | R³ | R⁴ |
|---|---|---|---|
| 651 | 3-ethyl-pyridine | propyl-NH-C(O)-CH₂-N(CH₃)₂ | 4-biphenyl |
| 652 | —CH₃ | —CH₃ | 4-biphenyl |
| 653 | —CH₃ | isobutyl | 4-biphenyl |
| 654 | —CH₃ | sec-butyl | 4-biphenyl |
| 655 | —CH₃ | propyl-NH-C(O)-CH₂-N(CH₃)₂ | 4-biphenyl |
| 656 | sec-butyl | —CH₃ | 4-biphenyl |
| 657 | sec-butyl | isobutyl | 4-biphenyl |
| 658 | sec-butyl | sec-butyl | 4-biphenyl |
| 659 | sec-butyl | propyl-NH-C(O)-CH₂-N(CH₃)₂ | 4-biphenyl |
| 660 | CH₂-C(O)-morpholine | —CH₃ | 4-biphenyl |
| 661 | CH₂-C(O)-morpholine | isobutyl | 4-biphenyl |

TABLE 7-continued
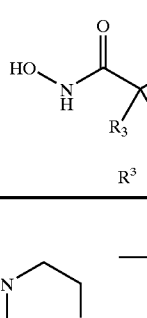
| Example | R₂ | R³ | R⁴ |
|---|---|---|---|
| 662 |  | 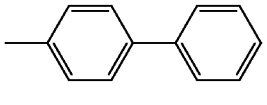 | 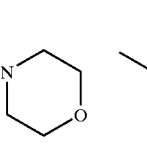 |
| 663 | 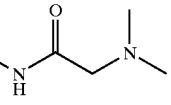 | 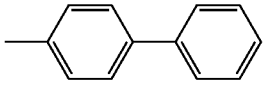 | 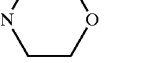 |
| 664 | 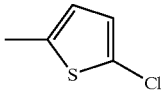 | —CH₃ | 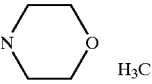 |
| 665 |  | 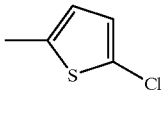 | 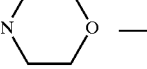 |
| 666 | 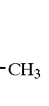 | 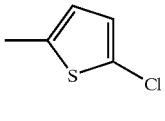 | 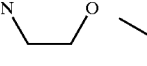 |
| 667 | 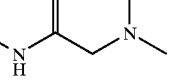 | 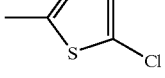 |  |
| 668 | 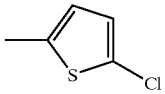 | —CH₃ | 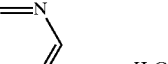 |
| 669 | 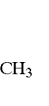 | 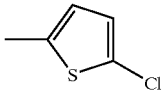 |  |
| 670 |  |  |  |
| 671 | 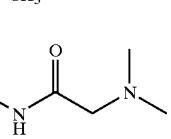 |  | 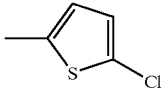 |
| 672 | —CH₃ | —CH₃ | |

TABLE 7-continued
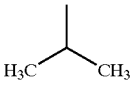
| Example | R₂ | R³ | R⁴ |
|---|---|---|---|
| 673 | —CH₃ | 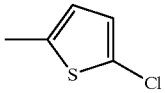 | 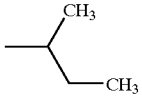 |
| 674 | —CH₃ | 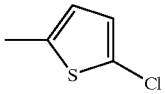 | 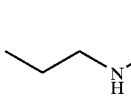 |
| 675 | —CH₃ | 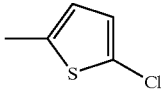 | 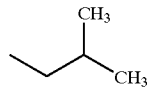 |
| 676 | 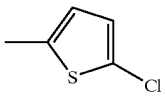 | —CH₃ | 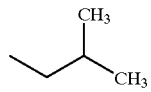 |
| 677 | 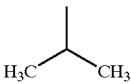 | 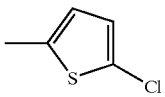 | 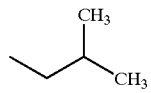 |
| 678 | 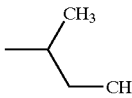 | 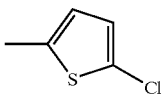 | 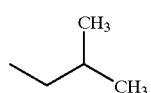 |
| 679 | 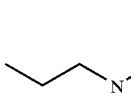 | 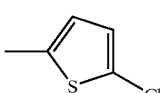 | 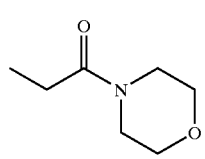 |
| 680 | 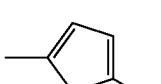 | —CH₃ | 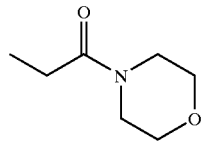 |
| 681 | 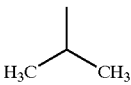 | 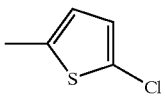 | 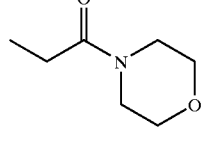 |
| 682 | 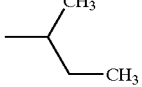 | 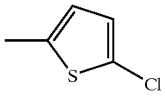 | |

TABLE 7-continued

| Example | R₂ | R³ | R⁴ |
|---|---|---|---|
| 683 | propyl-morpholine (propanoyl morpholine) | propyl-NH-C(O)-CH₂-N(CH₃)₂ | 5-chlorothiophen-2-yl |
| 684 | propyl-morpholine | —CH₃ | pentyl |
| 685 | propyl-morpholine | isobutyl | pentyl |
| 686 | propyl-morpholine | sec-butyl | pentyl |
| 687 | propyl-morpholine | propyl-NH-C(O)-CH₂-N(CH₃)₂ | pentyl |
| 688 | ethyl-(pyridin-3-yl) | —CH₃ | pentyl |
| 689 | ethyl-(pyridin-3-yl) | isobutyl | pentyl |
| 690 | ethyl-(pyridin-3-yl) | sec-butyl | pentyl |
| 691 | ethyl-(pyridin-3-yl) | propyl-NH-C(O)-CH₂-N(CH₃)₂ | pentyl |
| 692 | —CH₃ | —CH₃ | pentyl |
| 693 | —CH₃ | isobutyl | pentyl |
| 694 | —CH₃ | sec-butyl | pentyl |

TABLE 7-continued

| Example | R₂ | R³ | R⁴ |
|---|---|---|---|
| 695 | —CH₃ | propyl-NH-C(=O)-CH₂-N(CH₃)₂ | n-pentyl |
| 696 | sec-butyl (CH(CH₃)CH₂CH₃) | —CH₃ | n-pentyl |
| 697 | sec-butyl | isobutyl | n-pentyl |
| 698 | sec-butyl | isobutyl | n-pentyl |
| 699 | isobutyl | propyl-NH-C(=O)-CH₂-N(CH₃)₂ | n-pentyl |
| 700 | morpholinyl-C(=O)-CH₂CH₂- | —CH₃ | n-pentyl |
| 701 | morpholinyl-C(=O)-CH₂CH₂- | isobutyl | n-pentyl |
| 702 | morpholinyl-C(=O)-CH₂CH₂- | isobutyl | n-pentyl |
| 703 | morpholinyl-C(=O)-CH₂CH₂- | propyl-NH-C(=O)-CH₂-N(CH₃)₂ | n-pentyl |
| 704 | morpholinyl-propyl | —CH₃ | 4-methoxyphenyl |
| 705 | morpholinyl-propyl | isobutyl | 4-methoxyphenyl |

TABLE 7-continued
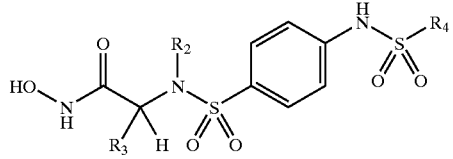
| Example | R₂ | R³ | R⁴ |
|---|---|---|---|
| 706 | 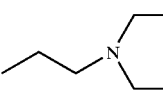 | 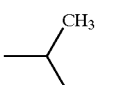 | 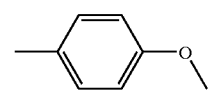 |
| 707 | 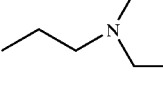 | 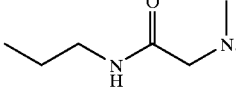 | 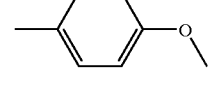 |
| 708 | 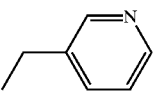 | —CH₃ |  |
| 709 |  | 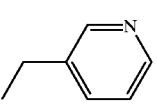 | 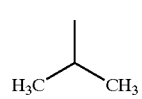 |
| 710 | 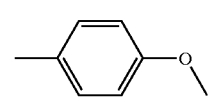 | 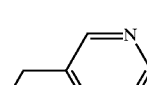 | 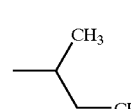 |
| 711 | 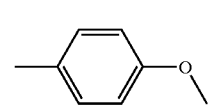 | 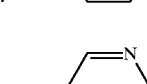 | 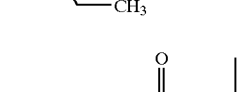 |
| 712 | —CH₃ | —CH₃ |  |
| 713 | —CH₃ |  |  |
| 714 | —CH₃ | 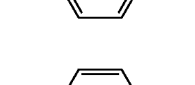 |  |
| 715 | —CH₃ |  | 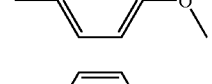 |
| 716 |  | —CH₃ | 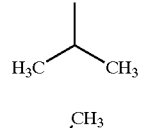 |
| 717 | 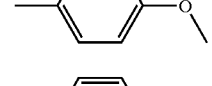 |  | 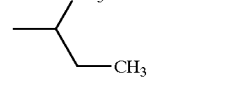 |

TABLE 7-continued

| Example | R₂ | R³ | R⁴ |
|---------|----|----|----|
| 718 | sec-butyl (CH(CH₃)CH₂CH₃) | isobutyl (CH₂CH(CH₃)₂) | 4-methoxyphenyl |
| 719 | sec-butyl | -CH₂CH₂NHC(O)CH₂N(CH₃)₂ | 4-methoxyphenyl |
| 720 | -CH₂CH₂-C(O)-morpholinyl | -CH₃ | 4-methoxyphenyl |
| 721 | -CH₂CH₂-C(O)-morpholinyl | isobutyl | 4-methoxyphenyl |
| 722 | -CH₂CH₂-C(O)-morpholinyl | sec-butyl | 4-methoxyphenyl |
| 723 | -CH₂CH₂-C(O)-morpholinyl | -CH₂CH₂NHC(O)CH₂N(CH₃)₂ | 4-methoxyphenyl |
| 724 | -CH₂CH₂CH₂-morpholinyl | -CH₃ | benzoxazol-5-yl |
| 725 | -CH₂CH₂CH₂-morpholinyl | isobutyl | benzoxazol-5-yl |
| 726 | -CH₂CH₂CH₂-morpholinyl | sec-butyl | benzoxazol-5-yl |
| 727 | -CH₂CH₂CH₂-morpholinyl | -CH₂CH₂NHC(O)CH₂N(CH₃)₂ | benzoxazol-5-yl |

TABLE 7-continued

Structure: HO-NH-C(=O)-CH(R3)-N(R2)-SO2-C6H4-NH-SO2-R4

| Example | R₂ | R³ | R⁴ |
|---|---|---|---|
| 728 | 3-pyridylethyl | —CH₃ | 5-benzoxazolyl |
| 729 | 3-pyridylethyl | isobutyl | 5-benzoxazolyl |
| 730 | 3-pyridylethyl | sec-butyl | 5-benzoxazolyl |
| 731 | 3-pyridylethyl | —CH₂C(=O)NH-CH₂CH₂CH₂-N(CH₃)₂ | 5-benzoxazolyl |
| 732 | —CH₃ | —CH₃ | 5-benzoxazolyl |
| 733 | —CH₃ | isobutyl | 5-benzoxazolyl |
| 734 | —CH₃ | sec-butyl | 5-benzoxazolyl |
| 735 | —CH₃ | —CH₂C(=O)NH-CH₂CH₂CH₂-N(CH₃)₂ | 5-benzoxazolyl |
| 736 | sec-butyl | —CH₃ | 5-benzoxazolyl |
| 737 | sec-butyl | isobutyl | 5-benzoxazolyl |
| 738 | sec-butyl | sec-butyl | 5-benzoxazolyl |
| 739 | sec-butyl | —CH₂C(=O)NH-CH₂CH₂CH₂-N(CH₃)₂ | 5-benzoxazolyl |

TABLE 7-continued

| Example | R₂ | R³ | R⁴ |
|---|---|---|---|
| 740 | 1-(morpholin-4-yl)propan-1-one | —CH₃ | 5-methylbenzoxazole |
| 741 | 1-(morpholin-4-yl)propan-1-one | isobutyl (H₃C-CH-CH₃) | 5-methylbenzoxazole |
| 742 | 1-(morpholin-4-yl)propan-1-one | sec-butyl (CH₃-CH-CH₂-CH₃) | 5-methylbenzoxazole |
| 743 | 1-(morpholin-4-yl)propan-1-one | -CH₂-CH₂-NH-C(O)-CH₂-N(CH₃)₂ | 5-methylbenzoxazole |
| 744 | 4-propylmorpholine | —CH₃ | 4-isopropylphenyl |
| 745 | 4-propylmorpholine | isobutyl | 4-isopropylphenyl |
| 746 | 4-propylmorpholine | sec-butyl | 4-isopropylphenyl |
| 747 | 4-propylmorpholine | -CH₂-CH₂-NH-C(O)-CH₂-N(CH₃)₂ | 4-isopropylphenyl |
| 748 | 3-ethylpyridine | —CH₃ | 4-isopropylphenyl |
| 749 | 3-ethylpyridine | isobutyl | 4-isopropylphenyl |
| 750 | 3-ethylpyridine | sec-butyl | 4-isopropylphenyl |

TABLE 7-continued

| Example | R₂ | R³ | R⁴ |
|---|---|---|---|
| 751 | 3-ethylpyridine | -CH₂-C(=O)-NH-propyl-N(CH₃)₂ | 4-isopropylphenyl |
| 752 | —CH₃ | —CH₃ | 4-isopropylphenyl |
| 753 | —CH₃ | -CH(CH₃)₂ (isobutyl) | 4-isopropylphenyl |
| 754 | —CH₃ | sec-butyl | 4-isopropylphenyl |
| 755 | —CH₃ | -CH₂-C(=O)-NH-propyl-N(CH₃)₂ | 4-isopropylphenyl |
| 756 | sec-butyl | —CH₃ | 4-isopropylphenyl |
| 757 | sec-butyl | isobutyl | 4-isopropylphenyl |
| 758 | sec-butyl | sec-butyl | 4-isopropylphenyl |
| 759 | sec-butyl | -CH₂-C(=O)-NH-propyl-N(CH₃)₂ | 4-isopropylphenyl |
| 760 | -CH₂-C(=O)-morpholine | —CH₃ | 4-isopropylphenyl |
| 761 | -CH₂-C(=O)-morpholine | isobutyl | 4-isopropylphenyl | ns
TABLE 7-continued
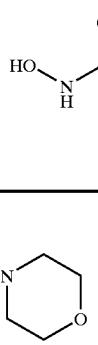
| Example | R₂ | R³ | R⁴ |
|---|---|---|---|
| 762 | 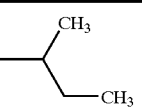 | 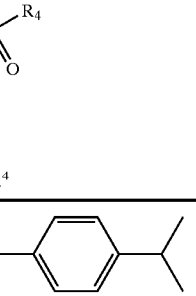 | 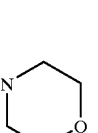 |
| 763 | 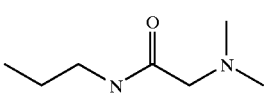 | 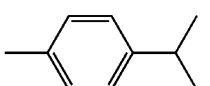 | 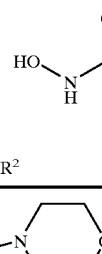 |
TABLE 8
| Example | R² | R³ | R⁴ |
|---|---|---|---|
| 764 | 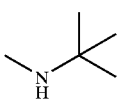 | —CH₃ |  |
| 765 | 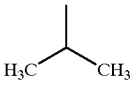 | 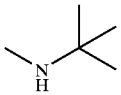 |  |
| 766 | 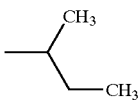 | 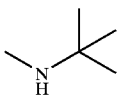 |  |
| 767 | 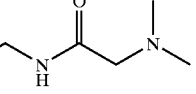 | 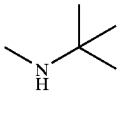 |  |
| 768 |  | —CH₃ | 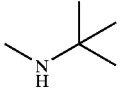 |
| 769 |  | 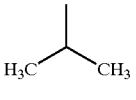 | 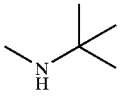 |
| 770 |  | 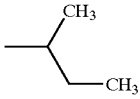 | 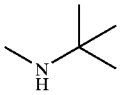 |

TABLE 8-continued

| Example | R² | R³ | R⁴ |
|---|---|---|---|
| 771 | 3-ethylpyridine | propyl-NH-C(O)-CH₂-N(CH₃)₂ | NH-C(CH₃)₃ |
| 772 | —CH₃ | —CH₃ | NH-C(CH₃)₃ |
| 773 | —CH₃ | isobutyl (H₃C-CH-CH₃) | NH-C(CH₃)₃ |
| 774 | —CH₃ | sec-butyl (CH₃-CH-CH₂-CH₃) | NH-C(CH₃)₃ |
| 775 | —CH₃ | propyl-NH-C(O)-CH₂-N(CH₃)₂ | NH-C(CH₃)₃ |
| 776 | sec-butyl | —CH₃ | NH-C(CH₃)₃ |
| 777 | sec-butyl | isobutyl | NH-C(CH₃)₃ |
| 778 | sec-butyl | sec-butyl | NH-C(CH₃)₃ |
| 779 | sec-butyl | propyl-NH-C(O)-CH₂-N(CH₃)₂ | NH-C(CH₃)₃ |
| 780 | ethyl-C(O)-morpholine | —CH₃ | NH-C(CH₃)₃ |
| 781 | ethyl-C(O)-morpholine | isobutyl | NH-C(CH₃)₃ |

TABLE 8-continued
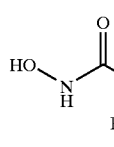
| Example | R² | R³ | R⁴ |
|---|---|---|---|
| 782 | 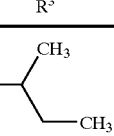 | 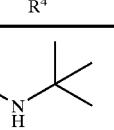 | 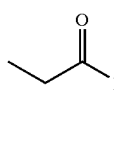 |
| 783 | 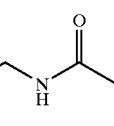 | 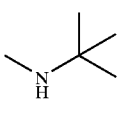 | 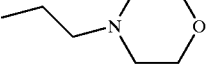 |
| 784 | 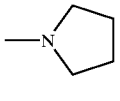 | —CH₃ | 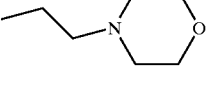 |
| 785 | 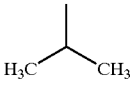 | 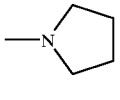 | 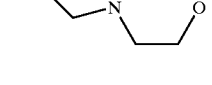 |
| 786 | 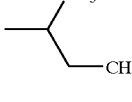 | 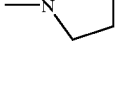 | 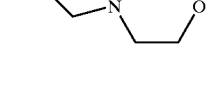 |
| 787 | 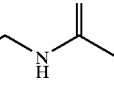 | 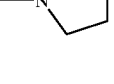 | 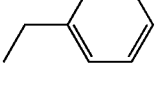 |
| 788 | 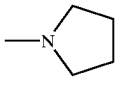 | —CH₃ | 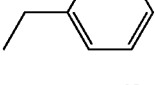 |
| 789 | 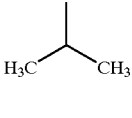 | 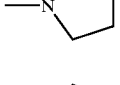 | 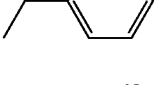 |
| 790 | 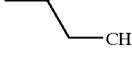 | 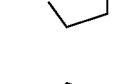 | 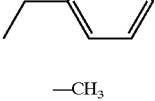 |
| 791 | 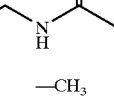 |  | 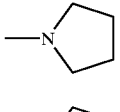 |
| 792 | —CH₃ | —CH₃ | 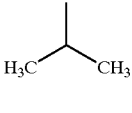 |
| 793 | —CH₃ | 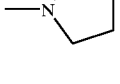 | |

TABLE 8-continued

| Example | R² | R³ | R⁴ |
|---|---|---|---|
| 794 | —CH₃ | —CH₂CH(CH₃)CH₂CH₃ (sec-butyl/isobutyl) | pyrrolidin-1-yl |
| 795 | —CH₃ | —CH₂CH₂CH₂NHC(O)CH₂N(CH₃)₂ | pyrrolidin-1-yl |
| 796 | sec-butyl | —CH₃ | pyrrolidin-1-yl |
| 797 | sec-butyl | isobutyl | pyrrolidin-1-yl |
| 798 | sec-butyl | isobutyl | pyrrolidin-1-yl |
| 799 | sec-butyl | —CH₂CH₂CH₂NHC(O)CH₂N(CH₃)₂ | pyrrolidin-1-yl |
| 800 | —CH₂CH₂C(O)-morpholin-4-yl | —CH₃ | pyrrolidin-1-yl |
| 801 | —CH₂CH₂C(O)-morpholin-4-yl | isobutyl | pyrrolidin-1-yl |
| 802 | —CH₂CH₂C(O)-morpholin-4-yl | isobutyl | pyrrolidin-1-yl |
| 803 | —CH₂CH₂C(O)-morpholin-4-yl | —CH₂CH₂CH₂NHC(O)CH₂N(CH₃)₂ | pyrrolidin-1-yl |

TABLE 8-continued
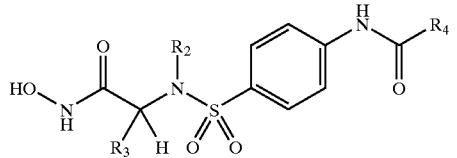
| Example | R² | R³ | R⁴ |
|---|---|---|---|
| 804 | 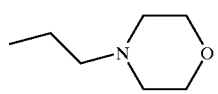 | —CH₃ | 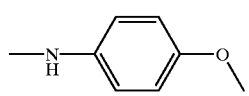 |
| 805 | 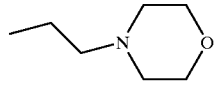 | 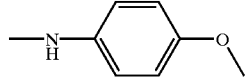 | 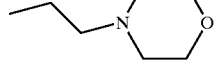 |
| 806 | 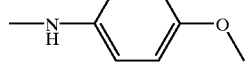 | 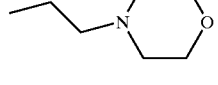 | 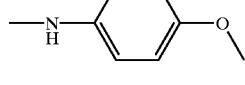 |
| 807 | 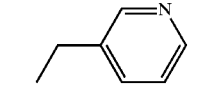 | 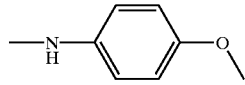 | 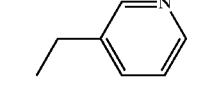 |
| 808 | 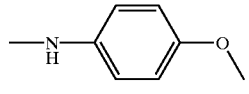 | —CH₃ | 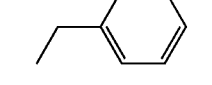 |
| 809 | 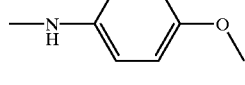 | 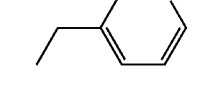 | 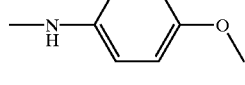 |
| 810 | 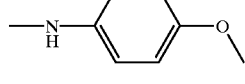 | 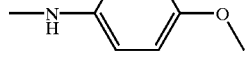 | 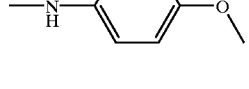 |
| 811 | 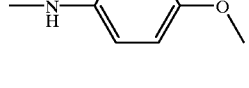 | | |
| 812 | —CH₃ | —CH₃ | |
| 813 | —CH₃ | | |
| 814 | —CH₃ | | |
| 815 | —CH₃ | | |

TABLE 8-continued

| Example | R² | R³ | R⁴ |
|---|---|---|---|
| 816 | sec-butyl | —CH₃ | —NH-C₆H₄-OCH₃ (para) |
| 817 | sec-butyl | isobutyl | —NH-C₆H₄-OCH₃ (para) |
| 818 | sec-butyl | isobutyl | —NH-C₆H₄-OCH₃ (para) |
| 819 | isobutyl | -CH₂-C(=O)-NH-CH₂CH₂CH₂-N(CH₃)₂ | —NH-C₆H₄-OCH₃ (para) |
| 820 | -CH₂CH₂-C(=O)-morpholinyl | —CH₃ | —NH-C₆H₄-OCH₃ (para) |
| 821 | -CH₂CH₂-C(=O)-morpholinyl | isobutyl | —NH-C₆H₄-OCH₃ (para) |
| 822 | -CH₂CH₂-C(=O)-morpholinyl | isobutyl | —NH-C₆H₄-OCH₃ (para) |
| 823 | -CH₂CH₂-C(=O)-morpholinyl | -CH₂-C(=O)-NH-CH₂CH₂CH₂-N(CH₃)₂ | —NH-C₆H₄-OCH₃ (para) |
| 824 | -CH₂CH₂CH₂-morpholinyl | —CH₃ | -morpholinyl |
| 825 | -CH₂CH₂CH₂-morpholinyl | isobutyl | -morpholinyl |
| 826 | -CH₂CH₂CH₂-morpholinyl | isobutyl | -morpholinyl |

TABLE 8-continued
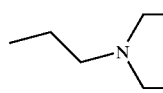
| Example | R² | R³ | R⁴ |
|---|---|---|---|
| 827 | 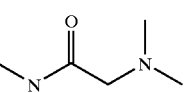 | 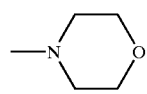 | 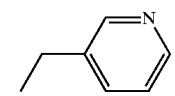 |
| 828 | 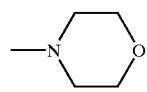 | —CH₃ | 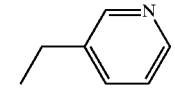 |
| 829 | 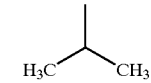 | 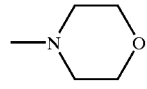 | 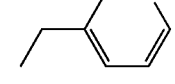 |
| 830 | 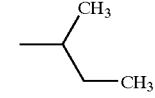 | 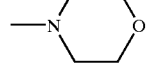 | 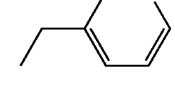 |
| 831 | 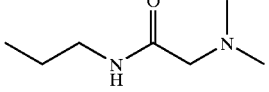 | 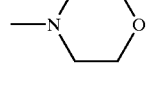 | 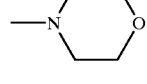 |
| 832 | —CH₃ | —CH₃ | 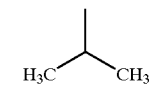 |
| 833 | —CH₃ | 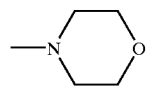 | 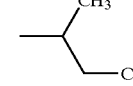 |
| 834 | —CH₃ | 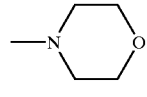 | 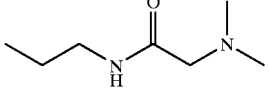 |
| 835 | —CH₃ | 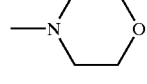 | 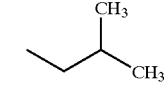 |
| 836 | 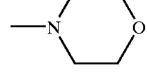 | —CH₃ | 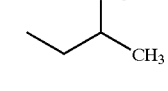 |
| 837 | 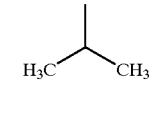 | 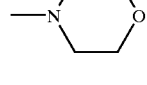 | 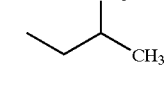 |
| 838 | 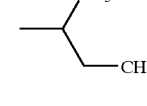 | 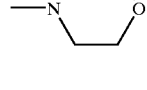 | |

TABLE 8-continued
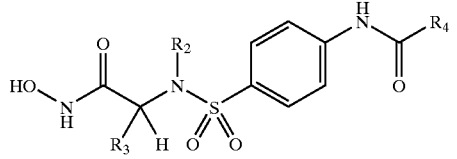
| Example | R² | R³ | R⁴ |
|---|---|---|---|
| 839 | 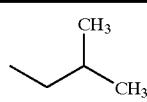 | 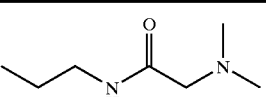 | 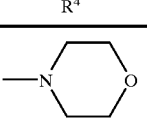 |
| 840 |  | —CH₃ | 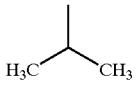 |
| 841 | 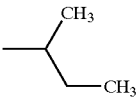 | 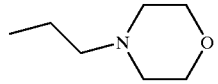 |  |
| 842 |  | 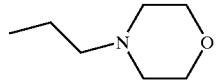 | 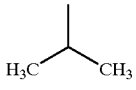 |
| 843 |  | 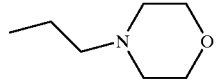 | 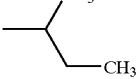 |
| 844 |  | —CH₃ | —NH₂ |
| 845 | 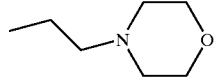 | 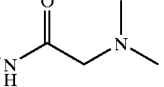 | —NH₂ |
| 846 |  | 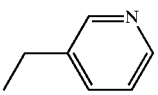 | —NH₂ |
| 847 |  |  | —NH₂ |
| 848 | 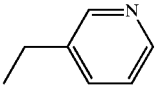 | —CH₃ | —NH₂ |
| 849 | 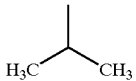 |  | —NH₂ |

TABLE 8-continued

| Example | R² | R³ | R⁴ |
|---|---|---|---|
| 850 | 3-ethylpyridine | isobutyl (CH(CH₃)CH₂CH₃) | —NH₂ |
| 851 | 3-ethylpyridine | —CH₂CH₂CH₂NHC(O)CH₂N(CH₃)₂ | —NH₂ |
| 852 | —CH₃ | —CH₃ | —NH₂ |
| 853 | —CH₃ | —CH₂CH(CH₃)₂ | —NH₂ |
| 854 | —CH₃ | —CH(CH₃)CH₂CH₃ | —NH₂ |
| 855 | —CH₃ | —CH₂CH₂CH₂NHC(O)CH₂N(CH₃)₂ | —NH₂ |
| 856 | —CH(CH₃)CH₂CH₃ | —CH₃ | —NH₂ |
| 857 | —CH(CH₃)CH₂CH₃ | —CH₂CH(CH₃)₂ | —NH₂ |
| 858 | —CH(CH₃)CH₂CH₃ | —CH(CH₃)CH₂CH₃ | —NH₂ |
| 859 | —CH(CH₃)CH₂CH₃ | —CH₂CH₂CH₂NHC(O)CH₂N(CH₃)₂ | —NH₂ |
| 860 | —CH₂C(O)-morpholine | —CH₃ | —NH₂ |
| 861 | —CH₂C(O)-morpholine | —CH₂CH(CH₃)₂ | —NH₂ |

TABLE 8-continued
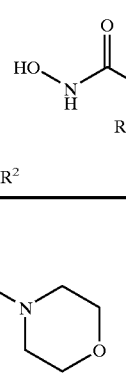
| Example | R² | R³ | R⁴ |
|---|---|---|---|
| 862 | 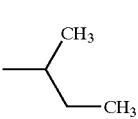 | 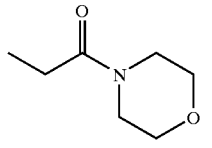 | —NH₂ |
| 863 | 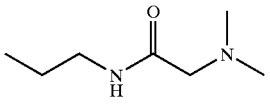 | 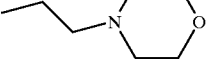 | —NH₂ |
| 864 | 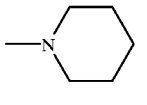 | —CH₃ | 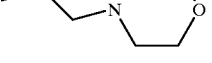 |
| 865 | 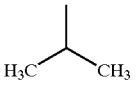 | 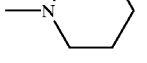 | 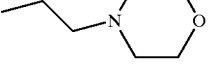 |
| 866 | 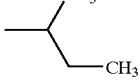 | 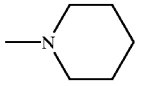 | 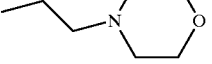 |
| 867 | 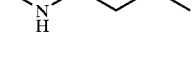 | 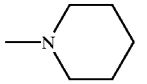 | 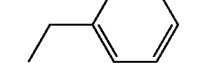 |
| 868 | 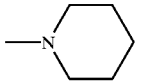 | —CH₃ | 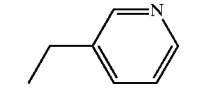 |
| 869 | 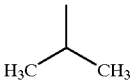 |  | 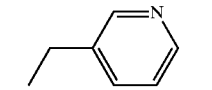 |
| 870 | 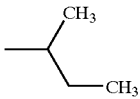 | 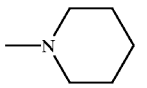 | 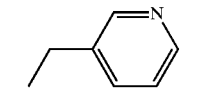 |
| 871 | 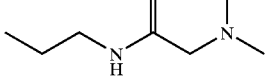 | 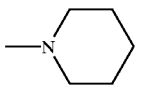 | 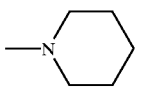 |
| 872 | —CH₃ | —CH₃ | 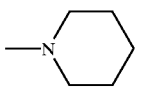 |

TABLE 8-continued
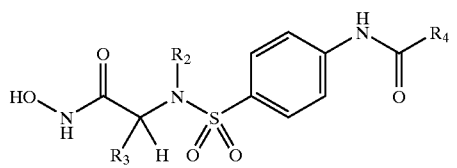

TABLE 8-continued

| Example | R² | R³ | R⁴ |
|---|---|---|---|
| 883 | propionyl-morpholine (ethyl linker) | -CH₂CH₂NHC(O)CH₂N(CH₃)₂ | piperidinyl |
| 884 | propyl-morpholine | —CH₃ | NHCH₃ |
| 885 | propyl-morpholine | isobutyl (CH₂CH(CH₃)₂) | NHCH₃ |
| 886 | propyl-morpholine | sec-butyl (CH(CH₃)CH₂CH₃) | NHCH₃ |
| 887 | propyl-morpholine | -CH₂CH₂NHC(O)CH₂N(CH₃)₂ | NHCH₃ |
| 888 | ethyl-(3-pyridyl) | —CH₃ | NHCH₃ |
| 889 | ethyl-(3-pyridyl) | isobutyl | NHCH₃ |
| 890 | ethyl-(3-pyridyl) | sec-butyl | NHCH₃ |
| 891 | ethyl-(3-pyridyl) | -CH₂CH₂NHC(O)CH₂N(CH₃)₂ | NHCH₃ |
| 892 | —CH₃ | —CH₃ | NHCH₃ |
| 893 | —CH₃ | isobutyl | NHCH₃ |
| 894 | —CH₃ | sec-butyl | NHCH₃ |

TABLE 8-continued

Structure: HO-NH-C(=O)-CH(R3)-N(R2)-S(=O)2-C6H4-NH-C(=O)-R4

| Example | R² | R³ | R⁴ |
|---|---|---|---|
| 895 | —CH₃ | —CH₂CH₂—NH—C(=O)—CH₂—N(CH₃)₂ | —NH—CH₃ |
| 896 | sec-butyl (—CH(CH₃)CH₂CH₃) | —CH₃ | —NH—CH₃ |
| 897 | sec-butyl | isobutyl (—CH₂CH(CH₃)₂) | —NH—CH₃ |
| 898 | sec-butyl | —CH(CH₃)CH₂CH₃ | —NH—CH₃ |
| 899 | isobutyl | —CH₂CH₂—NH—C(=O)—CH₂—N(CH₃)₂ | —NH—CH₃ |
| 900 | —CH₂C(=O)-morpholinyl | —CH₃ | —NH—CH₃ |
| 901 | —CH₂C(=O)-morpholinyl | isobutyl | —NH—CH₃ |
| 902 | —CH₂C(=O)-morpholinyl | —CH(CH₃)CH₂CH₃ | —NH—CH₃ |
| 903 | —CH₂C(=O)-morpholinyl | —CH₂CH₂—NH—C(=O)—CH₂—N(CH₃)₂ | —NH—CH₃ |
| 904 | —CH₂CH₂CH₂-morpholinyl | —CH₃ | 4-biphenyl |
| 905 | —CH₂CH₂CH₂-morpholinyl | isobutyl | 4-biphenyl |

TABLE 8-continued
| Example | R² | R³ | R⁴ |
|---|---|---|---|
| 906 | 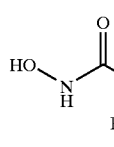 | 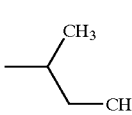 | 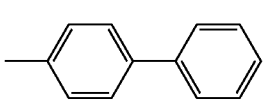 |
| 907 | 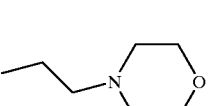 | 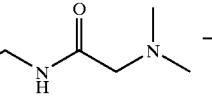 | 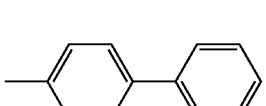 |
| 908 | 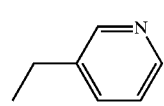 | —CH₃ |  |
| 909 | 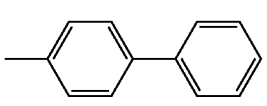 | 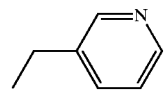 | 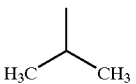 |
| 910 | 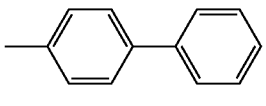 | 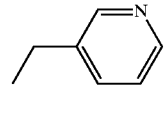 | 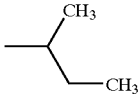 |
| 911 | 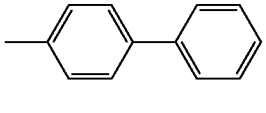 | 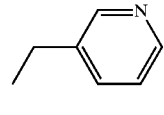 | 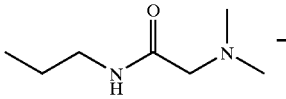 |
| 912 | —CH₃ | —CH₃ | 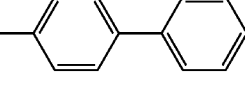 |
| 913 | —CH₃ |  |  |
| 914 | —CH₃ | 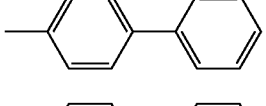 |  |
| 915 | —CH₃ | 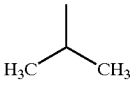 | 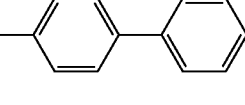 |
| 916 |  | —CH₃ | 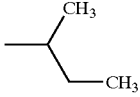 |
| 917 | 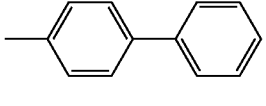 |  | 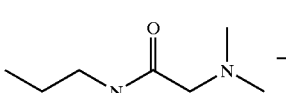 |

TABLE 8-continued

| Example | R² | R³ | R⁴ |
|---|---|---|---|
| 918 | sec-butyl (CH(CH₃)CH₂CH₃) | isobutyl (CH₂CH(CH₃)₂) | 4-biphenyl |
| 919 | isobutyl (CH₂CH(CH₃)₂) | —CH₂CH₂NHC(O)CH₂N(CH₃)₂ | 4-biphenyl |
| 920 | —CH₂CH₂C(O)-morpholine | —CH₃ | 4-biphenyl |
| 921 | —CH₂CH₂C(O)-morpholine | isobutyl (CH(CH₃)₂, H₃C CH₃) | 4-biphenyl |
| 922 | —CH₂CH₂C(O)-morpholine | isobutyl (CH₂CH(CH₃)₂) | 4-biphenyl |
| 923 | —CH₂CH₂C(O)-morpholine | —CH₂CH₂NHC(O)CH₂N(CH₃)₂ | 4-biphenyl |
| 924 | —CH₂CH₂CH₂-morpholine | —CH₃ | 3-pyridyl |
| 925 | —CH₂CH₂CH₂-morpholine | isobutyl (CH(CH₃)₂) | 3-pyridyl |
| 926 | —CH₂CH₂CH₂-morpholine | isobutyl (CH₂CH(CH₃)₂) | 3-pyridyl |
| 927 | —CH₂CH₂CH₂-morpholine | —CH₂CH₂NHC(O)CH₂N(CH₃)₂ | 3-pyridyl |

TABLE 8-continued

[Structure: HO-NH-C(=O)-CH(R3)-N(R2)-SO2-C6H4-NH-C(=O)-R4]

| Example | R² | R³ | R⁴ |
|---------|----|----|----|
| 928 | 3-pyridyl-CH2CH2- | —CH3 | 3-pyridyl |
| 929 | 3-pyridyl-CH2CH2- | isobutyl (H3C-CH(CH3)-CH2-) | 3-pyridyl |
| 930 | 3-pyridyl-CH2CH2- | sec-butyl (CH3-CH(CH3)-CH2-CH3) | 3-pyridyl |
| 931 | 3-pyridyl-CH2CH2- | -CH2CH2CH2-NH-C(=O)-CH2-N(CH3)2 | 3-pyridyl |
| 932 | —CH3 | —CH3 | 3-pyridyl |
| 933 | —CH3 | isobutyl | 3-pyridyl |
| 934 | —CH3 | sec-butyl | 3-pyridyl |
| 935 | —CH3 | -CH2CH2CH2-NH-C(=O)-CH2-N(CH3)2 | 3-pyridyl |
| 936 | sec-butyl | —CH3 | 3-pyridyl |
| 937 | sec-butyl | isobutyl | 3-pyridyl |
| 938 | sec-butyl | sec-butyl | 3-pyridyl |

TABLE 8-continued

| Example | R² | R³ | R⁴ |
|---------|----|----|----|
| 939 | sec-butyl (CH(CH₃)CH₂CH₃) | -CH₂C(O)NH-propyl-N(CH₃)₂ | 3-pyridyl |
| 940 | -CH₂C(O)-morpholinyl | —CH₃ | 3-pyridyl |
| 941 | -CH₂C(O)-morpholinyl | isobutyl (CH₂CH(CH₃)₂) | 3-pyridyl |
| 942 | -CH₂C(O)-morpholinyl | sec-butyl | 3-pyridyl |
| 943 | -CH₂C(O)-morpholinyl | -CH₂C(O)NH-propyl-N(CH₃)₂ | 3-pyridyl |
| 944 | -CH₂CH₂-morpholinyl | —CH₃ | 4-pyridyl |
| 945 | -CH₂CH₂-morpholinyl | isobutyl | 4-pyridyl |
| 946 | -CH₂CH₂-morpholinyl | sec-butyl | 4-pyridyl |
| 947 | -CH₂CH₂-morpholinyl | -CH₂C(O)NH-propyl-N(CH₃)₂ | 4-pyridyl |
| 948 | -CH₂-(3-pyridyl) | —CH₃ | 4-pyridyl |

TABLE 8-continued

| Example | R² | R³ | R⁴ |
|---------|----|----|----|
| 949 | 3-ethylpyridine | isobutyl | 4-pyridyl |
| 950 | 3-ethylpyridine | sec-butyl | 4-pyridyl |
| 951 | 3-ethylpyridine | -CH₂CH₂CH₂NHC(O)CH₂N(CH₃)₂ | 4-pyridyl |
| 952 | —CH₃ | —CH₃ | 4-pyridyl |
| 953 | —CH₃ | isobutyl | 4-pyridyl |
| 954 | —CH₃ | sec-butyl | 4-pyridyl |
| 955 | —CH₃ | -CH₂CH₂CH₂NHC(O)CH₂N(CH₃)₂ | 4-pyridyl |
| 956 | sec-butyl | —CH₃ | 4-pyridyl |
| 957 | sec-butyl | isobutyl | 4-pyridyl |
| 958 | sec-butyl | sec-butyl | 4-pyridyl |
| 959 | sec-butyl | -CH₂CH₂CH₂NHC(O)CH₂N(CH₃)₂ | 4-pyridyl |

TABLE 8-continued

| Example | R² | R³ | R⁴ |
|---|---|---|---|
| 960 | 1-(morpholin-4-yl)propan-1-one-3-yl | —CH₃ | 4-pyridyl |
| 961 | 1-(morpholin-4-yl)propan-1-one-3-yl | isobutyl | 4-pyridyl |
| 962 | 1-(morpholin-4-yl)propan-1-one-3-yl | sec-butyl | 4-pyridyl |
| 963 | 1-(morpholin-4-yl)propan-1-one-3-yl | N-(2-(dimethylamino)acetyl)aminopropyl | 4-pyridyl |
| 964 | 3-(morpholin-4-yl)propyl | —CH₃ | 4-(aminosulfonyl)phenyl |
| 965 | 3-(morpholin-4-yl)propyl | isobutyl | 4-(aminosulfonyl)phenyl |
| 966 | 3-(morpholin-4-yl)propyl | sec-butyl | 4-(aminosulfonyl)phenyl |
| 967 | 3-(morpholin-4-yl)propyl | N-(2-(dimethylamino)acetyl)aminopropyl | 4-(aminosulfonyl)phenyl |
| 968 | 2-(pyridin-3-yl)ethyl | —CH₃ | 4-(aminosulfonyl)phenyl |

TABLE 8-continued
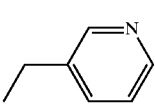
| Example | R² | R³ | R⁴ |
|---|---|---|---|
| 969 | 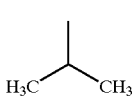 | 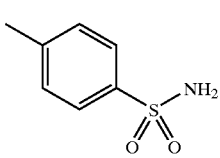 | 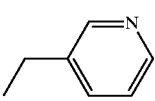 |
| 970 | 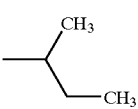 | 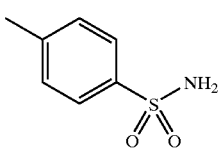 | 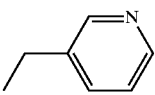 |
| 971 | 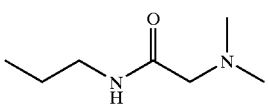 | 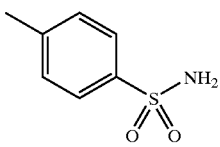 | 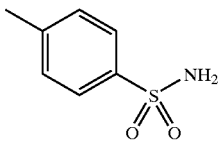 |
| 972 | —CH₃ | —CH₃ | 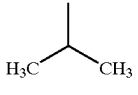 |
| 973 | —CH₃ | 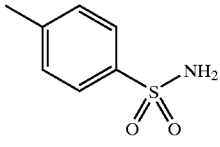 | 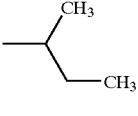 |
| 974 | —CH₃ | 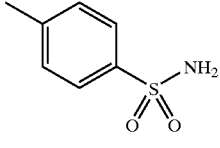 | 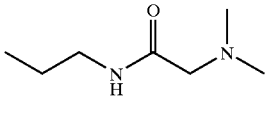 |
| 975 | —CH₃ | 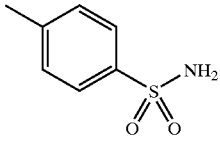 | 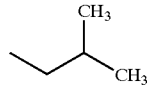 |
| 976 | 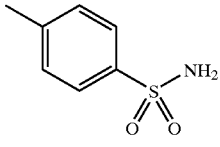 | —CH₃ | |

TABLE 8-continued

| Example | R² | R³ | R⁴ |
|---------|----|----|----|
| 977 | sec-butyl | isobutyl | 4-(SO₂NH₂)phenyl |
| 978 | sec-butyl | isobutyl | 4-(SO₂NH₂)phenyl |
| 979 | sec-butyl | -CH₂C(O)NH-propyl-N(CH₃)₂ (propylamide with dimethylaminomethyl) | 4-(SO₂NH₂)phenyl |
| 980 | 2-(morpholin-4-yl)-2-oxoethyl | —CH₃ | 4-(SO₂NH₂)phenyl |
| 981 | 2-(morpholin-4-yl)-2-oxoethyl | isobutyl | 4-(SO₂NH₂)phenyl |
| 982 | 2-(morpholin-4-yl)-2-oxoethyl | sec-butyl | 4-(SO₂NH₂)phenyl |
| 983 | 2-(morpholin-4-yl)-2-oxoethyl | -CH₂C(O)NH-propyl-N(CH₃)₂ | 4-(SO₂NH₂)phenyl |
| 984 | 2-(morpholin-4-yl)ethyl | —CH₃ | thiazol-5-yl |
| 985 | 2-(morpholin-4-yl)ethyl | isobutyl | thiazol-5-yl |

TABLE 8-continued

| Example | R² | R³ | R⁴ |
|---|---|---|---|
| 986 | propyl-morpholine | sec-butyl | 4-methylthiazole |
| 987 | propyl-morpholine | -CH₂CH₂NHC(O)CH₂N(CH₃)₂ | 4-methylthiazole |
| 988 | ethyl-(3-pyridyl) | —CH₃ | 4-methylthiazole |
| 989 | ethyl-(3-pyridyl) | isobutyl | 4-methylthiazole |
| 990 | ethyl-(3-pyridyl) | sec-butyl | 4-methylthiazole |
| 991 | ethyl-(3-pyridyl) | -CH₂CH₂NHC(O)CH₂N(CH₃)₂ | 4-methylthiazole |
| 992 | —CH₃ | —CH₃ | 4-methylthiazole |
| 993 | —CH₃ | isobutyl | 4-methylthiazole |
| 994 | —CH₃ | sec-butyl | 4-methylthiazole |
| 995 | —CH₃ | -CH₂CH₂NHC(O)CH₂N(CH₃)₂ | 4-methylthiazole |
| 996 | sec-butyl | —CH₃ | 4-methylthiazole |
| 997 | sec-butyl | isobutyl | 4-methylthiazole |

TABLE 8-continued
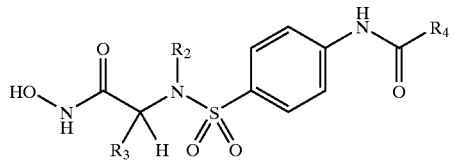
| Example | R² | R³ | R⁴ |
|---|---|---|---|
| 998 | 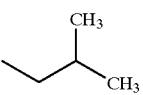 | 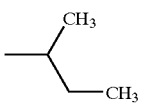 | 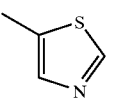 |
| 999 | 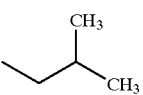 | 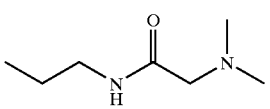 | 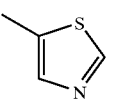 |
| 1000 | 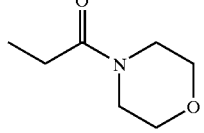 | —CH₃ |  |
| 1001 | 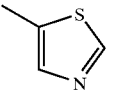 | 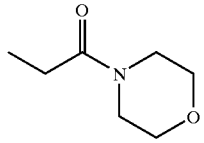 | 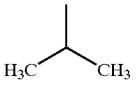 |
| 1002 | 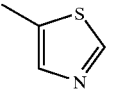 | 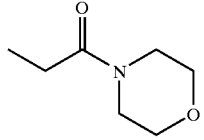 | 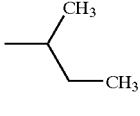 |
| 1003 | 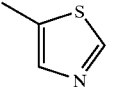 | 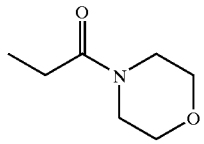 | 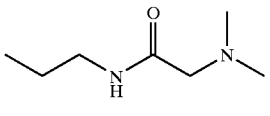 |
| 1004 | 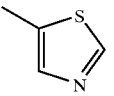 | —CH₃ | 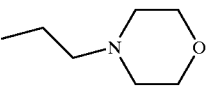 |
| 1005 |  | 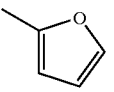 | 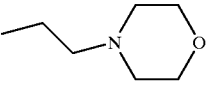 |
| 1006 | 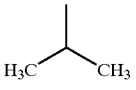 | 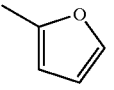 | 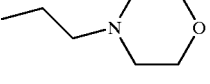 |
| 1007 | 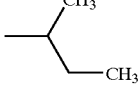 | 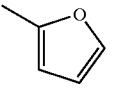 | 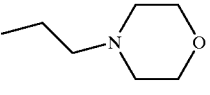 |

TABLE 8-continued
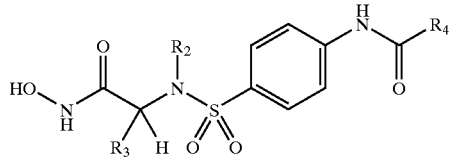
| Example | R² | R³ | R⁴ |
|---|---|---|---|
| 1008 | 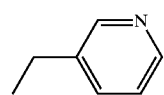 | —CH₃ |  |
| 1009 | 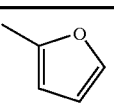 | 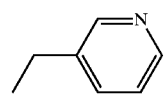 | 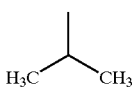 |
| 1010 | 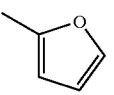 | 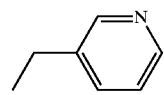 | 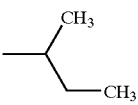 |
| 1011 | 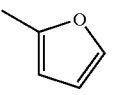 | 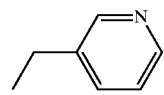 | 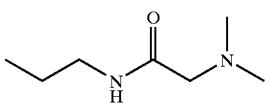 |
| 1012 | —CH₃ | —CH₃ | 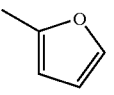 |
| 1013 | —CH₃ |  |  |
| 1014 | —CH₃ | 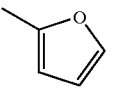 |  |
| 1015 | —CH₃ | 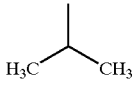 | 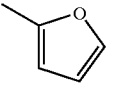 |
| 1016 |  | —CH₃ | 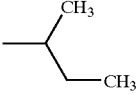 |
| 1017 | 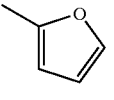 |  | 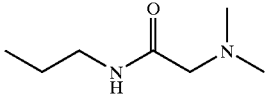 |
| 1018 | 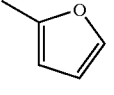 | 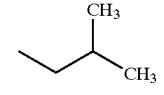 |  |
| 1019 | 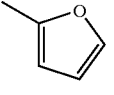 | 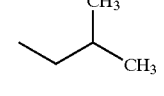 | 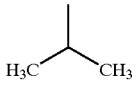 |

TABLE 8-continued

| Example | R² | R³ | R⁴ |
| --- | --- | --- | --- |
| 1020 | 3-(morpholin-4-yl)-3-oxopropyl | —CH₃ | 2-furyl |
| 1021 | 3-(morpholin-4-yl)-3-oxopropyl | isobutyl | 2-furyl |
| 1022 | 3-(morpholin-4-yl)-3-oxopropyl | sec-butyl | 2-furyl |
| 1023 | 3-(morpholin-4-yl)-3-oxopropyl | 3-(N,N-dimethylamino)acetamidopropyl | 2-furyl |
| 1024 | 3-(morpholin-4-yl)propyl | —CH₃ | phenyl |
| 1025 | 3-(morpholin-4-yl)propyl | isobutyl | phenyl |
| 1026 | 3-(morpholin-4-yl)propyl | sec-butyl | phenyl |
| 1027 | 3-(morpholin-4-yl)propyl | 3-(N,N-dimethylamino)acetamidopropyl | phenyl |
| 1028 | 2-(pyridin-3-yl)ethyl | —CH₃ | phenyl |
| 1029 | 2-(pyridin-3-yl)ethyl | isobutyl | phenyl |
| 1030 | 2-(pyridin-3-yl)ethyl | sec-butyl | phenyl |

TABLE 8-continued

| Example | R² | R³ | R⁴ |
|---|---|---|---|
| 1031 | 3-ethylpyridine | -CH₂-C(O)-NH-propyl-N(CH₃)₂ | phenyl |
| 1032 | —CH₃ | —CH₃ | phenyl |
| 1033 | —CH₃ | isobutyl | phenyl |
| 1034 | —CH₃ | sec-butyl | phenyl |
| 1035 | —CH₃ | -CH₂-C(O)-NH-propyl-N(CH₃)₂ | phenyl |
| 1036 | sec-butyl | —CH₃ | phenyl |
| 1037 | sec-butyl | isobutyl | phenyl |
| 1038 | sec-butyl | sec-butyl | phenyl |
| 1039 | sec-butyl | -CH₂-C(O)-NH-propyl-N(CH₃)₂ | phenyl |
| 1040 | propanoyl-morpholine | —CH₃ | phenyl |
| 1041 | propanoyl-morpholine | isobutyl | phenyl |

TABLE 8-continued

| Example | R² | R³ | R⁴ |
|---|---|---|---|
| 1042 | (propionyl-morpholine group) | isobutyl (CH(CH₃)CH₃) | phenyl |
| 1043 | (propionyl-morpholine group) | -CH₂CH₂CH₂-NH-C(O)-CH₂-N(CH₃)₂ | phenyl |

Treatment Process

A process for treating a host mammal having a condition associated with pathological matrix metalloprotease activity is also contemplated. That process comprises administering a metalloprotease inhibitor described hereinbefore in an MMP enzyme-inhibiting effective amount to a mammalian host having such a condition. The use of administration repeated a plurality of times is particularly contemplated.

A contemplated inhibitor compound is used for treating a host mammal such as a mouse, rat, rabbit, dog, horse, primate such as a monkey, chimpanzee or human that has a condition associated with pathological matrix metalloprotease activity.

Also contemplated is the similar use of a contemplated metalloprotease inhibitor compound in the treatment of a disease state that can be affected by the activity of metalloproteases such as TNF-α convertase. Exemplary of such disease states are the acute phase responses of shock and sepsis, coagulation responses, hemorrhage and cardiovascular effects, fever and inflammation, anorexia and cachexia.

In treating a disease condition associated with pathological matrix metalloproteinase activity, a contemplated MMP inhibitor compound can be used, where appropriate, in the form of an amine salt derived from an inorganic or organic acid. Exemplary acid salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl ($C_1$–$C_6$) halides, such as methyl, ethyl, propyl, and butyl chloride, bromides, and iodides; dialkyl sulfates like dimethyl, diethyl, dibuytl, and diamyl sulfates, long chain ($C_8$–$C_{20}$) halides such as decyl, lauryl, myristyl and dodecyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses of an MMP enzyme-inhibiting effective amount can be in amounts, for example, of about 0.001 to about 30 mg/kg body weight daily and more usually about 0.01 to about 10 mg. Dosage unit compositions can contain such amounts or submultiples thereof to make up the daily dose. A suitable dose can be administered, in multiple sub-doses per day. Multiple doses per day can also increase the total daily dose, should such dosing be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound useful in the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Certain of the sulfonamide, sulfinamide or sulfenamide, compounds of this invention that are administered in accordance with an above-discussed process can serve as prodrugs to other compounds of this invention. Prodrugs are drugs that can be chemically converted in vivo or in vitro by biological systems into an active derivative or derivatives. Prodrugs are administered in essentially the same manner as the other pharmaceutical compounds of the invention. Exemplary prodrugs correspond in structure to a compound of formula VII in which $R^{14}$ is acyl.

Preparation of Useful Compounds

Expressly included among the individual compounds of the present invention are carboxylic acid compounds corresponding to each of the hydroxamic acid compounds of Tables 1–8. Each such carboxylic acid compound has the structure depicted for the corresponding hydroxamic acid compound of the tables, except that the carboxylic acid contains an —OH group in the same location in the structure as the HO—NH-group of the hydroxamic acid. Thus, the invention specifically includes a carboxylic acid compound corresponding to each of: Examples 4–17 of Table 1; Examples 18–31 of Table 2; Examples 32–45 of Table 3; Examples 46–59 of Table 4; Examples 4–303 of Table 5; Examples 304–563 of Table 6; Examples 564–763 of Table 7; and Examples 764–1043 of Table 8. The invention also specifically includes the carboxylic acid compounds corresponding to each of working Examples 1–4 that are provided hereinafter.

Schemes I and III and Schemes 1, 2, 4, 5, 6, and 7 illustrate procedures with examples of chemical transformations that may be useful for the preparation of compounds of this invention. These syntheses, as with all of the reactions discussed herein, can be carried out under a dry inert atmosphere such a nitrogen or argon if desired. Selected reactions known to those skilled in the art, can be carried out under a dry atmosphere such as dry air whereas other synthetic steps, for example, aqueous acid or base ester or amide hydrolyses, can be carried out under laboratory air.

Thus, in general, the choices of starting material and reaction conditions can vary as is well know to those skilled in the art. Usually, no single set of conditions is limiting since variations can be applied as required. Conditions will also will be selected as desired to suit a specific purpose such as small scale preparations or large scale preparations. In either case, the use of less safe or less environmentally sound materials or reagents will usually be minimized. Examples of such less desirable materials are diazomethane, diethyl ether, heavy metal salts, dimethyl sulfide, chloroform, benzene and the like.

Scheme 1

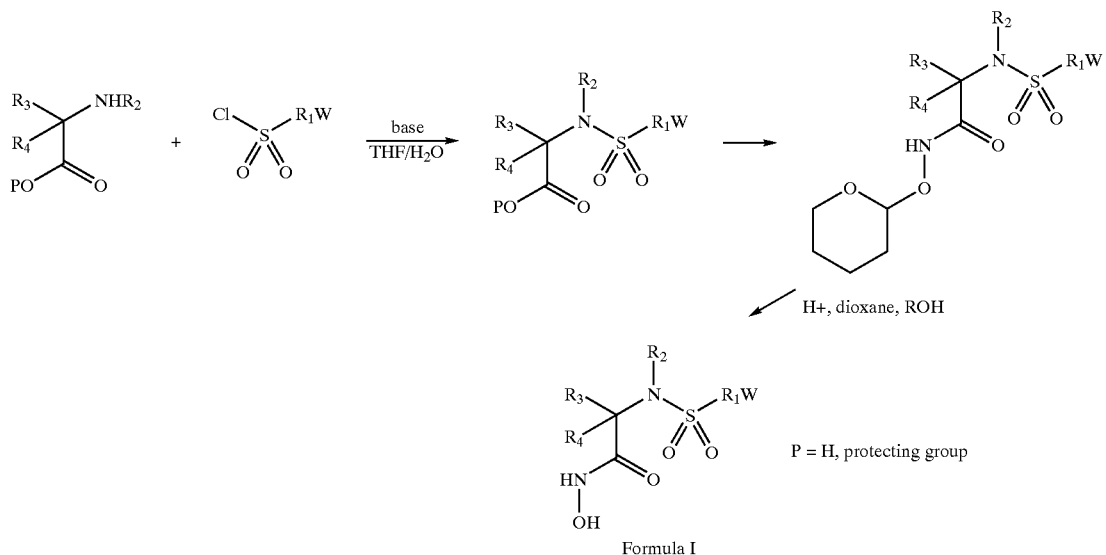

Formula I

P = H, protecting group

Scheme 1 shows the conversion of an N-substituted alpha-amino acid, protected or unprotected, into a compound of Formula I. The amino acid may be protected with a group P such as an alkyl ester such as methyl, ethyl, tert-butyl, tetrahydropyranyl and the like or arylalkyl ester such as benzyl. Treatment of this amine with a sulfonyl, sulfinyl or sulfenyl chloride would provide the corresponding amide. A base would normally be used to inactivate the HCl released from the acid chloride and it would be such that it would not react with the sulfonyl chloride, i.e., ammonia, I° or II° amines would not normally be used. Examples of bases that can be used include, for example, metal hydroxides such as sodium, potassium, lithium or magnesium hydroxide, oxides such as those of sodium, potassium, lithium, calcium or magnesium, metal carbonates such as those of sodium, potassium, lithium, calcium or magnesium, metal bicarbonates such as sodium bicarbonate or potassium bicarbonate, I°, II° or III° organic amines such as alkyl amines, arylalkyl amines, alkylarylalkyl amines, heterocyclic amines or heteroaryl amines, ammonium hydroxides or quaternary ammonium hydroxides. As non-limiting examples, such amines can include triethyl amine, trimethyl amine, diisopropyl amine, methyldiisopropyl amine, diazabicyclononane, tribenzyl amine, dimethylbenzyl amine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine and the like. Non-limiting examples of ammonium hydroxides, usually made from amines and water, can include ammonium hydroxide, triethyl ammonium hydroxide, trimethyl ammonium hydroxide, methyldiiospropyl ammonium hydroxide, tribenzyl ammonium hydroxide, dimethylbenzyl ammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimeth yldiiospropyl ammonium hydroxide, benzymethyldiisopropyl ammonium hydroxide, methyldiazabicyclononyl ammonium hydroxide, methyltribenzyl ammonium hydroxide, N,N-dimethylmorpholinium hydroxide, N,N,N',N'-tetramethylpiperazenium hydroxide, and N-ethyl-N'-hexylpiperidinium hydroxide and the like. Metal hydrides, amide or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide and the like may also be suitable reagents. Organometallic deprotonating agents such as alkyl or aryl lithium reagents such as methyl, phenyl or butyl lithium, Grignard reagents such as methylmagnesium bromide or methymagnesium chloride, organocadium reagents such as dimethylcadium and the like may also serve as bases for causing salt formation or catalyzing the reaction. Quaternary ammonium hydroxides or mixed salts are also useful for aiding phase transfer couplings or serving as phase transfer reagents.

The first reaction in Scheme 1 also illustrated the use of a mixed solvent THF/H$_2$O. This is one solvent system however others may be useful also. For example, the reaction media can consist of a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, isopropanol and the like. Typical non-protic solvents include acetone, tetrahydrofurane (THF), dioxane, diethylether (ether), tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, nitromethane, tetramethylurea, N-methylpyrrolidone and the like.

Scheme 2

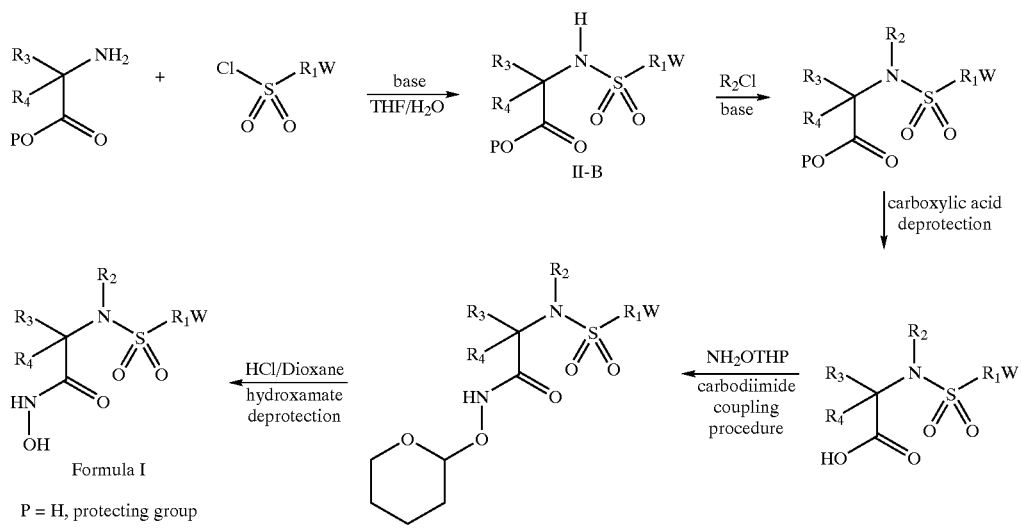

Non-limiting examples of ammonium hydroxides, usually made from amines and water, can include ammonium hydroxide, triethyl ammonium hydroxide, trimethyl ammonium hydroxide, methyldiisopropyl ammonium hydroxide, tribenzyl ammonium hydroxide, dimethylbenzyl ammonium hydroxide, morpholinium hydroxide, N-methylmorpholinium hydroxide, N,N'dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimethyldiisopropyl ammonium hydroxide, benzymethyldiisopropyl ammonium hydroxide, methyldiazabicyclononyl ammonium hydroxide, methyltribenzyl ammonium hydroxide, N,N-dimethylmorpholinium hydroxide, N,N,N', N',-tetramethylpiperazenium hydroxide, and N-ethyl-N'-hexylpiperidinium hydroxide and the like. Metal hydrides, amide or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide and the like may also be suitable reabents. Organometallic deprotonating agents such as alkyl or aryl lithium reagents such as methyl, phenyl or butyl lithium, Grignard reagents such as methylmagnesium bromide or methymagnesium chloride, organocadium reagents such as dimethylcadium and the like may also serve as bases for causing salt formation or catalyzing the reaction. Quaternary ammonium hydroxides or mixed salts are also useful for aiding phase transfer couplings or serving as phase transfer reagents.

The first reaction in Scheme 1 also illustrated the use of a mixed solvent THF/H$_2$O. This is one solvent system however others may be useful also. For example, the reaction media can consist of a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, isopropanol and the like. Typical non-protic solvents include acetone, tetrahydrofurane (THF), dioxane, diethylether (ether), tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, nitromethane, tetramethylurea, N-methylpyrrolidone and the like.

Non-limiting examples of reagents that can be used as solvents or as part of a mixed solvent system include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols, ammonia or amines for making esters or amides and the like.

Acids are used in many reactions during various synthesis. Scheme 1 illustrates acid use for the removal of the THP protecting group to produce the hydroxamic acid of Formula I. The acid might be mono-, di- or tri-protic organic or inorganic acids. Examples of acids include hydrochloric acid, phosphoric acid, sulfuric acid, acetic acid, formic acid, citric acid, succinic acid, hydrobromic acid, hydrofluoric acid, carbonic acid, phosphorus acid, p-toluene sulfonic acid, trifluoromethane sulfonic acid, trifluoroacetic acid, difluoroacetic acid, benzoic acid, methane sulfonic acid, benzene sulfonic acid, 2,6-dimethylbenzene sulfonic acid, trichloroacetic acid, nitrobenzoic acid, dinitrobenzoic acid, trinitrobenzoic acid, and the like. They might also be Lewis acids such as aluminum chloride, borontrifluoride, antimony pentafluoride and the like. A preferred solvent in this type reaction is dioxane eith an alcohol or water however almost any solvent system with one component being a protic solvent can be useful.

Scheme I illustrates conversion of a carboxylic acid protected as an ester or amide into an hydroxamic acid derivative such as a O-arylalkylether or O-cycloalkoxyalkylether group. In particular, the this Scheme the protecting group on the hydroxylamine is the THP group. In the case where hydroxylamine is used, treatment of an ester or amide with one or more equivalents of hydroxylamine hydrochloride at room temperature or above in a solvent or solvents, usually protic or partially protic, such as those listed above can provide a hydroxamic acid directly. This exchange process may be further catalyzed by the addition of additional acid. Alternatively, a base such as a salt of an alcohol used as a solvent, for example, sodium methoxide in methanol, can be used to form hydroxylamine from hydroxylamine hydrochloride in situ which can exchange with an ester or amide. As mentioned above, exchange can be carried out with a protected hydroxyl amine such as tetrahydropyranyl-hydroxyamine (THPONH$_2$), benzylhydroxylamine (BnONH$_2$), and the like in which case compounds such as shown in Scheme 1 that are tetrahydropyranyl (THP) or benzyl (Bn) hydroxamic acid derivatives are the products. Removal of the protecting groups when desired, for example, following further transformations in another part of the molecule or following storage, is accomplished by standard methods well known in the art such as acid hydrolysis of the THP group as discussed above or reductive removal of the benzyl group with hydrogen and a metal catalyst such as palladium, platinum, palladium on carbon or nickel.

In the case where P is hydrogen, i.e., where the intermediate is a carboxylic acid, standard coupling reactions can be used. For example, the acid can be converted into an acid chloride, mixed anhydride or activated ester and treated with hydroxylamine or a protected hydroxylamine in the presence of a non-competitive base to the nitrogen acylated compound. This is the same product as discussed above. Couplings of this nature are well known in the art and especially the art related to peptide and amino acid chemistry.

Scheme II illustrates another possible synthesis of the compounds of Formula I starting with a protected or unprotected amino acid. Sulfonylation of the amino group is accomplished as discussed above to produce the sulfonamide II-B. This compound is a secondary sulfonamide and, as such, is acidic and can be alkylated with an R$^2$ group. Alkylation, a process well known in the art, can be carried by treatment of the sulfonamide with base to form the corresponding anion, adding an electrophilic reagent and allowing the SN$_2$ reaction to proceed. Electrophiles include halogen derivatives, sulfonate esters, epoxides and the like. The bases and solvents discussed with regard to Scheme I are applicable in this Scheme. Preferred bases are those that are hindered such that competition with the electrophile is minimized. Additional preferred bases are metal hydrides, amide anions or organometallic bases such as a butyl lithium. The solvents, solvent mixtures or solvent/reagent mixtures discussed are satisfactory but non-protic or dipolar aprotic solvents such as acetone, acetonitrile, DMF and the like are examples of preferred classes.

Scheme III illustrates the potential for use of a sulfonyl chloride reagent, specifically nitrobenzenesulfonyl chloride, to prepare compounds of this invention. It should be noted that this reagent is for illustration and is not to be considered limiting or required. After coupling with an amino acid and alkylation of the coupling product if required, the nitrosulfonamide can be reduced to provide a useful amino compound. The amino group can be alkylated if desired. It can also be acylated with an aroyl chloride, heteroaryl or other R$^6$ amine carbonyl froming agent to form a —C(=O)— or —S(=O)n— compound of this invention. The amino sulfonamide can also be reacted with a carbonic acid ester chloride as shown in Scheme IV, a sulfonyl chloride as shown in Scheme V or in Scheme VII or a carbamoyl chloride or isocyanate as shown in Scheme VI to produce the corresponding carbamate, sulfonamides, or ureas of this invention. Acylation of amines of this type are well known in the art and the reagents are also well known. Usually these reactions are carried out in aprotic solvents under an inert or/and dry atmosphere at about 45° C. to about −10° C. An equivalent of a non-competitive base is usually used with sulfonyl chloride, acid chloride or carbonyl chloride reagents. Following this acylation step, synthesis of the hydroxamic acid products of this invention can proceed as discussed above for Scheme I and Scheme II.

Schemes II through VI also illustrate the possible reduction of a nitrobenzenesulfonamide to produce an amino sulfonamide. The reduction of nitro groups to amines is will know in the art with a preferred method being hydrogenation. There is usually a metal catalyst such as Rh, Pd, Pt, Ni or the like with or without an additional support such as carbon, barium carbonate and the like. Solvents can be protic or non-protic pure solvents or mixed solvents as required. The reductions can be carried out at atmospheric pressure to a pressure of multiple atmospheres with atmospheric pressure to about 40 pounds per square inch (psi) preferred.

Other sulfonyl chloride reagents can also be used in the preparation of compounds of this invention as outline in the Schemes. Examples are fluoroaryl or fluoroheteroaryl sulfonyl chlorides, azidoaryl or azidoheteroaryl or amide, carbonate, carbamate or urea substituted aryl or heteroaryl sulfonyl chloride reagents. Azides, for example, can be reduced to an amino group using hydrogen with a metal catalyst or metal chelate catalyst or activated hydride transfer reagent. The fluoro substituted sulfonic acid or sulfonamide can be treated with a nucleophile such as ammonia or a primary amine, under pressure if desired, to provide an amino or substituted (R5) amino group that can then be reacted a reagent as outline in Scheme III and in Schemes 4–7 inclusive.

Scheme III

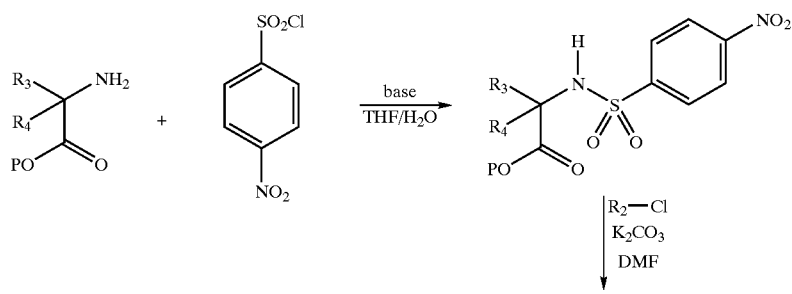

-continued
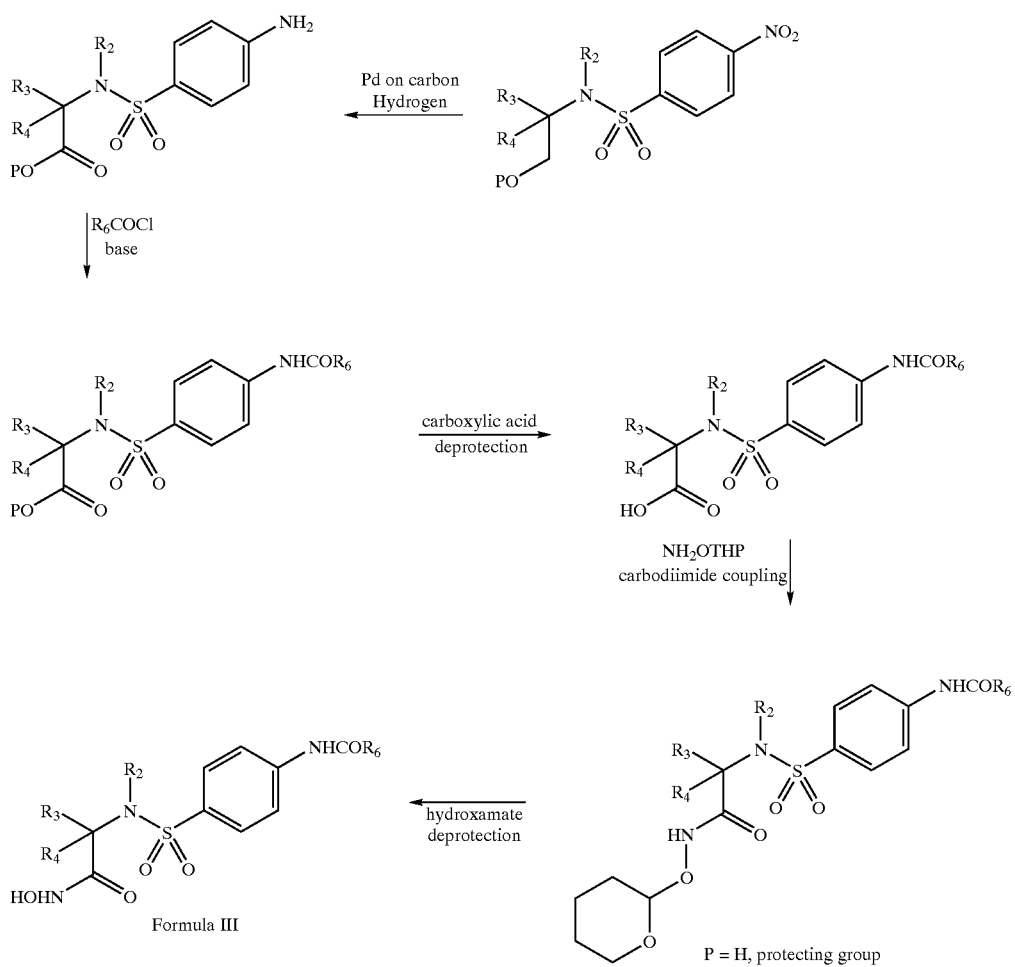
Scheme 4
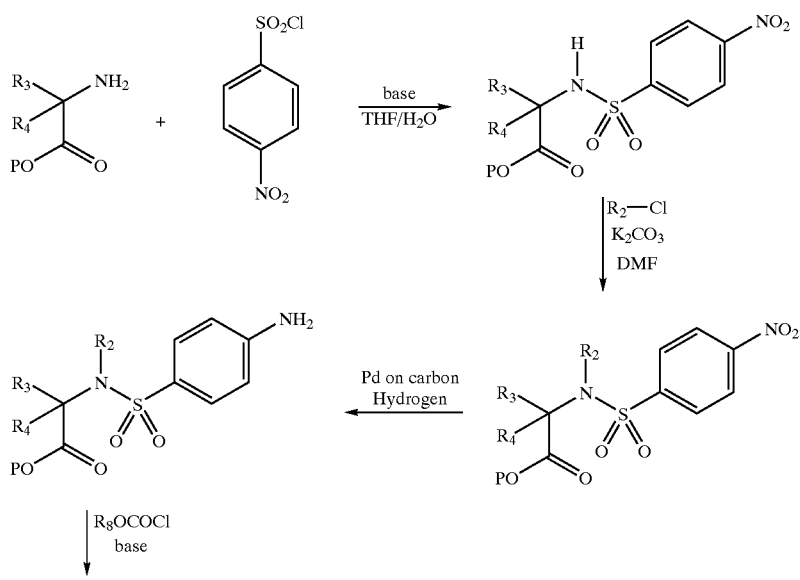

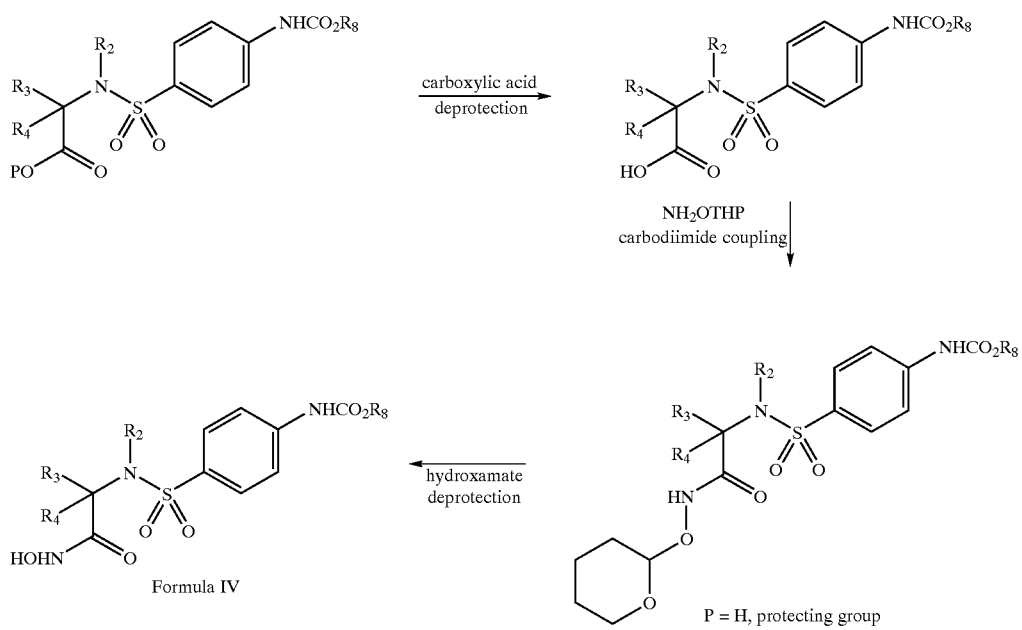
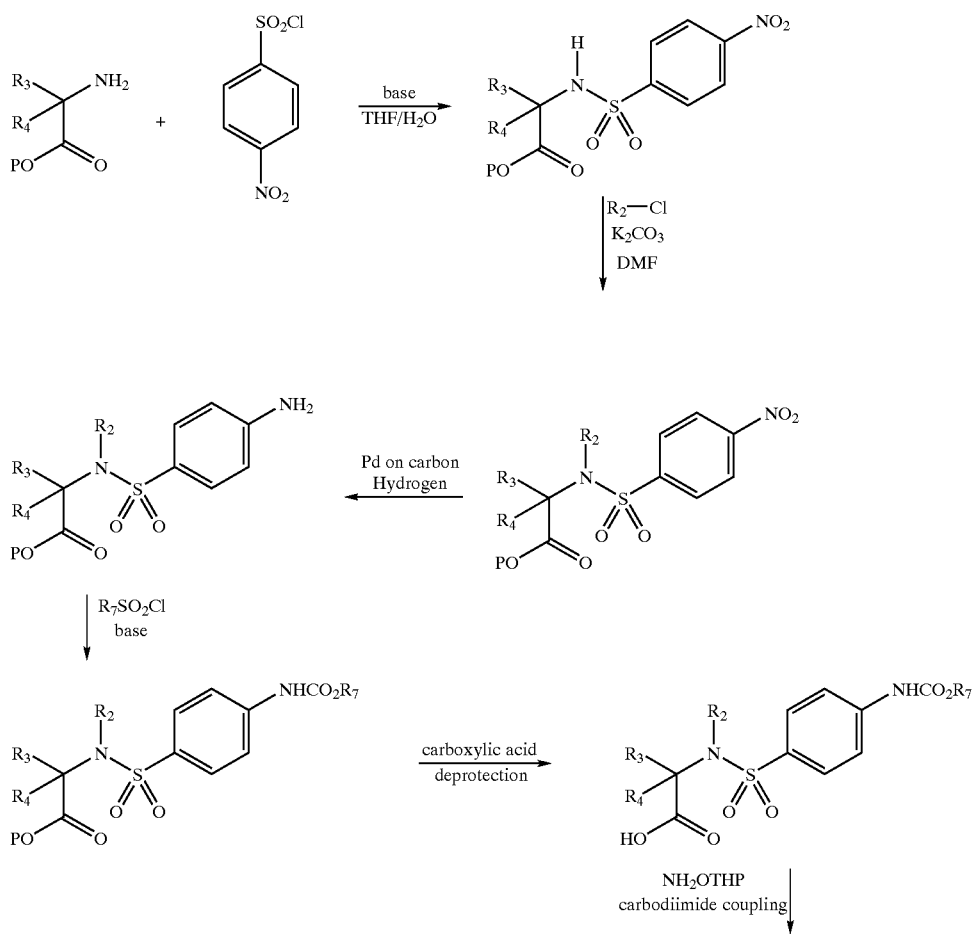
Scheme 5

-continued
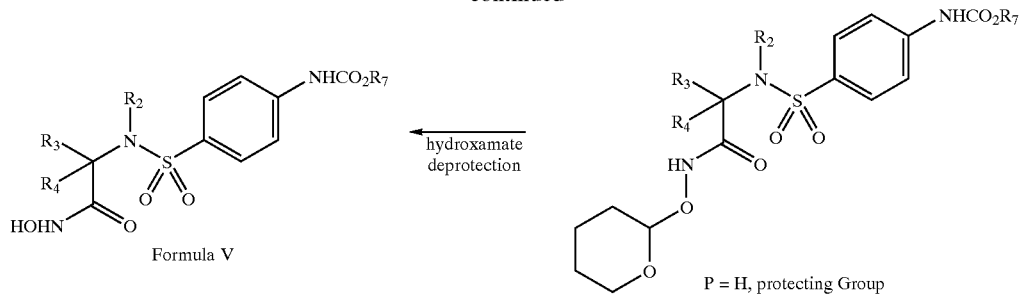
Scheme 6
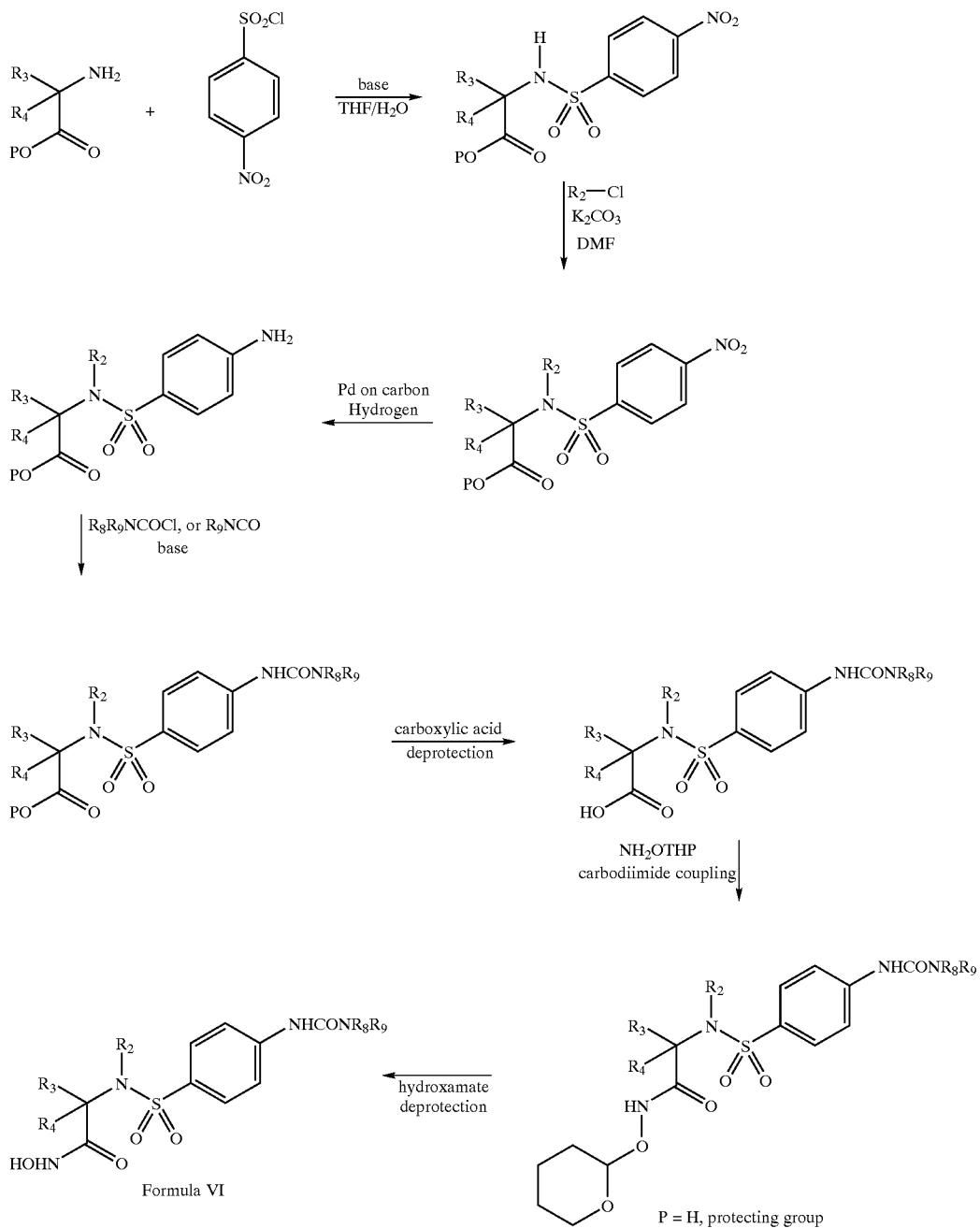

Scheme 7

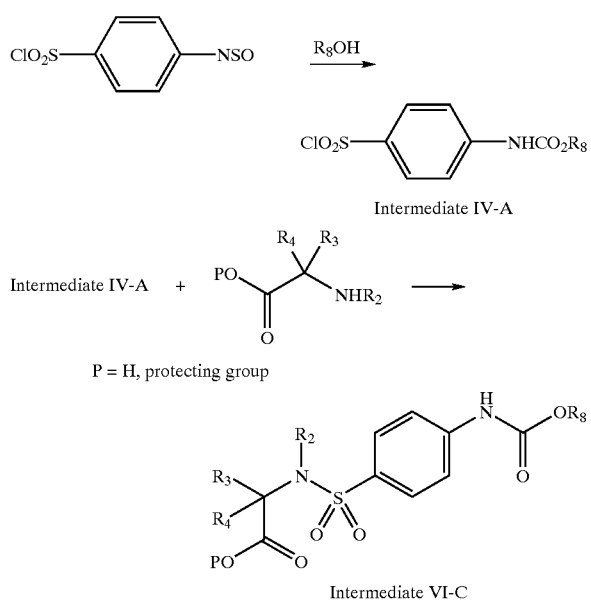

Intermediate VI-C

Compounds of the present can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes well known in the art, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules, e.g., esters, amides, acetals, ketals, and the like, by reacting compounds of Formula I with an optically active acid in an activated form, a optically active diol or an optically active isocyanate. The synthesized diastereoisomers can be separated by conventional means such as chromatography, distillation, crystallization or sublimation, and then hydrolyzed to deliver the enantiomericaly pure compound. In some cases hydrolysis to the parent optically active drug is not necessary prior to dosing the patient since the compound can behave as a prodrug. The optically active compounds of Formula I can likewise be obtained by utilizing optically active starting materials.

Contemplated equivalents of the general formulas set forth above for the MMP inhibitor compounds and derivatives as well as the intermediates are compounds otherwise corresponding thereto and having the same general properties such as tautomers thereof and compounds wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure. For example, two hydroxyl groups, two amino groups, two thiol groups or a mixture of two hydrogen-heteroatom groups on the same carbon are know not to be stable without protection or as a derivative.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

BEST MODE FOR CARRYING OUT THE INVENTION

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLE 1

N-Hydroxy-2(R)-[[(4-benzoylamino)benzenesulfonyl][(4-ethylmorpholino)amino]-3-methylbutanamide, Hydrochloride

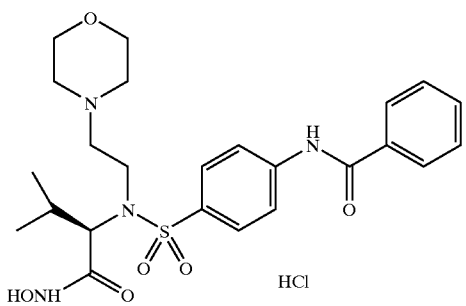

Part A: To a stirred solution of D-valine (10.0 g) in a 2:1 mixture of THF/water (200 mL) containing 3 equiv. of triethylamine at 5° C. is added 4-(benzoylamino)benzenesulfonyl chloride (0.9 equiv.) and the reaction is stirred to room temperature overnight. The resulting mixture is diluted with dichloromethane, and washed with 1N HCl, and water. The organic layer is dried over magnesium sulfate, filtered and concentrated in vacuo to provide the desired N-[(4-benzoylamino)benzenesulfonyl]-(D)-valine as a crude product. A solution of the crude acid (10 grams) in 80 mL of dry toluene is charged with dimethylformamide di-tert-butylacetal (45 mL) and heated to 100° C. for several hours. The resulting cooled solution is concentrated by rotary evaporation and purified by silica gel chromatography to provide the desired N-[(4-benzoylamino)benzenesulfonyl]-(D)-valine, tert-butyl ester.

Part B: To a dimethylformamide solution (100 mL) of the tert-butyl ester from Part A (5.0 grams) is added 4-(2- chloroethyl)-morpholine hydrochloride (1.3 equivalents) and potassium carbonate (3 equivalents); this suspension is heated to 70° C. for five hours. The resulting suspension is cooled and diluted with water (500 mL) and extracted with ethyl acetate. The organic layer is washed with water (2×200 mL), saturated sodium bicarbonate (2×200 mL), and brine, dried over magnesium sulfate, filtered and concentrated to yield the desired product, t-butyl 2(R)-[[(4-benzoylamino) benzenesulfonyl][(4-ethylmorpholino)amino]-3-methylbutanoate, which can be purified by silica gel chromatography.

Part C: t-Butyl 2(R)-[[(4-benzoylamino)benzenesulfonyl] [(4-ethylmorpholino)amino]-3-methylbutanoate from Part A (4.0 grams) in 100 mL of anhydrous dichloromethane, is cooled to −50° C., and dry HCl gas is bubbled into the reaction flask for 20 minutes. The flask is the sealed and allowed to warm to room temperature over three to four hours. The solvent is removed by rotary evaporation and the desired acid, hydrochloride salt, (2(R)-[[(4-benzoylamino) benzenesulfonyl][(4-ethylmorpholino)amino]-3-methylbutanoic acid hydrochloride) is triturated with ether hexane and filtered. The dried precipitate is used without further purification.

Part D: 2(R)-[[(4-benzoylamino)benzene-sulfonyl][(4-ethylmorpholino)amino]-3-methylbutanoic acid hydrochloride from Part C (3.8 grams) and 1-hydroxybenzotriazole (1.5 equivalents) are dissolved in anhydrous dimethylformamide (50 mL) and cooled to 10° C. To this is added N-methylmorpholine (3 equivalents) followed by EDC (1.1 equivalents) and this solution is stirred for two hours at 10° C. To this is added O-tetrahydropyranyl (O-THP) hydroxylamine (2 equivalents) and the solution is stirred overnight at room temperature. The resulting mixture is diluted with 200 mL of water and extracted with ethyl acetate. The organic layer is washed with saturated sodium bicarbonate and brine, dried over magnesium sulfate, filtered and concentrated to yield the desired O-THP-protected hydroxamate, N-tetrahydropyranyloxy-2(R)-[[(4-benzoylamino)-benzenesulfonyl][(4-ethylmorpholino)-amino]-3-methylbutanamide. Further purification by silica gel chromatography provides a mixture of desired diastereomers which are combined.

N-tetrahydropyranyloxy-2(R)-[[(4-benzoylamino)-benzenesulfonyl][(4-ethylmorpholino)amino]-3-methylbutanamide (4.0 grams), is dissolved in a solution of dioxane(150 mL), and ethanol (1 mL) and cooled to −5° C. To this is added HCl (5 equivalents; 4N in dioxane) and the solution is stirred for one hour. The contents are concentrated and the desired product is triturated from ether/hexane and filtered to yield the desired N-hydroxy-2(R)-[[(4-benzoylamino)benzenesulfonyl]-[(4-ethylmorpholino)-amino]-3-methylbutanamide, hydrochloride.

EXAMPLE 2

N-Hydroxy-2(R)-[[(4-benzoylamino) benzenesulfonyl][(3-picolyl)amino]propanamide

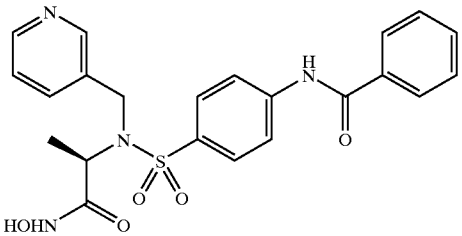

Part A: To a solution of D-alanine methyl ester hydrochloride (6.0 grams) in methanol (25 mL) is added 1.1 equivalents of 3-Pyridinecarboxaldehyde. The solution is stirred at room temperature for several hours and then the solvent removed by rotary evaporation. The resulting imine is redissolved in acetic acid (10 mL) and methanol (2 mL), and sodium cyanoborohydride (1.5 equivalents) is added in several portions over 10 minutes. The mixture is then stirred for 16 hours and then concentrated by rotary evaporation. The resulting residue is partitioned between ethyl acetate and aqueous sodium carbonate (10%). The organic layer is dried over magnesium sulfate, filtered and concentrated to yield the desired N-3-picolyl-D-alanine methyl ester.

Part B: To a stirred solution of N-3-picolyl-D-alanine methyl ester (5.0 g) in a 2:1 mixture of THF/water (200 mL) containing triethylamine (3 equiv.) at 5° C. is added 4-(benzoylamino)benzenesulfonyl chloride and the reaction is stirred to room temperature overnight. The resulting mixture is diluted with dichloromethane, and washed with 1 N HCl, and water. The organic layer is dried over magnesium sulfate, filtered and concentrated in vacuo to provide the desired methyl 2(R)-[[(4-benzoylamino) benzenesulfonyl][(3-picolyl)amino]propionate as a crude product, which may be purified by silica gel chromatography using ethyl acetate/hexanes as eluant.

Part C: To a solution of methyl ester from Part B (2.0 grams) in tetrahdrofuran (100 mL) is added a solution of aqueous 1N sodium hydroxide (1.2 equiv.) and the reaction mixture is stirred for 20 hours. The solvents are removed by rotary evaporation and the remaining oil is partitioned between ethyl acetate and 1N hydrochloric acid. The organic layer is separated and dried over magnesium sulfate, filtered and concentrated to yield 2(R)-[[(4-benzoylamino)-benzenesulfonyl][(3-picolyl)amino]propionic-acid.

2(R)-[[(4-benzoylamino)benzenesulfonyl]-[(3-picolyl) amino]propionic acid (1.3 grams) and 1-hydroxybenzotriazole (1.5 equivalents) are dissolved in anhydrous dimethylformamide (25 mL) and cooled to 10° C. To this is added N-methylmorpholine (3 equivalents) followed by EDC (1.1 equivalents) and this solution is stirred for two hours at 10° C. To this solution is added O-tetrahydropyranyl hydroxylamine (2 equivalents) and this solution is stirred overnight to room temperature. The solution is diluted with water (100 mL) and extracted with ethyl acetate. The organic layer is washed with saturated sodium bicarbonate and brine, dried over magnesium sulfate, filtered and concentrated to yield the desired O-THP protected hydroxamate which is further purified by silica gel chromatography to give a mixture of desired diastereomers which are combined.

N-tetrahydropyranyloxy-2(R)-[[(4-benzoylamino)-benzenesulfonyl][(3-picolyl)amino]-propanamide (1.0 gram), is dissolved in a solution of dioxane (50 mL), and ethanol (1 mL) and cooled to −50° C. To this is added 5 equivalents of HCl (4N in dioxane) and the solution is stirred for one hour. The contents are concentrated and the desired product is triturated with ether/hexane and filtered to yield the desired N-hydroxy-2(R)-[[(4-benzoylamino)benzenesulfonyl]-[(3-picolyl)amino]propanamide, hydrochloride. This crude product may be purified by silica gel chromatography using methanol and methylene chloride as the eluant, after neutralization to the free base.

EXAMPLE 3

N-Hydroxy-2(R)-[[(4-(benzenesulfonyl)amino)-benzenesulfonyl][(4-ethylmorpholino)amino]-3-methylbutanamide, Hydrochloride

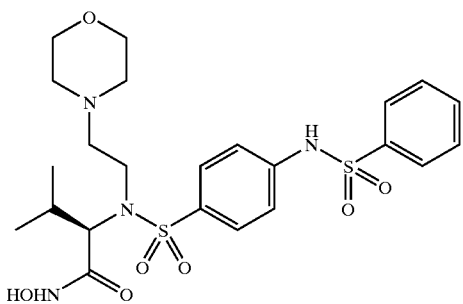

Part A: To a stirred solution of D-valine (10.0 g) in a 2:1 mixture of THF/water (200 mL) containing triethylamine (3 equiv.) at 50° C. is added 4-nitrobenzene-sulfonyl chloride (0.9 equiv.) and the reaction is stirred at room temperature overnight. The resulting mixture is diluted with dichloromethane, and washed with 1N HCl, and water. The organic layer is dried over magnesium sulfate, filtered and concentrated in vacuo to provide the desired N-(nitrobenzenesulfonyl)-(D)-valine as a crude amino acid product. A solution of the crude amino acid (10 grams) in dry toluene (80 mL) is charged with dimethylformamide di-tertbutylacetal (45 mL) and heated to 100° C. for several hours. The resulting cooled solution is concentrated by rotary evaporation and purified by silica gel chromatography to provide the desired N-(4-nitrobenzenesulfonyl)-(D)-valine, tert-butyl ester.

Part B: To a dimethylformamide solution (100 mL) of the tert-butyl ester from Part A (5.0 grams) is added 4-(2-chloroethyl)-morpholine hydrochloride (1.3 equivalents) and potassium carbonate (3 equivalents); and this suspension is heated to 70° C. for five hours. The resulting suspension is cooled and diluted with water (500 mL) and extracted with ethyl acetate. The organic layer is washed with water (2×200 mL), saturated sodium bicarbonate (2×200 mL), and brine, dried over magnesium sulfate, filtered and concentrated to yield the desired product, t-butyl 2(R)-[4-nitrobenzenesulfonyl][(4-ethylmorpholino)amino]-3-methylbutanoate, which can be purified by silica gel chromatography.

Part C: t-Butyl 2(R)-[4-nitrobenzene-sulfonyl][(4-ethylmorpholino)amino]-3-methylbutanoate (1.5 grams) is added to a Fisher® porter bottle containing ethanol/THF (50 mL each) and 200 mg of 10% palladium on carbon. The bottle is flushed with nitrogen while stirring and then charged with hydrogen at a pressure of 50 psig. After one hour the bottle is flushed with nitrogen and the resulting suspension is filtered through Celite. The filtrate is concentrated to yield t-butyl 2(R)-[4-aminobenzenesulfonyl]-[(4-ethylmorpholino)amino]-3-methylbutanoate.

Part D: To a solution of t-butyl 2(R)-[4-aminobenzenesulfonyl]-[(4-ethylmorpholino)amino]-3-methylbutanoate from Part C (1.30 grams) in tetrahydrofuran containing N-methylmorpholine (1.2 equivalents) is added benzenesulfonyl chloride (1.0 equivalents); this solution was stirred for 16 hours. The contents were diluted with ethyl acetate and washed with 5% KHSO$_4$, saturated sodium bicarbonate and brine, dried over magnesium sulfate, filtered and concentrated to yield the desired t-butyl-2(R)-[[(4-(benzenesulfonyl)amino)-benzenesulfonyl][(4-ethylmorpholino)amino]-3-methylbutanoate (1.5 grams).

Part E: t-Butyl-2(R)-[[(4-(benzenesulfonyl)amino)-benzenesulfonyl][(4-ethylmorpholino)amino]-3-methylbutanoate from Part D (1.3 grams) in 50 mL of anhydrous dichloromethane is cooled to −5° C., and dry HCl gas is bubbled into the reaction flask for 20 minutes. The flask is the sealed and allowed to warm to room temperature over three to four hours. The solvent is removed by rotary evaporation and the desired acid, hydrochloride salt is triturated with ether hexane and filtered. The dried precipitate is used without further purification.

t-Butyl-2(R)-[[(4-(benzenesulfonyl)amino)-benzenesulfonyl][(4-ethylmorpholino)amino]-3-methylbutanoate (1.0 grams) and 1-hydroxybenzotriazole (1.5 equivalents) are dissolved in anhydrous dimethylformamide (25 mL) and cooled to 10° C. To this is added N-methylmorpholine (3 equivalents) followed by EDC (1.1 equivalents) and this solution is stirred for two hours at 10° C. To this solution is added O-tetrahydropyranyl (0-THP) hydroxylamine (2 equivalents); this solution is stirred overnight at room temperature. The solution is diluted with water (100 mL) and extracted with ethyl acetate. The organic layer is washed with saturated sodium bicarbonate and brine, dried over magnesium sulfate, filtered and concentrated to yield the desired O-THP-protected hydroxamate which is further purified by silica gel chromatography to give a mixture of desired diastereomers which are combined.

N-tetrahydropyranyloxy-2(R)-[[(4-(benzenesulfonyl)-amino)benzenesulfonyl][(4-ethylmorpholino)amino]-3-methylbutanoic acid (0.80 grams), is dissolved in a solution of dioxane (20 mL), and ethanol (1 mL) and cooled to −5° C. To this is added HCl (5 equivalents; 4N in dioxane) and the solution is stirred for one hour. The contents are concentrated and the desired product is triturated from ether/hexane and filtered to yield the desired N-hydroxy-2(R)-[[(4-(benzenesulfonyl)amino)benzenesulfonyl][(4-ethylmorpholino)amino]-3-methylbutanamide, hydrochloride. This crude product may be purified by silica gel chromatography using methanol and methylene chloride as the eluant, on the free base.

EXAMPLE 4

(R)-N-[4-[[[2-(Hydroxyamino)-1-methyl-2-oxoethyl][2-(4-morpholinyl)ethyl]amino]sulfonyl]phenyl]benzamide

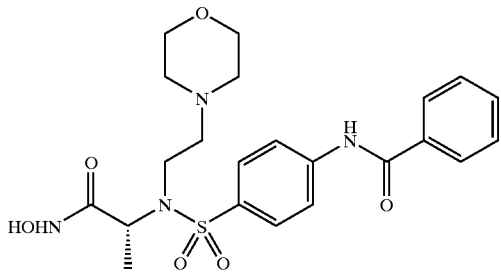

Part A: To a solution of D-alanine, t-butyl ester hydrochloride (9.80 g, 53.9 mmol) in $H_2O$ (64 mL) and acetone (26 mL) was added triethylamine (17.3 mL, 124 mmol) and the solution was cooled to zero degrees Celsius. To this solution was added 4-nitrobenzenesulfonyl chloride (11.1 g, 50.2 mmol) dropwise in acetone (25 mL). The solution was stirred for 72 hours. The solution was concentrated in vacuo and the residue was dissolved into ethyl acetate. The solution was washed with 5% $KHSO_4$, saturated $NaHCO_3$ and saturated NaCl and dried over $Na_2SO_4$. Recrystallization (ethyl acetate/hexane) provided the sulfonamide as a solid (10.87 g, 66%).

Part B: To a solution of the sulfonamide of part A (10.8 g, 32.7 mmol) in DMF (60 mL) was added 4-(2-chloroethyl)morpholine (12.2 g, 65.4 mmol) and $K_2CO_3$ (13.6 g, 98.0 mmol) and the solution was heated to seventy degrees Celsius for 7 hours. The solution was partitioned between ethyl acetate and $H_2O$. The organic layer was washed with $H_2O$, saturated NaCl and dried over $Na_2SO_4$. Concentration in vacuo followed by tritration (ethyl ether) provided the morpholine compound as a solid (8.48 g, 59%). MS(CI) $MH^+$ calculated for $C_{19}H_{29}N_3O_7S$: 444, found: 444.

Part C: To a solution of the morpholine compound of part B (8.49 g, 19.1 mmol) in THF (100 mL) under atmosphere of 50 psi of hydrogen was added 4% Pd/C and the solution was stirred for 2 hours until uptake stopped. The solution was filtered through Celite and concentration in vacuo of the filtrate provided the aniline as a solid (8.5 g, quantitative yield). MS(CI) $MH^+$ calculated for $C_{19}H_{31}N_3O_5S$: 414, found: 414.

Part D: To a solution of the aniline of part C (2.0 g, 4.8 mmol) in THF (16 mL) was added triethylamine (3.0 mL, 21.3 mmol) and the solution was cooled to zero degrees Celsius. To this solution was added benzoyl chloride (1.46 mL, 12.6 mmol) and the solution was stirred for 18 hours at ambient temperature. The solution was concentrated in vacuo and the residue was partitioned between ethyl acetate and saturated $NaHCO_3$. The organic layer was washed with saturated NaCl and dried over $Na_2SO_4$. Chromatography (on silica gel, ethyl acetate/methanol) provided the benzamide as a solid (2.0 g, 80%). MS(CI) $MH^+$ calculated for $C_{26}H_{35}N_3O_6S$: 518, found: 518.

Part E: To a solution of the benzamide of part D (2.0 g, 3.9 mmol) in anisole (9 mL) was added trifluoroacetic acid (26 mL) and the solution was stirred for 18 hours. The solution was concentrated in vacuo to remove the trifluoroacetic acid. The remaining solution was poured into ethyl ether and the resulting solid was collect by vacuum filtration to provide the acid as a white solid (1.09 g, 50%) MS(CI) $MH^+$ calculated for $C_{22}H_{27}N_3O_6S$: 462, found: 462.

Part F: To a solution of the acid of part E (1.09 g, 1.89 mmol) in methanol (3 mL) cooled to zero degrees Celsius was added thionyl chloride (0.18 mL, 2.4 mmol) and the solution was stirred at ambient temperature for 18 hours. The solution was partitioned between ethyl acetate and saturated $NaHCO_3$. The organic layer was washed with saturated $NaHCO_3$ and saturated NaCl and dried over $Na_2SO_4$. Reverse phase chromatography (on silica; acetonitrile/$H_2O$) provided the methyl ester as a white solid (650 mg, 72%). MS(CI) $MH^+$ calculated for $C_{23}H_{29}N_3O_6S$: 476, found: 476.

Part G: To a solution of the methyl ester of part F (650 mg, 1.4 mmol) in methanol (1.6 mL) and THF (1.6 mL) was added 50% aqueous hydroxylamine (1.6 mL). The solution was stirred for 18 hours. The solution was concentrated in vacuo and the residue was partitioned between ethyl acetate and $H_2O$. The organic layer was washed with saturated NaCl and dried over $Na_2SO_4$. Concentration in vacuo provided (R)—N-[4-[[[2-(hydroxyamino)-1-methyl-2-oxoethyl][2-(4-morpholinyl)ethyl]amino]sulfonyl]phenyl]benzamide as a white solid (380 mg, 58%). MS(CI) $MH^+$ calculated for $C_{22}H_{28}N_4O_6S$: 477, found: 477.

EXAMPLE 4a (R)-N-[4-[[[2-(Hydroxyamino)-1-methyl-2-oxoethyl][2-4-morpholinyl)ethyl]amino]sulfonyl]phenyl]benzamide, Monohydrochloride

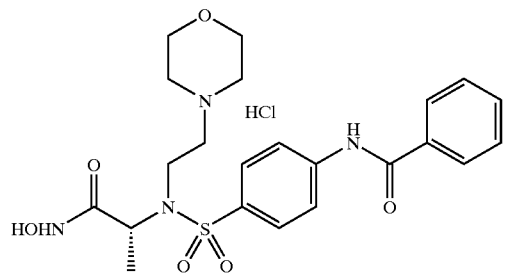

To solution of N-hydroxy-2(R)-[[(4-benzoylamino)benzenesulfonyl][(4-ethylmorpholino)amino]-3-methylbutanamide, hydrochloride of Example 1 (380 mg, 0.8 mmol) in acetonitrile (30 mL) was added (0.13 mL; 1.59 mmol) 12N HCl and the solution was stirred for 10 minutes. The solution was concentrated in vacuo and the residue was triturated with ethyl ether to provide the hydrochloride salt as a white solid (349 mg, 85%). MS(CI) $MH^+$ calculated for $C_{22}H_{28}N_4O_6S$: 477, found: 477.

EXAMPLE 5

(R)-4-Bromo-N-[4-[[[2-(hydroxyamino)-1-methyl-2-oxoethyl][2-(4-morpholinyl)ethyl]amino]sulfonyl]phenyl]benzamide, Mono(trifluoroacetate) (Salt)

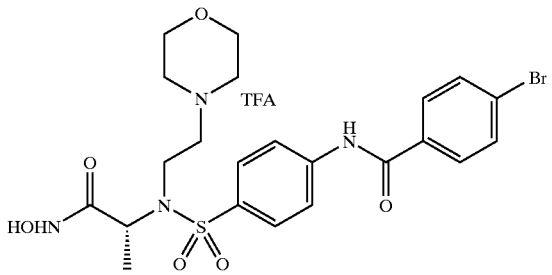

Part A: To a solution of D-alanine, t-butyl ester hydrochloride (9.80 g, 53.9 mmol) in $H_2O$ (64 mL) and acetone (26 mL) was added triethylamine (17.3 mL, 124 mmol) and the solution was cooled to zero degrees Celsius. To this solution was added 4-nitrobenzenesulfonyl chloride (11.1 g, 50.2 mmol) dropwise in acetone (25 mL). The solution was stirred for 72 hours. The solution was concentrated in vacuo and the residue was dissolved into ethyl acetate. The solution was washed with 5% $KHSO_4$, saturated $NaHCO_3$ and saturated NaCl and dried over $Na_2SO_4$. Recrystallization (ethyl acetate/hexane) provided the sulfonamide as a solid (10.87 g, 66%).

Part B: To a solution of the sulfonamide of part A (10.8 g, 32.7 mmol) in DMF (60 mL) was added 4-(2-chloroethyl)morpholine (12.2 g, 65.4 mmol) and $K_2CO_3$ (13.6 g, 98.0 mmol) and the solution was heated to seventy degrees Celsius for 7 hours. The solution was partitioned between ethyl acetate and $H_2O$. The organic layer was washed with $H_2O$, saturated NaCl and dried over $Na_2SO_4$. Concentration in vacuo followed by tritration (ethyl ether) provided the morpholine compound as a solid (8.48 g, 59%). MS(CI) $MH^+$ calculated for $C_{19}H_{29}N_3O_7S$: 444, found: 444.

Part C: To a solution of the morpholine compound of part B (8.49 g, 19.1 mmol) in THF (100 mL) under atmosphere of 50 psi of hydrogen was added 4% Pd/C and the solution was stirred for 2 hours until uptake stopped. The solution was filtered through Celite and concentration in vacuo of the filtrate provided the aniline as a solid (8.5 g, quantitative yield). MS(CI) $MH^+$ calculated for $C_{19}H_{31}N_3O_5S$: 414, found: 414.

Part D: To a solution of the aniline of part C (2.84 g, 6.87 mmol) in THF (40 mL) cooled to zero degrees Celsius was added triethylamine (2.1 mL, 15.1 mmol) followed by 4-bromobenzoyl chloride (1.96 g, 9.93 mmol) in THF (5 mL). The solution was stirred at zero degrees Celsius for 1 hour. The solution was concentrated in vacuo and the residue was partitioned between ethyl acetate and saturated $NaHCO_3$ and the organic is washed with saturated NaCl and dried over $Na_2SO_4$. Chromatography (on silica gel, ethyl acetate/methanol) provided the benzamide as a solid (3.3 g, 81%). MS(CI) $MH^+$ calculated for $C_{26}H_{34}N_3O_6SBr$: 596, found: 596.

Part E: To a solution of the benzamide of part D (2.84 g, 4.76 mmol) in anisole (11 mL) was added trifluoroacetic acid (32 mL) and the solution was stirred at ambient temperature for 18 hours. The solution was concentrated in vacuo to remove the trifluoroacetic acid and the residue was poured into ethyl ether. Filtration provided the acid as an off-white solid (2.8 g, quantitative yield). MS(CI) $MH^+$ calculated for $C_{22}H_{26}N_3O_6SBr$: 541, found 541.

Part F: To a solution of the acid of part E (2.71 g, 4.14 mmol) in methanol (10 mL) cooled to zero degrees Celsius was added thionyl chloride (0.38 mL, 5.25 mmol). The solution was stirred for 18 hours at ambient temperature. The solution was partitioned between ethyl acetate and saturated $NaHCO_3$ and the organic layer was washed with saturated NaCl and dried over $Na_2SO_4$. Chromatography (on silica, ethyl acetate/methanol) provided the methyl ester as a solid (1.96 g, 85%).

Part G: To a solution of the methyl ester of part F (1.96 g, 3.53 mmol) in THF (2 mL) and methanol (2 mL) was added 50% aqueous hydroxylamine (4.2 mL, 70.7 mmol) was added and the solution was stirred for 18 hours at ambient temperature. The solution was concentrated in vacuo and reverse phase chromatography (on silica, acetonitrile/$H_2O$ (0.05% TFA)) provided (R)-4-bromo-N-[4-[[[2-(hydroxyamino)-1-methyl-2-oxoethyl][2-(4-morpholinyl)ethyl]amino]sulfonyl]phenyl]benzamide, mono(trifluoroacetate) salt as a white solid (350 mg, 18%). MS(EI) $M^+$ calculated for $C_{22}H_{27}N_4O_6SBr$: 555, found: 555.

EXAMPLE 6

(R)-N-[4-[[[2-(Hydroxyamino)-1-methyl-2-oxoethyl][2-(4-morpholinyl)ethyl]amino]sulfonyl]phenyl]cyclohexanecarboxamide, Mono(trifluoroacetate) (Salt)

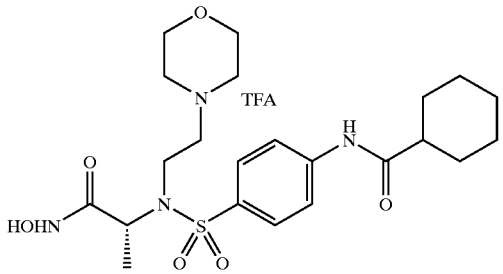

Part A: To a solution of D-alanine, t-butyl ester hydrochloride (9.80 g, 53.9 mmol) in $H_2O$ (64 mL) and acetone (26 mL) was added triethylamine (17.3 mL, 124 mmol) and the solution was cooled to zero degrees Celsius. To this solution was added 4-nitrobenzene-sulfonyl chloride (11.1 g, 50.2 mmol) dropwise in acetone (25 mL). The solution was stirred for 72 hours. The solution was concentrated in vacuo and the residue was dissolved into ethyl acetate. The solution was washed with 5% $KHSO_4$, saturated $NaHCO_3$ and saturated NaCl and dried over $Na_2SO_4$. Recrystallization (ethyl acetate/hexane) provided the sulfonamide as a solid (10.87 g, 66%).

Part B: To a solution of the sulfonamide of part A (10.8 g, 32.7 mmol) in DMF (60 mL) was added 4-(2-chloroethyl)morpholine (12.2 g, 65.4 mmol) and $K_2CO_3$ (13.6 g, 98.0 mmol) and the solution was heated to seventy degrees Celsius for 7 hours. The solution was partitioned between ethyl acetate and $H_2O$. The organic layer was washed with $H_2O$, saturated NaCl, and dried over $Na_2SO_4$. Concentration in vacuo followed by tritration (ethyl ether) provided the morpholine compound as a solid (8.48 g, 59%). MS(CI) $MH^+$ calculated for $C_{19}H_{29}N_3O_7S$: 444, found: 444.

Part C: To a solution of the morpholine compound of part B (8.49 g, 19.1 mmol) in THF (100 mL) under atmosphere of 50 psi of hydrogen was added 4% Pd/C and the solution was stirred for 2 hours until uptake stopped. The solution was filtered through Celite and concentration in vacuo of the filtrate provided the aniline as a solid (8.5 g, quantitative yield). MS(CI) MH$^+$ calculated for $C_{19}H_{31}N_3O_5S$: 414, found: 414.

Part D: To a solution of the aniline of part C (2.70 g, 6.53 mmol) in THF (40 mL) was added triethylamine (3.6 mL, 26.1 mmol) and the solution was cooled to zero degrees Celsius. To this solution was added cyclohexane carbonyl chloride (2.3 mL, 17.0 mmoL) and the solution was stirred for 30 minutes. The solution was concentrated in vacuo and the residue was partitioned between ethyl acetate and saturated $NaHCO_3$. The organic layer was washed with saturated $NaHCO_3$ and saturated NaCl, and dried over $Na_2SO_4$. Chromatography (on silica, ethyl acetate/methanol) provided the benzamide as a solid (2.09 g, 61%). MS(CI) MH$^+$ calculated for $C_{26}H_{41}N_3O_6S$: 524, found: 524.

Part E: To a solution of the benzamide of part D (2.0 g, 3.82 mmol) in anisole (10 mL) was added trifluoroacetic acid (18 mL). The solution was stirred for 18 hours at ambient temperature. The solution was concentrated in vacuo to remove the trifluoroacetic acid. The remaining solution was diluted with ethyl ester and the resulting white solid was collected by vacuum filtration to provide the acid (2.48 g, quantitative yield). MS(CI) MH$^+$ calculated for $C_{22}H_{33}N_3O_6S$: 468, found: 468.

Part F: To a solution of the acid of part E (1.27 g, 2.18 mmol) in DMF (10 mL) was added N-hydroxybenzotriazole (353 mg, 2.62 mmol) followed by 4-methylmorpholine (1.4 mL, 13.1 mmol), tetrahydropyranyl hydroxylamine (791 mg, 6.76 mmol) and 1-(3-dimethylaminopropyl)-3-ethylcarbodiimide hydrochloride (590 mg, 3.05 mmol). The solution was stirred for 72 hours. The solution was partitioned between ethyl acetate and saturated $NaHCO_3$ and the organic was washed with $H_2O$ and saturated NaCl and dried over $Na_2SO_4$. Chromatography (on silica, ethyl acetate/methanol) provided the ester as a white solid (1.2 g, quantitative yield). MS(CI) MH$^+$ calculated for $C_{27}H_{42}N_4O_7S$: 567, found 567.

Part G: A solution of the ester of part F (1.2 g, 2.12 mmol) in 4N HCl in dioxane (25 mL) was stirred for 1 hour. The solution was diluted with ethyl ether and resulting white solid was collected by vacuum filtration. The solid was suspended into ethyl acetate and was washed with saturated $NaHCO_3$ and saturated NaCl and dried over $Na_2SO_4$. Reverse phase chromatography (on silica, acetonitrile/$H_2O$ (0.05% TFA)) provided (R)-N-[4-[[[2-(hydroxyamino)-1-methyl-2-oxoethyl][2-(4-morpholinyl)ethyl]amino]sulfonyl]-phenyl]cyclohexane-carboxamide, mono (trifluoroacetate) salt as a white solid (312 mg, 25%). MS(CI) MH$^+$ calculated for $C_{22}H_{34}N_4O_6S$: 483, found 483.

EXAMPLE 7

(R)-N-4-[[[1-[(Hydroxyamino)carbonyl]-2-methylpropyl][2-(4-morpholinyl)ethyl]amino]sulfonyl]-phenyl]-4-propylbenzamide, Monohydrochloride

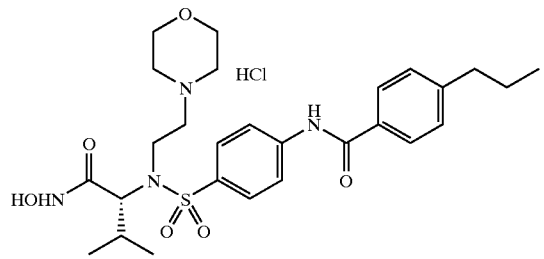

Part A: To a solution to D-valine (25.0 g, 213 mmol) in $H_2O$ (180 mL) and acetone (96 mL) was added triethylamine (62 mL, 448 mmol) and was cooled to zero degrees Celsius. To this solution was added 4-nitrobenzenesulfonyl chloride (45.3 g, 204 mmol) in acetone (100 mL) dropwise. The solution was stirred for 72 hours. The solution was concentrated in vacuo and the resulting aqueous layer was extracted with toluene and acidified to pH=2 with 2N HCl. The aqueous layer was extracted with ethyl acetate three times and the combined organic layers were washed with saturated NaCl and dried over $MgSO_4$. Concentration in vacuo provided the sulfonamide as a light brown solid (37.15 g, 61%).

Part B: A solution of the sulfonamide of part A (37.15 g, 123 mmol) and a catalytic amount of $H_2SO_4$ in dichloromethane/dioxane (1 L) was subjected to isobutylene for 18 hours. The solution was cooled to zero degrees Celsius and quenched with saturated $NaHCO_3$. The aqueous layer was extracted with ethyl acetate and the organic layer was washed with saturated NaCl and dried over $MgSO_4$. Chromatography (on silica, ethyl acetate/hexane) provided the t-butyl ester as a solid (16.7 g, 38%).

Part C: To a solution of the t-butyl ester of part B (16.5 g, 46 mmol) in DMF (60 mL) was added 4-(2-chloroethyl) morpholine hydrochloride (17.2 g, 92 mmol) and $K_2CO_3$ (25.5 g, 184 mmol) and the solution was heated to sixty degrees Celsius for 7 hours. The solution was partitioned between ethyl acetate and $H_2O$ and the organic layer was washed with saturated NaCl and dried over $Na_2SO_4$. Chromagraphy (on silica, ethyl acetate/hexane) provided the morpholine compound as a solid (21.5 g, 99%).

Part D: To a solution of the morpholine compound of part C (21.5 g, 45.6 mmol) in THF (200 mL) in a flask purged with $H_2$ was added 4% Pd/C (3.04 g) and the solution was hydrogenated until uptake ceased. The solution was filtered through Celite® to remove the excess catalyst and the filtrate was concentrated in vacuo to provide the aniline as an oil (19.2 g, 95%).

Part E: To a solution of the aniline of part D (2.9 g, 6.6 mmol) in THF (20 mL) was added triethylamine (3.66 mL, 26.3 mmol) and cooled to four degrees Celsius. To this solution was added 4-propylbenzoyl chloride (2.0 g, 11.0 mmol) and the solution was stirred for 1 hour at ambient temperature. The solution was concentrated in vacuo and the residue was partitioned between ethyl acetate and saturated $NaHCO_3$. The organic layer was washed with saturated NaCl and dried over $Na_2SO_4$. Chromatography (on silica, ethyl acetate/hexane) provided the benzamide as a solid (3.3 g, 85%).

Part F: To a solution of the benzamide of part E (3.2 g, 5.4 mmol) in dichloromethane (20 mL) was added trifluoroacetic acid (80 mL) and the solution was stirred for 30 minutes. The solution was concentrated in vacuo and the residue was dissolved into warm toluene/ethyl acetate and was added dropwise to ethyl ether to produce a yellow precipitate. Vacuum filtration provided the acid as a yellow solid (2.58 g, 84%).

Part G: To a solution of the acid of part F (2.04 g, 3.6 mmol) in DMF (5 mL) was added N-hydroxybenzotriazole (583 mg, 4.32 mmol), 4-methylmorpholine (2.37 mL, 21.6 mmol), tetrahydropyranyl hydroxylamine (1.31 g, 11.2 mmol) and 1-(3-dimethylaminopropyl)-3-ethylcarbodiimide hydrochloride (966 mg, 5.04 mmol). The solution was stirred for 18 hours at ambient temperature. The solution was partitioned between ethyl acetate and saturated NaHCO$_3$. The organic layer was washed with saturated NaHCO$_3$, H$_2$O and saturated NaCl and dried over Na$_2$SO$_4$. Chromatography (on silica, ethyl acetate/methanol) provided the ester as a solid (2.15 g, 95%).

Part H: Into a solution of the ester of part G (2.15 g, 3.4 mmol) in methanol (30 mL) was bubbled HCl gas. After 1 hour the solution was concentrated in vacuo to a reduced volume (5 mL) and this solution was dropped into cooled ethyl ether to produce a precipitate. Vacuum filtration provided (R)-N-4-[[[1-[(hydroxyamino)carbonyl]-2-methylpropyl][2-(4-morpholinyl)ethyl]amino]sulfonyl]-phenyl]-4-propylbenzamide, monohydrochloride as a white solid (1.64 g, 83%). MS(CI) MH$^+$ calculated for C$_{27}$H$_{38}$N$_4$O$_6$S: 547, found 547.

EXAMPLE 8

(R)-4-Butyl-N-[4-[[[1-[(hydroxyamino)-carbonyl]-2-methylpropyl][2-(4-morpholinyl)-ethyl]amino] sulfonyl]phenyl]benzamide, Monohydrochloride

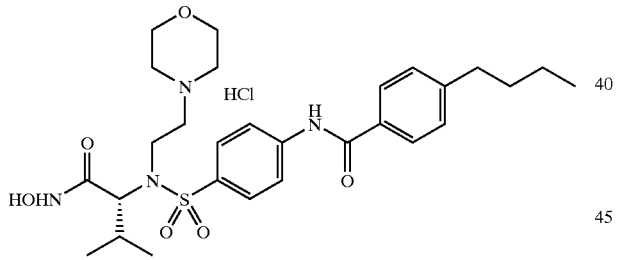

Part A: To a solution of the aniline of Example 7, part D (2.53 g, 5.73 mmol) in THF (20 mL) was added triethylamine (3.2 mL, 22.9 mmol) and the solution was cooled to four degrees Celsius. To this solution was added 4-butylbenzoyl chloride (1.9 g, 9.7 mmol) and the solution was stirred at ambient temperature for 18 hours. The solution was concentrated in vacuo and the residue was partitioned between ethyl acetate and saturated NaHCO$_3$. The organic layer was washed with saturated NaHCO$_3$ and saturated NaCl and dried over Na$_3$SO$_4$. Chromatography (on silica, ethyl acetate/hexane) provided the benzamide as a solid (2.8 g, 82%)

Part B: A solution of the benzamide of part A (2.8 g, 4.6 mmol) in 4N HCl in dioxane (20 mL) was stirred for 72 hours at ambient temperature. The solution was concentrated in vacuo and the residue was dissolved in dioxane (3 mL) and dropped into stirring ethyl ether. The resulting precipitate was collected by vacuum filtration to provide the acid as a white solid (2.7 g, quantitative yield).

Part C: To a solution of the acid of part B (2.0 g, 3.4 mmol) in DMF (5 mL) was added N-hydroxybenzotriazole (557 mg, 4.13 mmol) and the solution was cooled to four degrees Celsius. To this solution was added 4-methylmorpholine (2.27 mL, 20.6 mmol), 1-(3-dimethylaminopropyl)-3-ethylcarbodiimide hydrochloride (923 mg, 4.81 mmol) and tetrahydropyranyl hydroxylamine (604 mg, 5.16 mmol) and the solution was stirred for 1 hour. The solution was partitioned between ethyl acetate and saturated NaHCO$_3$. The organic layer was washed with saturated NaHCO$_3$, H$_2$O and saturated NaCl, and dried over Na$_2$SO$_4$. Chromatography (on silica, ethyl acetate/methanol) provided the ester as a solid (2.0 g, 91%).

Part D: To a solution of the ester of part C (2.0 g, 3.1 mmol) in methanol (1.5 mL) was added 4N HCl in dioxane (10 mL) and the solution was stirred for 18 hours. The solution was concentrated in vacuo to a smaller volume and dropped into ethyl ether. The resulting precipitate was collected by vacuum filtration to provide (R)-4-butyl—N-[4-[[[1-[(hydroxyamino)-carbonyl]-2-methylpropyl][2-(4-morpholinyl)-ethyl]amino]sulfonyl]phenyl]benzamide, monohydrochloride as a white solid (1.8 g, 96%). MS(CI) MH$^+$ calculated for C$_{28}$H$_{40}$N$_4$O$_6$S: 561, found: 561.

EXAMPLE 9

R-N-[4-[[[1-(Hydroxyamino)carbonyl]-2-methylpropyl][2-(4-morpholinyl)ethyl]amino]-sulfonyl]phenyl]-4-pentylbenzamide, Monohydrochloride

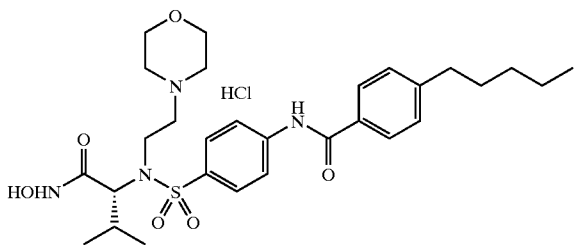

Part A: To a solution of the aniline of Example 7, part D (2.60 g, 5.88 mmol) in THF (20 mL) was added triethylamine (3.2 mL, 22.8 mmol) and the solution was cooled to four degrees Celsius. To this solution was added 4-pentylbenzoyl chloride (2.1 g, 10.0 mmol) and the solution was stirred for 18 hours at ambient temperature. The solution was concentrated in vacuo and the residue was partitioned between ethyl acetate and saturated NaHCO$_3$. The organic layer was washed with saturated NaHCO$_3$ and saturated NaCl and dried over Na$_2$SO$_4$. Chromatography (ethyl acetate/hexane) provided the benzamide as a solid (2.09 g, 58%).

Part B: A solution of the benzamide of part A (2.09 g, 3.4 mmol) in 4N HCl (20 mL) was stirred for 72 hours. The solution was concentrated in vacuo and the residue was dissolved into ethyl acetate (5 mL) and dropped into ethyl ether. The resulting precipitate was collected by vacuum filtration to provide the acid as a solid (1.9 g, 94%).

Part C: To a solution of the acid of part B (1.52 g, 2.56 mmol) in DMF (5 mL) was added N-hydroxybenzotriazole (414 mg, 3.07 mmol) and the solution was cooled to four degrees Celsius. To this solution was added 4-methylmorpholine (1.69 mL, 15.6 mmol), 1-(3-dimethylaminopropyl)-3-ethylcarbodiimide hydrochloride (687 mg, 3.58 mmol) and tetrahydropyranyl hydroxylamine (449 mg, 3.84 mmol) and was stirred for 1 hour at ambient temperature. The solution was partitioned between ethyl acetate and saturated NaHCO$_3$ and the organic layer was washed with saturated NaHCO$_3$, saturated NaCl and H$_2$O and dried over Na$_2$SO$_4$. Chromatography (ethyl acetate/ methanol) provided the ester as a solid (1.54 g, 91%).

Part D: To a solution of the ester of part C (1.54 g, 2.34 mmol) in methanol (1 mL) was added 4N HCl (10 mL) and the solution was stirred for 18 hours at ambient temperature. The solution was concentrated in vacuo. Reverse phase chromatography (on silica, acetonitrile/H$_2$O (HCl) provided the title compound, R-N-[4-[[[1-(hydroxyamino)carbonyl]-2-methylpropyl][2-(4-morpholinyl)ethyl]amino]sulfonyl] phenyl]-4-pentylbenzamide, monohydrochloride as a white solid (745 mg, 52%). MS(CI) MH$^+$ calculated for C$_{29}$H$_{42}$N$_4$O$_6$S: 575, found: 575.

EXAMPLE 10

(R)-4-Hexyl-N-[4-[[[1-(hydroxyamino)-carbonyl]-2-methylpropyl][2-(4-morpholinyl)ethyl]amino] sulfonyl]phenylbenzamide, Monohydrochloride

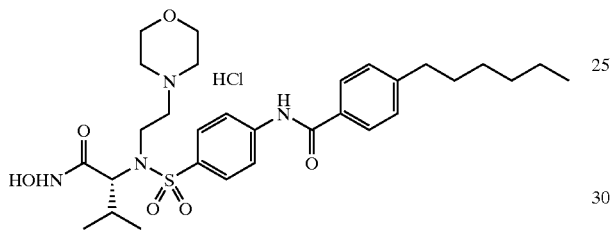

Part A: To a solution of the aniline of Example 7, part D (2.5 g, 5.7 mmol) was added triethylamine (3.2 mL, 22.8 mmol) and the solution was cooled to four degrees Celsius. To this solution was added 4-hexylbenzoyl chloride (2.18 g, 9.69 mmol) and the solution was stirred overnight at ambient temperature. The solution was concentrated in vacuo and the residue was partitioned between ethyl acetate .and saturated NaHCO$_3$. The organic layer was washed with saturated NaHCO$_3$ and saturated NaCl and dried over Na$_2$SO$_4$. Chromatography (on silica, ethyl acetate/hexane) provided the benzamide as a solid (2.76 g, 77%).

Part B: A solution of the benzamide of part A (2.7 g, 4.3 mmol) in 4N HCl in dioxane (20 mL) was stirred for 72 hours. The solution was concentrated in vacuo and the residue was dissolved into ethyl acetate (5 mL). This solution was dropped into ethyl ether. The resulting precipitate was collected by vacuum filtration to provide the acid as a solid (2.5 g, 95%).

Part C: To a solution of the acid of part B (2.03 g, 3.33 mmol) in DMF (5 mL) was added N-hydroxybenzotriazole (540 mg, 4.00 mmol) and the solution was cooled to four degrees Celsius. To this solution was added 4-methylmorpholine (2.19 mL, 20.0 mmol), 1-(3-dimethylaminopropyl)-3-ethylcarbodiimide hydrochloride (894 mg, 4.66 mmol) and tetrahydropyranyl hydroxylamine (615 mg, 5.00 mmol) and the solution was stirred for 1 hour at ambient temperature. The solution was partitioned between ethyl acetate and saturated NaHCO$_3$ and the organic layer was washed with saturated NaHCO$_3$, saturated NaCl and H$_2$O and dried over Na2SO$_4$. Chromatography (on silica, ethyl acetate/methanol) provided the ester as a solid (2.01 g, 90%).

Part D: To a solution of the ester of part C (2.01 g, 3.24 mmol) in methanol (1 mL) was added 4N HCl (10 mL) and the solution was stirred for 18 hours at ambient temperature. Reverse phase chromatography (on silica, acetonitrile/H$_2$O (0.05% HCl)) provided the title compound, (R)-4-hexyl-N-[4-[[[1-(hydroxyamino)carbonyl]-2-methylpropyl][2-(4-morpholinyl)ethyl]amino]sulfonyl]-phenylbenzamide, monohydrochloride, as a white solid (1.23 g, 61%). MS(CI) MH$^+$ calculated for C$_{30}$H$_{44}$N$_4$O$_6$S: 589, found: 589.

EXAMPLE 10a (R)-4-Hexyl-N-[4-[[[1-(hydroxyamino)-carbonyl]-2-methylpropyl][2-(4-morpholinyl)ethyl]amino] sulfonyl]phenylbenzamide To a solution of the methyl ester of Example 10, part C (1.4 mmol) in methanol (1.6 mL) and THF (1.6 mL) is added 50% aqueous hydroxylamine (1.6 mL). The solution is stirred for 18 hours. The solution is concentrated in vacuo and the residue was partitioned between ethyl acetate and H$_2$O. The organic layer is washed with saturated NaCl and dried over Na$_2$SO$_4$. Concentrationof the dried organic layer in vacuo provides "10-Hydrochloride. MS(CI) MH$^+$ calculated for C$_{30}$H$_{44}$N$_4$O$_6$S: 589.

EXAMPLE 11

(R)-N-[4-[[[1-[(Hydroxyamino)carbonyl]-2-methylpropyl](3-pyridinylmethyl)amino]sulfonyl] phenyl]-4-propylbenzamide

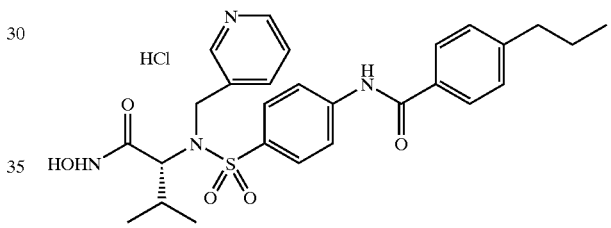

Part A: To a solution of aniline (3.3 g, 35.7 mmol) and triethylamine (8.0 g, 79 mmol) in THF, cooled to zero degrees Celsius, was added benzoyl chloride (5.0 g, 27 mmol) and the solution was stirred for 18 hours at ambient temperature. The solution was diluted with H$_2$O and extracted with ethyl acetate. The organic layer was washed with 1N HCl and saturated NaHCO$_3$ and dried over MgSO$_4$. Recrystallization (ethyl acetate/hexane) provided the benzamide as an off-white solid (4.91 g, 64%).

Part B: To chlorosulfonic acid (2.0 g, 17.3 mmol) cooled to five degrees Celsius was added the benzamide of part A (4.91 mg, 17.3 mmol). The solution was heated to sixty-five degrees Celsius for 1 hour. The solution was cooled to ambient temperature and diluted with dichloromethane. The solution was poured into cold H$_2$O and extracted with ethyl acetate. The organic layer was washed with saturated NaHCO$_3$ and dried over MgSO$_4$. Concentration in vacuo provided the sulfonyl chloride as a yellow solid (4.89 g, 74%).

Part C: To a solution of D-valine, t-butyl ester (2.6 g, 15.1 mmol) in THF (25 mL) was added the sulfonyl chloride of part B (4.8 g, 12.5 mmol) followed by triethylamine (6.3 mL, 44.5 mmol) and the solution was stirred for 18 hours at ambient temperature. The solution was diluted with H$_2$O and the resulting precipitate was collected by vacuum filtration. The solid was dissolved into ethyl acetate and dichloromethane and dried over Na$_2$SO$_4$. Concentration in vacuo provided the sulfonamide (4.0 g, 67%).

Part D: To a solution the sulfonamide of part C (2.0 g, 4.1 mmol) in DMF (10 mL) was added K$_2$CO$_3$ (2.2 g, 16 mmol) followed by picolyl chloride hydrochloride (860 mg, 5.0 mmol) and the solution was stirred for 40 hours at ambient temperature. The solution was partitioned between ethyl acetate and H$_2$O. The organic layer was chromatographed (on silica, ethyl acetate/hexane) to provide the picolyl compound (1.3 g, 57%).

Part E: To a solution of the picolyl compound of part D (1.1 g, 2 mmol) in dichloromethane (15 mL) was added trifluoroacetic acid (20 mL) and the solution was stirred for 20 minutes. Concentration in vacuo provided the acid as a solid (1.24 mg, quantitative yield).

Part F: To a solution of the acid of part E (1.2 g, 2.0 mmol) in DMF (20 mL) was added 4-methylmorpholine (1.2 g, 12 mmol), N-hydroxybenzotriazole (800 mg, 3 mmol) and 1-(3-dimethylaminopropyl)-3-ethylcarbodiimide hydrochloride (780 mg, 4 mmol). After 10 minutes of stirring, tetrahydropyranyl hydroxylamine (720 mg, 6 mmol) was added and the solution was stirred for 18 hours. The solution was concentrated in vacuo and the residue was partitioned between ethyl acetate and $_2$O. The organic layer was dried over MgSO$_4$. Chromatography (on silica, ethyl acetate/hexane/methanol) provided the ester as an oil (1.4 g, quantitative yield).

Part G: A solution of the ester of part F (1.4 g, 2 mmol) in dioxane (5 mL) and 4M HCl in dioxane (10 mL) was stirred for 30 minutes. Dilution with ethyl ether which precipitated a white solid followed by collection by vacuum filtration provided the title compound, (R)-N-[4-[[[1-[(hydroxyamino)carbonyl]-2-methylpropyl](3-pyridinylmethyl)amino]sulfonyl]phenyl]-4-propylbenzamide (1.28 g, 2.3 mmol). MS(CI) MH$^+$ calculated for C$_{27}$H$_{32}$N$_4$O$_5$S: 525, found: 525.

EXAMPLE 12

(R)-N-[4-[[[1-(Hydroxyamino)carbonyl]-2-methylpropyl][2-(4-morpholinyl)ethyl]-amino]sulfonyl]phenyl]benzamide, Monohydrochloride

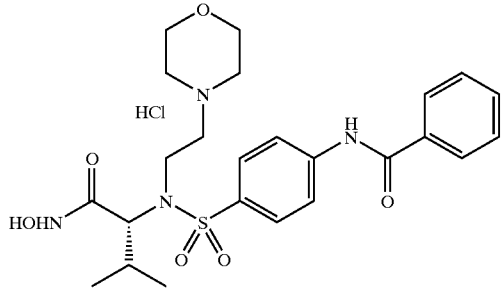

Part A: To a solution of the aniline of Example 7, part D (2.2 g, 5.0 mmol) in dichloromethane (5 mL) was added triethylamine (1.0 g, 10 mmol) and the solution was cooled to zero degrees Celsius. To this solution was added benzoyl chloride (717 mg, 5.1 mmol) in dichloromethane (5 mL). The solution was stirred for 16 hours at ambient temperature. The solution was diluted with dichloromethane and washed with saturated NaHCO$_3$ and saturated NaCl and dried over Na$_2$SO$_4$. Chromatography (on silica, ethyl acetate/hexane) provided the benzamide as a solid (2.7 g, 99%).

Part B: To a solution of the benzamide of part A (2.56 g, 4.69 mmol) in dichloromethane (50 mL) was added trifluoroacetic acid (12 mL) and the solution was stirred for 18 hours at ambient temperature. The solution was concentrated in vacuo. Chromatography (on silica, ethyl acetate/methanol) provided the acid as a solid (1.64 g, 71%).

Part C: To a solution of the acid of part C (1.24 g, 2.53 mmol) in DMF (15 mL) was added N-hydroxybenzotriazole (513 mg, 3.8 mmol) and 4-methylmorpholine (1.5 g, 15.2 mmol) and the solution was cooled to zero degrees Celsius. To this solution was added 1-(3-dimethylaminopropyl)-3-ethylcarbodiimide hydrochloride (534 mg, 2.78 mmol) and tetrahydropyranyl hydroxylamine (444 mg, 3.8 mmol) and the solution was stirred for 18 hours at ambient temperature. The solution was diluted with H$_2$O and the solution was extracted with ethyl acetate. The organic layer was washed with saturated NaHCO$_3$ and saturated NaCl and dried over Na$_2$SO$_4$. Chromatography (on silica, ethyl acetate/hexane/methanol) provided the ester as a solid (815 mg, 55%).

Part D: To a solution of the ester of part C (750 mg, 1.27 mmol) in dioxane (5 mL) was added 4N HCl in dioxane (10 mL) and the solution was stirred for 20 minutes at ambient temperature. Trituration (hexane) provided the title compound, (R)-N-[4-[[[1-(hydroxyamino)carbonyl]-2-methylpropyl][2-(4-morpholinyl)ethyl]-amino]sulfonyl]phenyl]benzamide, monohydrochloride, as a white solid (590 mg, 86%). MS(CI) MH$^+$ calculated for C$_{24}$H$_{32}$N$_4$O$_6$S: 505, found: 505.

EXAMPLE 13

(R)-4-Bromo-N-[4-[[[1-(hydroxyamino)carbonyl]-2-methylpropyl][2-(4-morpholinyl)ethyl]amino]sulfonyl]phenylbenzamide, Monohydrochloride

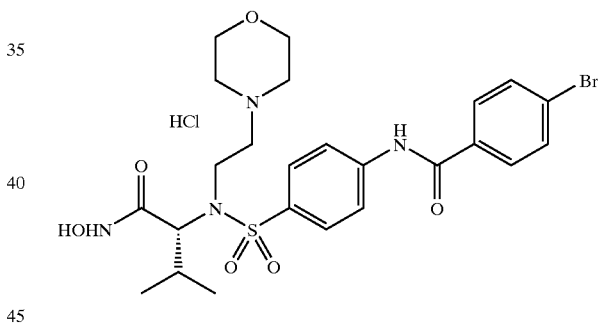

Part A: To a solution of the aniline of Example 7, part D (2.2 g, 5 mmol) in dichloromethane (50 mL) was added triethylamine (1.5 g, 15 mmol) and 4-bromobenzoyl chloride (1.65 g, 7.5 mmol) and the solution was stirred for 12 hours at ambient temperature. The solution was diluted with dichloromethane and washed with saturated NaHCO$_3$ and saturated NaCl and dried over Na$_2$SO$_4$. Chromatography (on silica, ethyl acetate/hexane) provided the benzamide as a solid (2.8 g, 90%).

Part B: To a solution of the benzamide of part A (2.5 g, 4.0 mmol) in dichloromethane (4 mL) was added trifluoroacetic acid (16 mL) and the solution was stirred for 16 hours at ambient temperature. The solution was concentrated in vacuo and chromatography (on silica, ethyl acetate/methanol) provided the acid as a solid (1.68 g, 74%).

Part C: To a solution of the acid of part B (1.2 g, 2.11 mmol) in DMF (20 mL) was added N-hydroxybenzotriazole (428 mg, 3.16 mmol) and 4-methylmorpholine (1.3 g, 12.7 mmol) and the solution was cooled to zero degrees Celsius. To this solution was added 1-(3-dimethylaminopropyl)-3-ethylcarbodiimide hydrochloride (445 mg, 2.32 mmol) and tetrahydropyranyl hydroxylamine (371 mg, 3.16 mmol) and the solution was stirred for 18 hours at ambient temperature. The solution was diluted with $H_2O$ and the solution was extracted with ethyl acetate. The organic layer was washed with saturated $NaHCO_3$ and saturated NaCl and dried over $Na_2SO_4$. Chromatography (on silica, ethyl acetate/hexane/methanol) provided the ester as a solid (940 mg, 67%).

Part D: To a solution of the ester of part C (800 mg, 1.2 mmol) in dioxane (5 mL) was added 4N HCl in dioxane (10 mL) and the solution was stirred for 20 minutes at ambient temperature. Trituration (hexane) provided the title compound, (R)-4-bromo—N-[4-[[[1-(hydroxyamino)carbonyl]-2-methylpropyl][2-(4-morpholinyl)ethyl]amino]sulfonyl]phenylbenzamide, monohydrochloride, as a white solid (668 mg, 90%). MS(CI) $MH^+$ calculated for $C_{24}H_{31}N_4O_6SBr$: 584, found: 584.

EXAMPLE 14

(R)-N-Hydroxy-α-[[[4-(4-pentylbenzoyl)amino]phenyl]sulfonyl]amino Benzenepropanamide

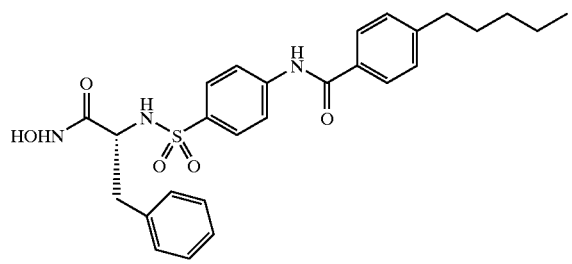

Part A: To a solution of aniline (3.3 9, 35.7 mmol) and triethylamine (8.0 g, 79 mmol) in THF, cooled to zero degrees Celsius, was added 4-pentylbenzoyl chloride (5.7 g, 27 mmol) and the solution was stirred for 18 hours at ambient temperature. The solution was diluted with $H_2O$ and extracted with ethyl acetate. The organic layer was washed with 1N HCl and saturated $NaHCO_3$ and dried over $MgSO_4$. Recrystallization (ethyl acetate/hexane) provided the benzamide as an off-white solid.

Part B: To chlorosulfonic acid (2.3 g, 20 mmol) cooled to five degrees Celsius was added the benzamide of part A. The solution was heated to sixty-five degrees Celsius for 1 hour. The solution was cooled to ambient temperature and diluted with dichloromethane. The solution was poured into cold $H_2O$ and extracted with ethyl acetate. The organic layer was washed with saturated $NaHCO_3$ and dried over $MgSO_4$. Concentration in vacuo provided the sulfonyl chloride as a yellow solid (5.5 g, 55%, two steps).

Part C: To a solution of R-phenylalanine (2.47 g, 15 mmol) in THF (100 mL) and $H_2O$ (30 mL) cooled to zero degrees Celsius was added triethylamine (4.54 g, 45 mmol) and the sulfonyl chloride of part B (5.5 g, 15 mmol) and the solution was stirred for 16 hours at ambient temperature. The solution was concentrated in vacuo and extracted with ethyl acetate. The organic layer was washed with saturated NaCl. Chromatography (on silica, ethyl acetate/hexane) provided the sulfonamide as a solid (4.5 g, 61%).

Part D: To a solution of the sulfonamide of part C (494 mg, 1.0 mmol) in DMF (20 mL) was added N-hydroxybenzotriazole (203 mg, 1.5 mmol) and the solution was cooled to ten degrees Celsius. To this solution was added 1-(3-dimethylaminopropyl)-3-ethylcarbodiimide hydrochloride (211 mg, 1.1 mmol) and tetrahydropyranyl hydroxylamine (351 mg, 3.0 mmol) and the solution was stirred for 12 hours at ambient temperature. The solution was diluted with $H_2O$ and the resulting precipitate was extracted with ethyl acetate and washed with saturated NaCl and dried over $Na_2SO_4$. Chromatography (ethyl acetate/hexane) provided the ester as a solid (327 mg, 57%).

Part E: To a solution of the ester of part D (200 mg, 0.34 mmol) in dioxane (3 mL) was added 4N HCl in dioxane (5 mL) and the solution was stirred for 1 hour at ambient temperature. The solution was concentrated in vacuo and reverse phase chromatography (acetonitrile/$H_2O$) provided the title compound, (R)-N-hydroxy-α-[[[4-(4-pentylbenzoyl)amino]phenyl]sulfonyl]amino benzenepropanamide, as a white solid (80 mg, 26%). MS(CI) $MH^+$ calculated for $C_{27}H_{31}N_3O_5S$: 510, found: 510.

EXAMPLE 15

(R)-N-Hydroxy-α-[[2-(4-morpholinyl)ethyl]-[[4-[(4-pentylbenzoyl)amino]phenyl]sulfonyl]amino] benzenepropanamide, Monohydrochloride

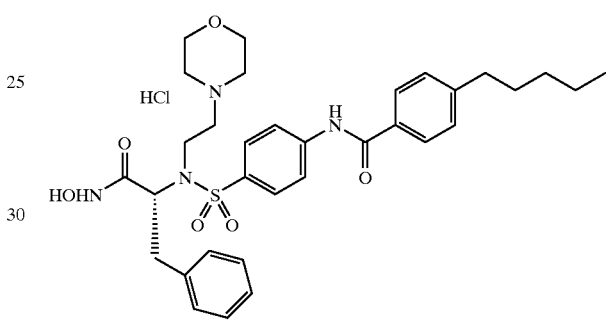

Part A: To a solution of the sulfonamide of Example 14, part C (7.0 g, 15 mmol) in toluene (120 mL) was added DMF di-tert-butylacetal (6.1 g, 30 mmol) and the solution was heated at one hundred degrees Celsius for 1 hour. Concentration in vacuo followed by recrystallization (cold methanol) provided the ester as a solid (3.7 g, 45%).

Part B: To a solution of the ester of part A (3.5 g, 6.35 mmol) and $K_2CO_3$ (5.53 g, 40 mmol) in DMF (100 mL) was added 4-(2-chloroethyl)morpholine hydrochloride (1.77 g, 9.52 mmol) and the solution was stirred for 16 hours at sixty degrees Celsius. The solution was partitioned between ethyl acetate and $H_2O$ and the organic layer was washed with saturated NaCl and dried over $Na_2SO_4$. Chromatography (ethyl acetate/hexane) provided the morpholine compound as a solid (1.8 g, 43%).

Part C: To a solution of the morpholine compound of part B (1.4 g, 2.1 mmol) in dichloromethane (5 mL) was added trifluoroacetic acid (12 mL) and the solution was stirred for 16 hours at ambient temperature. Concentration in vacuo followed by reverse phase chromatography (acetonitrile/$H_2O$) provided the acid as a solid (1.12 g, 87%).

Part D: To a solution of the acid of part C (607 mg, 1.0 mmol) in DMF (40 mL) was added N-hydroxybenzotriazole (207 mg, 1.5 mmol) and the solution was cooled to two degrees Celsius. To this solution was added 1-(3-dimethylaminopropyl)-3-ethylcarbodiimide hydrochloride (211 mg, 1.1 mmol) and tetrahydropyranyl hydroxylamine (585 mg, 5.0 mmol) and the solution was stirred for 6 hours at ambient temperature. The solution was diluted with $H_2O$ and the resulting precipitate was extracted with ethyl acetate and washed with saturated NaCl and dried over $Na_2SO_4$.

Chromatography (on silica, ethyl acetate/hexane) provided the ester as a solid.

Part E: To a solution of the ester of part D in dioxane (3 mL) was added 4N HCl in dioxane (5 mL) and the solution was stirred for 1 hour at ambient temperature. The solution was concentrated in vacuo and reverse phase chromatography (acetonitrile/$H_2O$) provided the title compound, (R)—N-hydroxy-α-[[2-(4-morpholinyl)ethyl]-[[4-[(4-pentylbenzoyl)amino]phenyl]-sulfonyl]amino]benzenepropanamide, monohydrochloride, as a white solid (80 mg, 12%, two steps). MS(CI) $MH^+$ calculated for $C_{33}H_{42}N_4O_6S$: 660, found: 660.

EXAMPLE 16

In Vitro Metalloprotease Inhibition

The compounds prepared in the manner described in Examples 1 to 15 were assayed for activity by an in vitro assay. Following the procedures of Knight et al., FEBS Lett. 296(3):263 (1992). Briefly, 4-aminophenylmercuric acetate (APMA) or trypsin activated MMPs were incubated with various concentrations of the inhibitor compound at room temperature for 5 minutes.

More specifically, recombinant human MMP-13 and MMP-1 enzymes were prepared in laboratories of the assignee. MMP-13 was expressed in baculovirus as a proenzyme, and purified first over a heparin agarose column and then over a chelating zinc chloride column. The proenzyme was activated by APMA for use in the assay. MMP-1 expressed in transfected HT-1080 cells was provided by Dr. Howard Welgus of Washington University, St. Louis, Mo. The enzyme was also activated using APMA and was then purified over a hydroxamic acid column.

The enzyme substrate is a methoxycoumarin-containing polypeptide having the following sequence:

MCA-ProLeuGlyLeuDpaAlaArg$NH_2$, wherein MCA is methoxycoumarin and Dpa is 3-(2,4-dinitrophenyl)-L-2,3-diaminopropionyl alanine. This substrate is commercially available from Baychem as product M-1895.

The buffer used for assays contained 100 mM Tris-HCl, 100 mM NaCl, 10 mM $CaCl_2$ and 0.05 percent polyethyleneglycol (23) lauryl ether at a pH value of 7.5. Assays were carried out at room temperature, and dimethyl sulfoxide (DMSO) at a final concentration of 1 percent was used to dissolve inhibitor compound.

The assayed inhibitor compound in DMSO/buffer solution was compared to an equal amount of DMSO/buffer with no inhibitor as control using Microfluor™ White Plates (Dynatech). The inhibitor or control solution was maintained in the plate for 10 minutes and the substrate was added to provide a final concentration of 4 μM.

In the absence of inhibitor activity, a fluorogenic peptide was cleaved at the gly-leu peptide bond, separating the highly fluorogenic peptide from a 2,4-dinitrophenyl quencher, resulting in an increase of fluorescence intensity (excitation at 328 nm/emission at 415 nm). Inhibition was measured as a reduction in fluorescent intensity as a function of inhibitor concentration, using a Perkin Elmer L550 plate reader. The $IC_{50}$ values were calculated from those values. The results are set forth in the Inhibition Table below as Table 9, reported in terms of $IC_{50}$.

TABLE 9

INHIBITION TABLE

| Example | hMMP-1 (nM) | hMMP-2 (nM) | hMMP-3 (nM) | hMMP-8 (nM) | hMMP-9 (nM) | hMMP-13 (nM) |
|---|---|---|---|---|---|---|
| 4 | >10,000 | | | | 20.0 | 2.5 |
| 4a | >10,000 | 0.2 | | | 24.0 | 2.2 |
| 5 | 4,850 | | | | | 0.35 |
| 6 | >10,000 | | | | 3,500 | 250 |
| 7 | 4,000 | 0.2 | 90.0 | 9.0 | 4.5 | 0.3 |
| 8 | 4,000 | 0.2 | 50.0 | 25.8 | 31.0 | 0.1 |
| 9 | 4,000 | <0.1 | 55.0 | 8.0 | 200 | <0.1 |
| 10 | 5,600 | | | | 350 | <0.1 |
| 10a | | <0.1 | 180 | 2.6 | | |
| 11 | >10,000 | 0.1 | 225 | 39.0 | 24.0 | 0.5 |
| 12 | 3,400 | | 800 | 12.3 | 245 | 11.4 |
| 13 | 880 | | | | 1.9 | 0.4 |
| 14 | >10,000 | <0.1 | 30.0 | 34.0 | 161 | <0.1 |
| 15 | >10,000 | <0.1 | 140 | 241 | 286 | <0.1 |

EXAMPLE 17

In Vivo Angiogenesis Assay

The study of angiogenesis depends on a reliable and reproducible model for the stimulation and inhibition of a neovascular response. The corneal micropocket assay provides such a model of angiogenesis in the cornea of a mouse. See, *A Model of Angiogenesis in the Mouse Cornea*; Kenyon, B M, et al., Investigative Ophthalmology & Visual Science, July 1996, Vol. 37, No. 8.

In this assay, uniformly sized Hydron™ pellets containing bFGF and sucralfate are prepared and surgically implanted into the stroma mouse cornea adjacent to the temporal limbus. The pellets are formed by making a suspension of 20 μL sterile saline containing 10 μg recombinant bFGF, 10 mg of sucralfate and 10 μL of 12 percent Hydron™ in ethanol. The slurry is then deposited on a 10×10 mm piece of sterile nylon mesh. After drying, the nylon fibers of the mesh are separated to release the pellets.

The corneal pocket is made by anesthetizing a 7 week old C57Bl/6 female mouse, then proptosing the eye with a jeweler's forceps. Using a dissecting microscope, a central, intrastromal linear keratotomy of approximately 0.6 mm in length is performed with a #15 surgical blade, parallel to the insertion of the lateral rectus muscle. Using a modified cataract knife, a lamellar micropocket is dissected toward the temporal limbus. The pocket is extended to within 1.0 mm of the temporal limbus. A single pellet is placed on the corneal surface at the base of the pocket with a jeweler's forceps. The pellet is then advanced to the temporal end of the pocket. Antibiotic ointment is then applied to the eye.

Mice are dosed on a daily basis for the duration of the assay. Dosing of the animals is based on bioavailability and overall potency of the compound. an exemplary dose is 50 mg/kg bid, po. Neovascularization of the corneal stroma begins at about day three and is permitted to continue under the influence of the assayed compound until day five. At day five, the degree of angiogenic inhibition is scored by viewing the neovascular progression with a slit lamp microscope.

The mice are anesthetized and the studied eye is once again proptosed. The maximum vessel length of neovascularization, extending from the limbal vascular plexus toward the pellet is measured. In addition, the contiguous circumferential zone of neovascularization is measured as clock hours, where 30 degrees of arc equals one clock hour. The area of angiogenesis is calculated as follows.

$$area = \frac{(0.4 \times clock\ hours \times 3.14 \times vessel\ length\ (in\ mm))}{2}$$

The studied mice are thereafter compared to control mice and the difference in the area of neovascularization is recorded. A contemplated compound typically exhibits about 25 to about 75 percent inhibition, whereas the vehicle control exhibits zero percent inhibition.

Without further elaboration, it is believed that one skilled in the art can, using the preceding description, utilize the present invention to its fullest extent. The foregoing specific embodiments are, therefore, to be construed as merely illustrative, and not limitative of the remainder of the disclosure in any way whatsoever.

From the forgoing description, one skilled in the art can easily ascertain the essential characteristics of this invention, and without departing from the spirit and scope thereof, can make various changes and modifications of the invention to adapt it to various usages and conditions.

What is claimed is:

1. A compound or a salt thereof, wherein:
    the compound or salt is characterizeable in that the compound or salt selectively inhibits in vitro activity of human MMP)-2, human MMP-3, and/or human MMP-13 over in vitro activity of human MMP-1;
    the compound corresponds in structure to Formula VII:

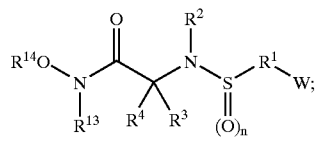

VII n is selected from the group consisting of zero, 1, and 2;
    W is —$NR^5COR^6$;
    $R^1$ is selected from the group consisting of cycloalkylene, arylene, and heteroarylene;
    $R^2$ is selected from the group consisting of alkyl, aralkyl, heteroaralkyl, cycloalkylalkyl, heterocycloalkylalkyl, hydroxycarbonylalkyl, aroylalkyl, and heteroaroylalkyl;

$R^3$ is selected from the group consisting of hydrido, alkyl, aryl, aralkyl, thioalkyl, heteroaralkyl, heteroaryl, alkoxyalkoxyalkyl, trifluoromethylalkyl, alkoxycarbonylalkyl, aralkoxycarbonylalkyl, hydroxycarbonylalkyl, alkoxyalkyl, heterocycloalkylalkyl, aryloxyalkyl, alkylthioalkyl, arylthioalkyl, heteroarylthioalkyl, a sulfoxide of any said thio-containing substituents, a sulfone of any said thio-containing substituents, —$(CH_2)_x$—$C(O)NR^{11}R^{12}$, and —$(CH_2)_y$—$W^1$;
each x is an integer from zero to 6;
y is an integer from I to 6;
$R^4$ is selected from the group consisting of hydrido and $C_1$–$C_4$ alkyl;
as to $R^5$ and $R^6$:
    $R^5$ is selected from the group consisting of hydrido and $C_1$–$C_4$ alkyl; and $R^6$ is selected from the group consisting of hydrido, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —$(CH_2)_x$—$NR^{11}R^{12}$, wherein:
        any aryl or heteroaryl of $R^6$ is optionally substituted with one or more substituents independently selected from the group consisting of halo, $C_1$–$C_6$ alkyl, $C_1$–$C_4$ alkoxy, nitro, cyano, hydroxy, carboxy, hydroxycarbonylalkyl, —$(CH_2)_x$—$NR^{11}R^{12}$, trifluoromethyl, alkoxycarbonyl, aminocarbonyl, thio, alkylsulfonyl, carbonylamino, aminosulfonyl, alkylsulfonamino, alkoxyalkyl, cycloalkyloxy, alkylthioalkyl, and alkylthio, or
    $R^5$ and $R^6$, together with the atoms to which they are bonded, form an optionally substituted 5- or 7-membered cyclic amide or imide;
as to each pair of $R^{11}$ and $R^{12}$:
    $R^{11}$ and $R^{12}$ are independently selected from the group consisting of hydrido, alkyl, aryl, aralkyl, heteroaryl, heteroaralkyl, cycloalkyl, alkanoyl, aralkanoyl, and heteroaralkanoyl, or
    $R^{11}$ and $R^{12}$, together with the atom to which they are bonded, form a 5- to 8-membered heterocyclo or heteroaryl ring;
$R^{13}$ is selected from the group consisting of hydrido and $C_1$–$C_6$ alkyl;
$R^{14}$ is selected from the group consisting of hydrido, $C_1$–$C_6$ alkyl, optionally substituted aryl, optionally substituted arylalkyl, and tetrahydropyranyl;
$W^1$ is selected from the group consisting of —$NR^{5a}COR^{6a}$, $NR^{5a}S(O)_zR^7$, —$NR^{5a}COOR^8$, —$NR^{5a}CONR^8R^9$, and $NR^{11}R^{12}$;
z is selected from the group consisting of zero, 1, and 2;
as to $R^{5a}$, $R^{6a}$, $R^7$, $R^8$, and $R^9$:
    $R^{5a}$ is selected from the group consisting of hydrido and $C_1$–$C_4$ alkyl, and $R^{6a}$ is selected from the group consisting of hydrido, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —$(CH_2)_x$—$NR^{11}R^{12}$,
    $R^{5a}$ and $R^{6a}$, together with the atoms to which they are bonded, form an optionally substituted 5- or 7-membered cyclic amide or imide, $R^{5a}$ is selected from the group consisting of hydrido and $C_1$–$C_4$ alkyl, and $R^7$ is selected from the group consisting of hydrido, alkyl, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —$(CH_2)_x$—$NR^{11}R^{12}$, $R^{5a}$ and $R^7$, together with the atoms to which they are bonded, form an optionally substituted 5- or 7-membered cyclic sulfonamide, $R^{5a}$ is selected from the group consisting of hydrido and $C_1$–$C_4$ alkyl, and $R^8$ and $R^9$ are independently selected from the group consisting of hydrido, alkyl, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —$(CH_2)_x$—$NR^{11}R^{12}$, or $R^{5a}$ is selected from the group consisting of hydrido and $C_1$–$C_4$ alkyl, and $R^8$ and $R^9$, together with the atom to which they are bonded, form a 5- to 7-membered ring having no greater than one ring atom selected from the group consisting of oxygen, nitrogen, and sulfur, with the remaining ring atoms being carbon; and any aryl or heteroaryl of $R^{6a}$, $R^7$, $R^8$, or $R^9$ is optionally substituted with one or more substituents independently selected from the group consisting of halo, $C_1$–$C_4$ alkyl, $C_1$–$C_4$ alkoxy, nitro, cyano, hydroxy, carboxy, hydroxycarbonylalkyl, —$(CH_2)_x$—$NR^{11}R^{12}$, trifluoromethyl, alkoxycarbonyl, aminocarbonyl, thio, alkylsulfonyl, carbonylamino, aminosulfonyl, alkylsulfonamino, alkoxyalkyl, cycloalkyloxy, alkylthioalkyl, and alkylthio.

2. A compound or salt according to claim 1, wherein n is 2.

3. A compound or salt according to claim 1, wherein $R^1$ is arylene.

4. A compound or a salt thereof, wherein:

the compound or salt is characterizeable in that the compound or salt selectively inhibits in vitro activity of human MMP-2, human MMP-3, and/or human MMP-13 over in vitro activity of human MMP-1;

the compound corresponds in structure to Formula I:

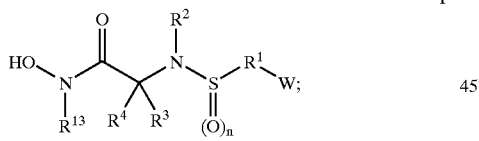

I n is selected from the group consisting of zero, 1, and 2;

W is —$NR^5COR^6$;

$R^1$ is selected from the group consisting of cycloalkylene, arylene, and heteroarylene;

$R^2$ is selected from the group consisting of alkyl, aralkyl, heteroaralkyl, cycloalkylalkyl, heterocycloalkylalkyl, hydroxycarbonylalkyl, aroylalkyl, and heteroaroylalkyl;

$R^3$ is selected from the group consisting of hydrido, alkyl, aryl, aralkyl, thioalkyl, heteroaralkyl, heteroaryl, alkoxyalkoxyalkyl, trifluoromethylalkyl, alkoxycarbonylalkyl, aralkoxycarbonylalkyl, hydroxycarbonylalkyl, alkoxyalkyl, heterocycloalkylalkyl, aryloxyalkyl, alkylthioalkyl, arylthioalkyl, heteroarylthioalkyl, a sulfoxide of any said thio-containing substituents, a sulfone of any said thio-containing substituents, —$(CH_2)_x$—$C(O)NR^{11}R^{12}$, and —$(CH_2)_y$—$W^1$;

each x is an integer from zero to 6;

y is an integer from 1 to 6;

$R^4$ is selected from the group consisting of hydrido and $C_1$–$C_4$ alkyl;

as to $R^5$ and $R^6$:

$R^5$ is selected from the group consisting of hydrido and $C_1$–$C_4$ alkyl; and $R^6$ is selected from the group consisting of hydrido, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —$(CH_2)_x$—$NR^{11}R^{12}$, wherein:

any aryl or heteroaryl of $R^6$ is optionally substituted with one or more substituents independently selected from the group consisting of halo, $C_1$–$C_6$ alkyl, $C_1$–$C_4$ alkoxy, nitro, cyano, hydroxy, carboxy, hydroxycarbonylalkyl, —$(CH_2)_x$—$NR^{11}R^{12}$, trifluoromethyl, alkoxycarbonyl, aminocarbonyl, thio, alkylsulfonyl, carbonylamino, aminosulfonyl, alkylsulfonamino, alkoxyalkyl, cycloalkyloxy, alkylthioalkyl, and alkylthio, or $R^5$ and $R^6$, together with the atoms to which they are bonded, form an optionally substituted 5- or 7-membered cyclic amide or imide;

as to each pair of $R^{11}$ and $R^{12}$:

$R^{11}$ and $R^{12}$ are independently selected from the group consisting of hydrido, alkyl, aryl, aralkyl, heteroaryl, heteroaralkyl, cycloalkyl, alkanoyl, aralkanoyl, and heteroaralkanoyl, or $R^{11}$ and $R^{12}$, together with the atom to which they are bonded, form a 5 to 8-membered heterocyclo or heteroaryl ring; and $R^{13}$ is selected from the group consisting of hydrido and $C_1$–$C_6$ alkyl;

$W^1$ is selected from the group consisting of —$NR^{5a}COR^{6a}$, $NR^{5a}S(O)_zR^7$, —$NR^{5a}COOR^8$, —$NR^{5a}CONR^8R^9$, and —$NR^{11}R^{12}$;

z is selected from the group consisting of zero, 1, and 2;

as to $R^{5a}$, $R^{6a}$, $R^7$ $R^8$, and $R^9$:

$R^{5a}$ is selected from the group consisting of hydrido and $C_1$–$C_4$ alkyl, and $R^{6a}$ is selected from the group consisting of hydrido, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —$(CH_2)_x$—$NR^{11}R^{12}$, $R^{5a}$ and $R^{6a}$, together with the atoms to which they are bonded, form an optionally substituted 5- or 7-membered cyclic amide or imide, $R^{5a}$ is selected from the group consisting of hydrido and $C_1$–$C_4$ alkyl, and $R^7$ is selected from the group consisting of hydrido, alkyl, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —$(CH_2)_x$—$NR^{11}R^{12}$, $R^{5a}$ and $R^7$, together with the atoms to which they are bonded, form an optionally substituted 5- or 7-membered cyclic sulfonamide, $R^{5a}$ is selected from the group consisting of hydrido and $C_1$–$C_4$ alkyl, and $R^8$ and $R^9$ are independently selected from the group consisting of hydrido, alkyl, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —(CH$_2$)$_x$—NR$^{11}$R$^{12}$, or R$^{5a}$ is selected from the group consisting of hydrido and C$_1$–C$_4$ alkyl, and R$^8$ and R$^9$, together with the atom to which they are bonded, form a 5- to 7-membered ring having no greater than one ring atom selected from the group consisting of oxygen, nitrogen, and sulfur, with the remaining ring atoms being carbon; and any aryl or heteroaryl of R$^{6a}$, R$^7$, R$^8$, or R$^9$ is optionally substituted with one or more substituents independently selected from the group consisting of halo, C$_1$–C$_4$ alkyl, C$_1$–C$_4$ alkoxy, nitro, cyano, hydroxy, carboxy, hydroxycarbonylalkyl, —(CH$_2$)$_x$—NR$^{11}$R$^{12}$, trifluoromethyl, alkoxycarbonyl, aminocarbonyl, thio, alkylsulfonyl, carbonylamino, aminosulfonyl, alkylsulfonamino, alkoxyalkyl, cycloalkyloxy, alkylthioalkyl, and alkylthio.

5. A compound or salt according to claim 4, wherein n is 2.

6. A compound or salt according to claim 5, wherein R$^1$ is arylene.

7. A compound or salt according to claim 6, wherein R$^4$ is hydrido.

8. A compound or salt according to claim 4, wherein the compound corresponds in structure to formula III:

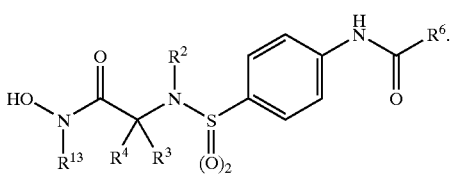

9. A compound or salt according to claim 8, wherein R$^{13}$ and R$^4$ are both hydrido.

10. A compound or salt according to claim 8, wherein R$^4$ is hydrido.

11. A salt according to claim 10, wherein the salt corresponds in structure to the following formula:

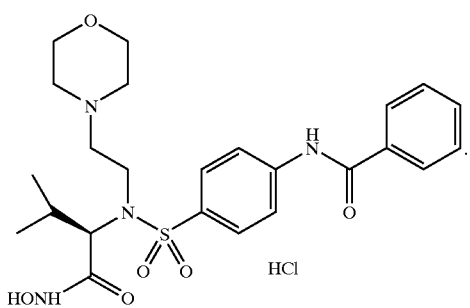

12. A compound or salt according to claim 8, wherein R$^6$ is heteroarylaryl.

13. A compound or salt according to claim 10, wherein the compound corresponds in structure to the following formula:

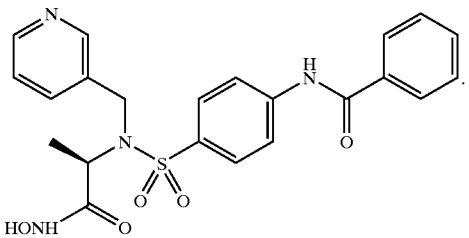

14. A process for treating a mammal having a condition associated with pathological matrix metalloprotease activity, wherein:

the process comprises administering a compound or a salt thereof in an MMP enzyme-inhibiting effective amount to the mammal;

the compound or salt is characterizeable in that the compound or salt selectively inhibits in vitro activity of human MMP-2, human MMP-3, and/or human MMP-13 over in vitro activity of human MMP-1;

the compound corresponds in structure to Formula I:

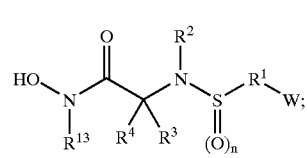

n is selected from the group consisting of zero, 1, and 2;

W is —NR$^5$COR$^6$;

R$^1$ is selected from the group consisting of cycloalkylene, arylene, and heteroarylene;

R$^2$ is selected from the group consisting of alkyl, aralkyl, heteroaralkyl, cycloalkylalkyl, heterocycloalkylalkyl, hydroxycarbonylalkyl, aroylalkyl, and heteroaroylalkyl;

R$^3$ is selected from the group consisting of hydrido, alkyl, aryl, aralkyl, thioalkyl, heteroaralkyl, heteroaryl, alkoxyalkoxyalkyl, trifluoromethylalkyl, alkoxycarbonylalkyl, aralkoxycarbonylalkyl, hydroxycarbonylalkyl, alkoxyalkyl, heterocycloalkylalkyl, aryloxyalkyl, alkylthioalkyl, arylthioalkyl, heteroarylthioalkyl, a sulfoxide of any said thio-containing substituents, a sulfone of any said thio-containing substituents, —(CH$_2$)$_x$—C(O)NR$^{11}$R$^{12}$, and —(CH$_2$)y—W$^1$, each x is an integer from zero to 6;

y is an integer from 1 to 6;

R$^4$ is selected from the group consisting of hydrido and C$_1$–C$_4$ alkyl;

as to R$^5$ and R$^6$:

R$^5$ is selected from the group consisting of hydrido and C$_1$–C$_4$ alkyl; and R$^6$ is selected from the group consisting of hydrido, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —(CH$_2$)$_x$13 NR$^{11}$R$^{12}$, wherein:

any aryl or heteroaryl group of R$^6$ is optionally substituted with one or more substituents independently selected from the group consisting of halo, C$_1$–C$_6$ alkyl, C$_1$–C$_4$ alkoxy, nitro, cyano, hydroxy, carboxy, hydroxycarbonylalkyl, —(CH$_2$)$_x$—NR$^{11}$R$^{12}$, trifluoromethyl, alkoxycarbonyl, aminocarbonyl, thio, alkylsulfonyl, carbonylamino, aminosulfonyl, alkylsulfonamino, alkoxyalkyl, cycloalkyloxy, alkylthioalkyl, and alkylthio, or R$^5$ and R$^6$, together with the atoms to which they are bonded, form an optionally substituted 5- or 7-membered cyclic amide or imide;

as to each pair of R$^{11}$ and R$^{12}$:

R$^{11}$ and R$^{12}$ are independently selected from the group consisting of hydrido, alkyl, aryl, aralkyl, heteroaryl, heteroaralkyl, cycloalkyl, alkanoyl, aralkanoyl, and heteroaralkanoyl, or R$^{11}$ and R$^{12}$, together with the atom to which they are bonded, form a 5 to 8-membered heterocyclo or heteroaryl ring; and R$^{13}$ is selected from the group consisting of hydrido and C$_1$–C$_6$ alkyl;

W$^1$ is selected from the group consisting of —NR$^{5a}$COR$^{6a}$, NR$^{5a}$S(O)$_z$R$^7$, —NR$^{5a}$COOR$^8$, —NR$^{5a}$CONR$^8$R$^9$, and —NR$^{11}$R$^{12}$;

z is selected from the group consisting of zero, 1, and 2;

as to R$^{5a}$, R$^{6a}$, R$^7$, R$^8$ and R$^9$:

R$^{5a}$ is selected from the group consisting of hydrido and C$_1$–C$_4$ alkyl, and R$^{6a}$ is selected from the group consisting of hydrido, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —(CH$_2$)$_x$—NR$^{11}$R$^{12}$, R$^{5a}$ and R$^{6a}$, together with the atoms to which they are bonded, form an optionally substituted 5- or 7-membered cyclic amide or imide, R$^{5a}$ is selected from the group consisting of hydrido and C$_1$–C$_4$ alkyl, and R$^7$ is selected from the group consisting of hydrido, alkyl, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —(CH$_2$)$_x$—NR$^{11}$R$^{12}$, R$^{5a}$ and R$^7$, together with the atoms to which they are bonded, form an optionally substituted 5- or 7-membered cyclic sulfonamide, R$^{5a}$ is selected from the group consisting of hydrido and C$_1$–C$_4$ alkyl, and R$^8$ and R$^9$ are independently selected from the group consisting of hydrido, alkyl, cycloalkyl, heterocycloalkyl, aryl, heteroaryl, aralkyl, heteroaralkyl, cycloalkylalkyl, heterocycloalkylalkyl, alkoxyalkyl, alkylthioalkyl, and —(CH$_2$)$_x$—NR$^{11}$R$^{12}$, or R$^{5a}$ is selected from the group consisting of hydrido and C$_1$–C$_4$ alkyl, and R$^8$ and R$^9$, together with the atom to which they are bonded, form a 5- to 7-membered ring having no greater than one ring atom selected from the group consisting of oxygen, nitrogen, and sulfur, with the remaining ring atoms being carbon; and any aryl or heteroaryl of R$^{6a}$, R$^7$, R$^8$, or R$^9$ is optionally substituted with one or more substituents independently selected from the group consisting of halo, C$_1$–C$_4$ alkyl, C$_1$–C$_4$ alkoxy, nitro, cyano, hydroxy, carboxy, hydroxycarbonylalkyl, —(CH$_2$)$_x$— NR$^{11}$R$^{12}$, trifluoromethyl, alkoxycarbonyl, aminocarbonyl, thio, alkylsulfonyl, carbonylamino, aminosulfonyl, alkylsulfonamino, alkoxyalkyl, cycloalkyloxy, alkylthioalkyl, and alkylthio.

15. The process according to claim 14 wherein n is 2.

16. The process according to claim 14 wherein R$^1$ is arylene.

17. The process according to claim 14, wherein said compound corresponds in structure to formula III:

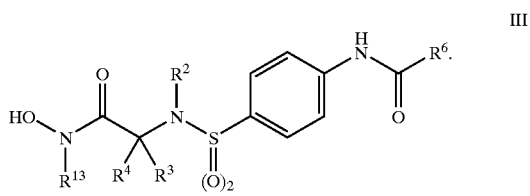

18. The process according to claim 14, wherein said compound or salt is administered a plurality of times.

19. A compound or salt according to claim 10 wherein the compound corresponds in structure to the following formula:

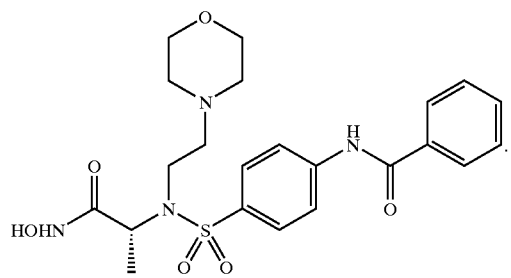

20. A salt according to claim 10, wherein the salt corresponds in structure to the following formula:

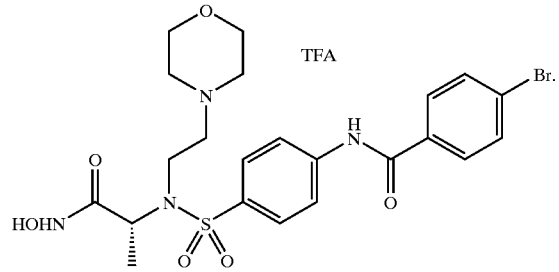

21. A salt according to claim 10, wherein the salt corresponds in structure to the following formula:

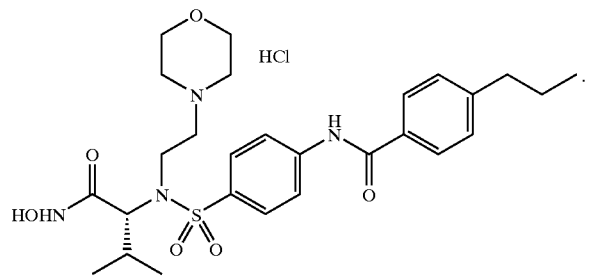

22. A salt according to claim 10, wherein the salt corresponds in structure to the following formula:

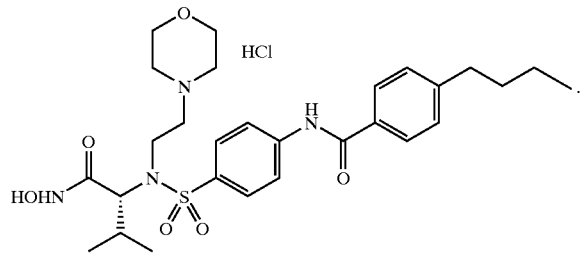

23. A salt according to claim 10, wherein the salt corresponds in structure to the following formula:

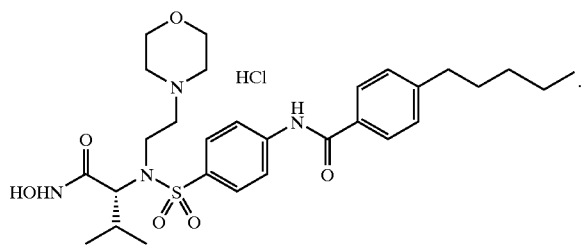

24. A salt according to claim 10, wherein the salt corresponds in structure to the following formula:

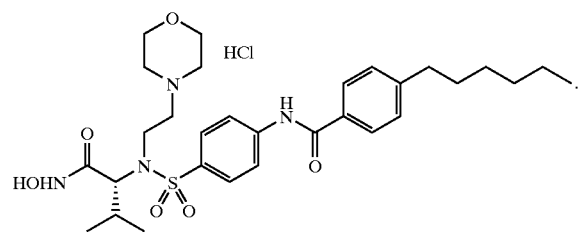

25. A salt according to claim 10, wherein the salt corresponds in structure to the following formula:

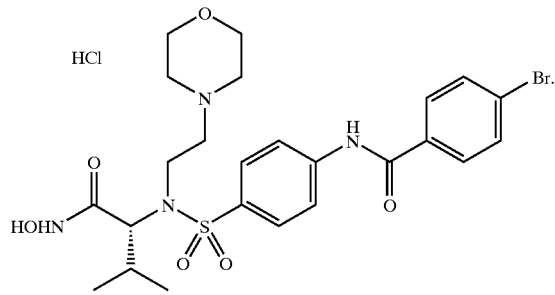

26. A salt according to claim 10, wherein the salt corresponds in structure to the following formula:

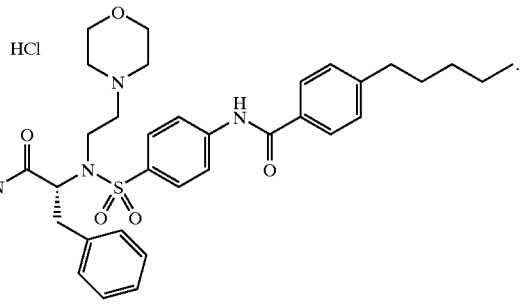

27. A compound or salt according to claim 10, wherein the compound corresponds in structure to the following formula:

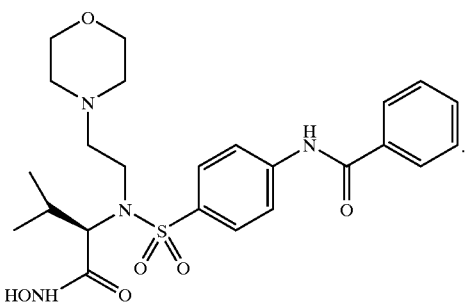

28. A compound or salt according to claim 10, wherein the compound corresponds in structure to the following formula:

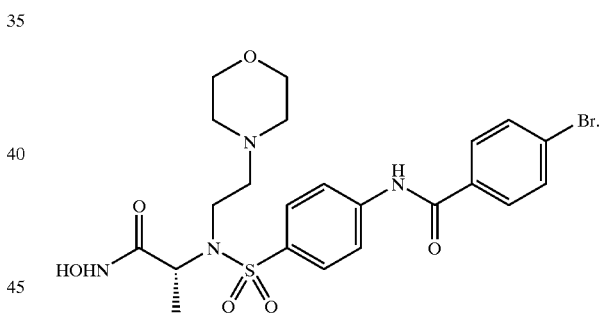

29. A compound or salt according to claim 10, wherein the compound corresponds in structure to the following formula:

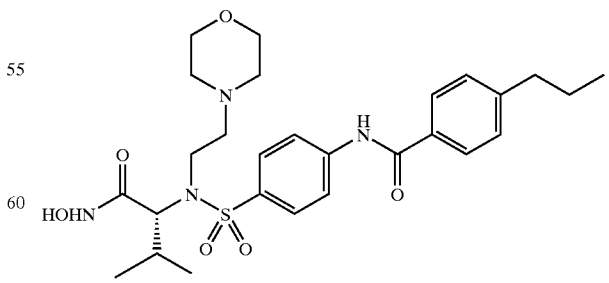

30. A compound or salt according to claim 10, wherein the compound corresponds in structure to the following formula:

31. A compound or salt according to claim 10, wherein the compound corresponds in structure to the following formula:

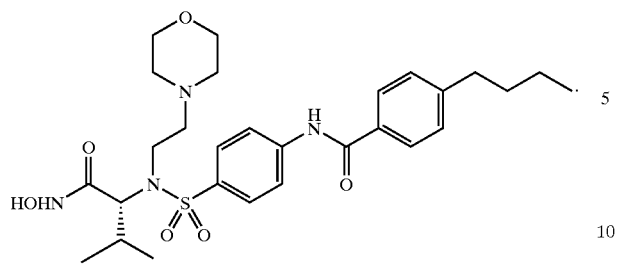

32. A compound or salt according to claim 10, wherein the compound corresponds in structure to the following formula:

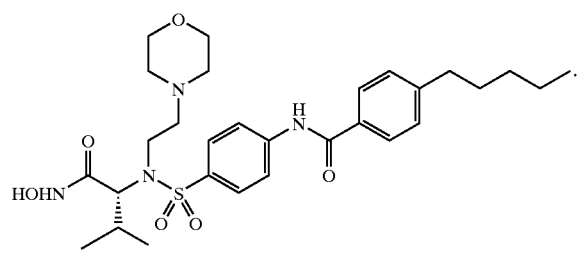

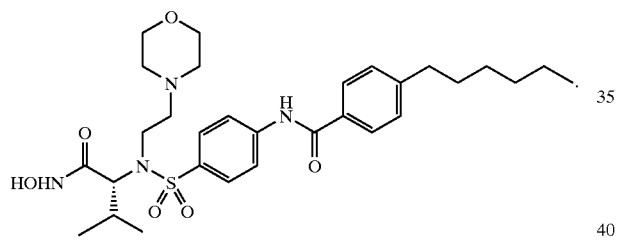

33. A compound or salt according to claim 10, wherein the compound corresponding in structure to the following formula:

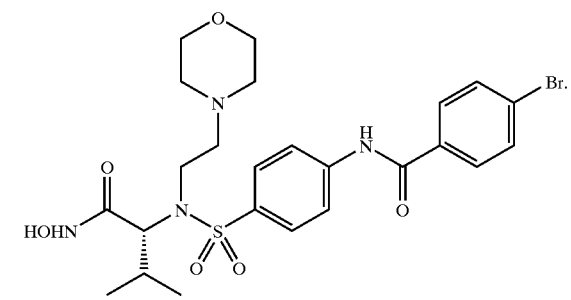

34. A compound or salt according to claim 10, wherein the compound corresponding to the following formula:

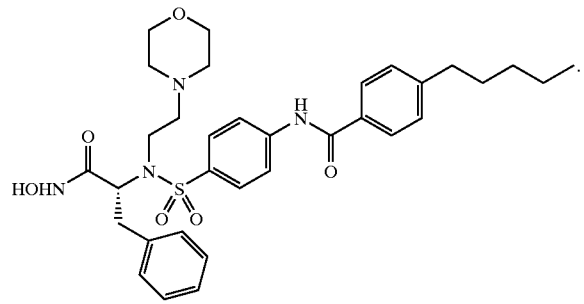

* * * * *